US008446463B2

(12) United States Patent
Fleming et al.

(10) Patent No.: US 8,446,463 B2
(45) Date of Patent: May 21, 2013

(54) APPARATUS, METHOD AND ARTICLE TO PERFORM ASSAYS USING ASSAY STRIPS

(75) Inventors: James E. Fleming, Spokane, WA (US); Jesse M. McGrew, Spokane, WA (US); Stephen P. McGrew, Spokane, WA (US); Patrick Nicholes, Spokane, WA (US); Johnny Humphreys, Veradale, WA (US)

(73) Assignee: GenPrime, Inc., Spokane, WA (US)

( * ) Notice: Subject to any disclaimer, the term of this patent is extended or adjusted under 35 U.S.C. 154(b) by 792 days.

(21) Appl. No.: 12/538,716

(22) Filed: Aug. 10, 2009

(65) Prior Publication Data

US 2010/0045789 A1    Feb. 25, 2010

Related U.S. Application Data

(60) Provisional application No. 61/189,931, filed on Aug. 22, 2008.

(51) Int. Cl.
*H04N 7/18* (2006.01)
*G06K 9/00* (2006.01)

(52) U.S. Cl.
USPC ............................................. 348/61; 382/128

(58) Field of Classification Search
USPC ............................................. 348/61; 382/128
See application file for complete search history.

(56) References Cited

U.S. PATENT DOCUMENTS

| 4,103,287 | A | * | 7/1978 | Frank ............................. 382/246 |
| 4,718,090 | A | * | 1/1988 | Cooper, Jr. ..................... 382/204 |
| 5,403,551 | A | | 4/1995 | Galloway et al. |
| 5,408,535 | A | | 4/1995 | Howard, III et al. |
| 5,429,804 | A | | 7/1995 | Sayles |
| 5,569,608 | A | | 10/1996 | Sommer |
| 5,707,797 | A | * | 1/1998 | Windle ........................ 435/6.16 |
| 6,136,549 | A | | 10/2000 | Feistel |
| 6,165,734 | A | * | 12/2000 | Garini et al. ................ 435/7.21 |
| 6,248,596 | B1 | | 6/2001 | Durst et al. |
| 6,404,906 | B2 | * | 6/2002 | Bacus et al. .................. 382/128 |
| 6,416,959 | B1 | * | 7/2002 | Giuliano et al. ............... 435/7.2 |
| 6,436,721 | B1 | | 8/2002 | Kuo et al. |

(Continued)

FOREIGN PATENT DOCUMENTS

| EP | 0 953 149 B1 | 9/2004 |
| WO | 0046598 A1 | 8/2000 |

OTHER PUBLICATIONS

International Search Report, mailed Apr. 6, 2010, for PCT/US2009/053404, 3 pages.

(Continued)

*Primary Examiner* — Jerry Dennison
(74) *Attorney, Agent, or Firm* — Seed IP Law Group PLLC

(57) ABSTRACT

An assay system includes an optical imager to acquire high resolution images of assay strips (e.g., lateral flow immunochromatographic test strips) and performs image processing to identify individual assay strips and determine results for each assay strip, by quantifies the presence or absence of test signal line(s) and control signal line(s). Assay strips may be in a holder or carrier contained in a specimen container also holding a specimen. The assay system automatically logs all results and data to a database that stores a high resolution image of the original immunochromatographic assay, the values of test line(s) and control line(s), and the test result. A user interface directs an end user through operation.

28 Claims, 35 Drawing Sheets

U.S. PATENT DOCUMENTS

| | | | |
|---|---|---|---|
| 6,607,922 B2 | 8/2003 | LaBorde | |
| 6,671,624 B1* | 12/2003 | Dunlay et al. | 702/19 |
| 6,936,476 B1 | 8/2005 | Anderson et al. | |
| 7,020,307 B2* | 3/2006 | Hinton et al. | 382/109 |
| 7,117,098 B1* | 10/2006 | Dunlay et al. | 702/21 |
| 7,267,799 B1 | 9/2007 | Borich et al. | |
| 7,323,139 B2 | 1/2008 | LaBorde et al. | |
| 7,330,606 B2* | 2/2008 | Yakhini et al. | 382/294 |
| 7,371,582 B2 | 5/2008 | Nahm et al. | |
| 7,390,675 B2 | 6/2008 | Feistel | |
| 7,403,661 B2* | 7/2008 | Curry et al. | 382/232 |
| 7,444,005 B2* | 10/2008 | Bachur et al. | 382/107 |
| 7,526,114 B2* | 4/2009 | Xia et al. | 382/128 |
| 7,818,130 B2* | 10/2010 | Sipe et al. | 702/19 |
| 7,910,873 B2* | 3/2011 | Lue et al. | 250/208.2 |
| 7,940,968 B2* | 5/2011 | Seul et al. | 382/128 |
| 7,957,911 B2* | 6/2011 | Harris et al. | 702/19 |
| 8,059,893 B2* | 11/2011 | Prusia | 382/173 |
| 8,117,071 B1* | 2/2012 | Fitch et al. | 705/23 |
| 2002/0009389 A1* | 1/2002 | Lappe et al. | 422/58 |
| 2002/0009390 A1* | 1/2002 | Lappe et al. | 422/58 |
| 2002/0031783 A1* | 3/2002 | Empedocles et al. | 435/7.1 |
| 2002/0159625 A1* | 10/2002 | Elling | 382/133 |
| 2003/0036096 A1* | 2/2003 | Ravkin et al. | 435/7.1 |
| 2003/0036855 A1* | 2/2003 | Harris et al. | 702/19 |
| 2003/0039384 A1* | 2/2003 | Bacus et al. | 382/128 |
| 2003/0040031 A1* | 2/2003 | Kim et al. | 435/29 |
| 2003/0156739 A1* | 8/2003 | Hinton et al. | 382/109 |
| 2003/0190075 A1* | 10/2003 | Averbuch et al. | 382/199 |
| 2004/0033610 A1* | 2/2004 | Lovell et al. | 436/43 |
| 2004/0101912 A1* | 5/2004 | Rubin et al. | 435/7.2 |
| 2004/0146917 A1 | 7/2004 | Cork et al. | |
| 2004/0264807 A1* | 12/2004 | Yakhini et al. | 382/289 |
| 2005/0008212 A1* | 1/2005 | Ewing et al. | 382/133 |
| 2005/0180642 A1* | 8/2005 | Curry et al. | 382/232 |
| 2005/0180647 A1* | 8/2005 | Curry et al. | 382/243 |
| 2005/0203353 A1* | 9/2005 | Ma et al. | 600/315 |
| 2006/0039603 A1* | 2/2006 | Koutsky | 382/165 |
| 2006/0062440 A1* | 3/2006 | Hollars et al. | 382/128 |
| 2006/0072817 A1* | 4/2006 | Lee et al. | 382/173 |
| 2006/0172280 A1* | 8/2006 | Kim et al. | 435/4 |
| 2006/0222227 A1* | 10/2006 | Seul et al. | 382/128 |
| 2006/0275799 A1* | 12/2006 | Banerjee et al. | 435/6 |
| 2006/0292040 A1 | 12/2006 | Wickstead et al. | |
| 2008/0123945 A1* | 5/2008 | Andrew et al. | 382/164 |
| 2008/0181482 A1* | 7/2008 | Bouchard et al. | 382/133 |
| 2008/0260233 A1* | 10/2008 | Hays et al. | 382/133 |
| 2008/0304723 A1* | 12/2008 | Hsieh et al. | 382/128 |
| 2009/0068064 A1* | 3/2009 | Gordon | 422/82.05 |
| 2009/0208104 A1* | 8/2009 | Prusia | 382/173 |
| 2010/0033724 A1* | 2/2010 | Cork et al. | 356/445 |
| 2010/0045789 A1* | 2/2010 | Fleming et al. | 348/79 |
| 2010/0239137 A1* | 9/2010 | Pugia et al. | 382/128 |
| 2011/0255756 A1* | 10/2011 | Harris et al. | 382/128 |

OTHER PUBLICATIONS

Written Opinion, mailed Apr. 6, 2010, for PCT/US2009/053404, 7 pages.

Extended European Search Report for corresponding European Application No. 09808610.1, dated Jan. 30, 2013, 10 pages.

Haralick et al., "Image Segmentation Techniques," *Computer Vision, Graphics, and Image Processing* 29:100-132, 1985.

\* cited by examiner

YOU ARE CURRENTLY LOGGED IN AS: 1810 — KIM

TEST KIT NUMBER: 1808 — 001

NUMBER OF SAMPLES: 2612 — 1

INSTRUCTIONS — 2602
2602a
A] SCAN B.C.T. KIT NUMBER
B] ENTER NUMBER OF SAMPLES TO BE TESTED
C] SCAN PLATELET BAG
D] COLLECT 1 mL PLATELET SAMPLE IN TUBE AND SCAN
E] REPEAT STEPS C & D FOR REMAINING SAMPLES

SCAN BAG: 1804
1: 001  2:  3:  4:
5:  6:  7:  8:

SCAN TUBE: 1806
1: 001  2:  3:  4:
5:  6:  7:  8:

1814 — NEXT STEP

1816 — LOGOUT

3702 — Scanned by Demo User at 7/16/2009 11:31:41 AM — 3712

Package P0113259
Patient P0113259 / John Doe
Employer GenPrime

Result: Presumptive positive
Verified Yes

3704

Adulteration: Ox: pass, pH: pass, S.G.: pass, Temp.: pass

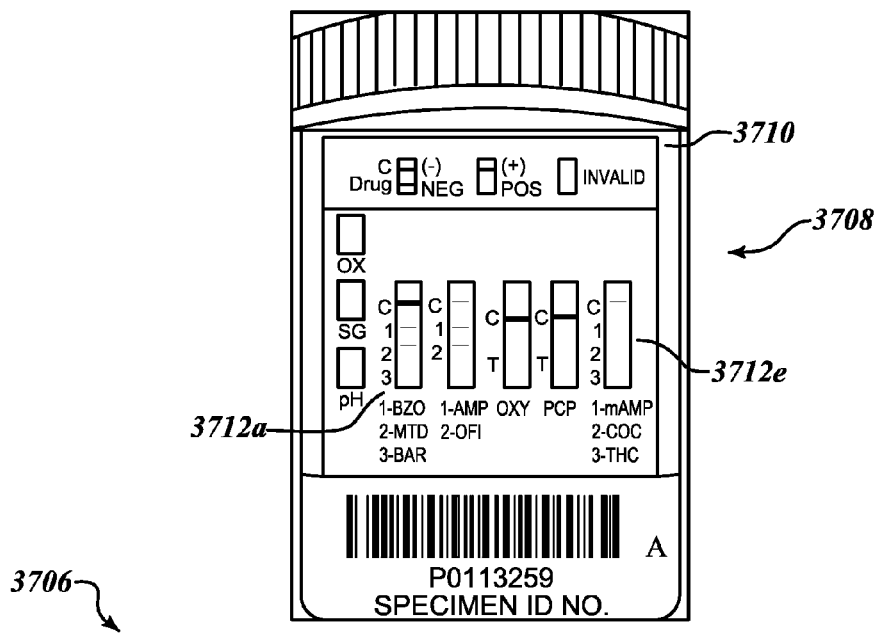

| Line | Density | Threshold | Result |
|---|---|---|---|
| Control 1 | 41.38 | 10.00 | Present |
| BZO | 9.92 | 5.00 | Negative |
| MTD | 5.04 | 5.00 | Negative |
| BAR | 3.47 | 5.00 | Presumptive positive |
| Control 2 | 27.75 | 10.00 | Present |
| BZO | 19.08 | 5.00 | Negative |
| MTD | 4.63 | 5.00 | Presumptive positive |
| Control 3 | 31.49 | 10.00 | Present |
| BZO | 13.29 | 5.00 | Negative |
| Control 4 | 40.62 | 10.00 | Present |
| BZO | 3.13 | 5.00 | Presumptive positive |
| Control 5 | 18.21 | 10.00 | Present |
| BZO | 2.74 | 5.00 | Presumptive positive |
| MTD | 2.21 | 5.00 | Presumptive positive |
| BAR | 2.32 | 5.00 | Presumptive positive |

*FIG. 37*

APPARATUS, METHOD AND ARTICLE TO PERFORM ASSAYS USING ASSAY STRIPS

CROSS REFERENCE TO RELATED APPLICATIONS

This application claims benefit under 35 U.S.C. 119(e) of U.S. Provisional Patent Application Ser. No. 61/189,931, filed Aug. 22, 2008 and entitled "APPARATUS, METHOD AND ARTICLE TO PERFORM ASSAYS USING ASSAY STRIPS," which is incorporated herein by reference in its entirety.

BACKGROUND

1. Technical Field

The present disclosure generally relates to the performance of assays using assay strips, for example chromatographic lateral flow strips.

2. Description of the Related Art

Performance of biological assays has been by greatly facilitated by the introduction of substrates for performing chromatographic assays. Since its conception, numerous substrates have been proposed for performing chromatographic assays. Such substrates are commonly referred to as assay test strips or immunochromatographic strips. One type of assay strip is commonly referred to as chromatographic lateral flow strips or lateral flow strips. Other types of assay strips include western blots, southern blots, electrophoresis gels, dot blots, etc. Assay strips may be used for both qualitative and semi-quantitative assays, which typically employ visual detection schemes.

Assay strips typically provide a matrix of material through which a fluid test sample, which may or may not contain an analyte that is being tested for, can flow. In use, a liquid test sample suspected of containing an analyte to be detected is applied to an application zone of the assay strip. In the case of lateral flow strips, the test fluid and analyte suspended or dissolved therein can flow from the application zone to a detection zone, for example via capillary action. The test fluid typically flows horizontally though the matrix (i.e., laterally), although vertical layers may be employed. At the detection zone the appearance or absence of a visible signal (e.g., test results signal line) reveals the presence or absence of the analyte. Assay strips typically visually display two parallel lines, known as capture or signal lines. One of the lines indicates that test strip performance has not been compromised. The second line becomes visible only when the sample contains an amount of analyte in excess of a minimum or threshold concentration. In such assay strips, the capture or signal lines consist of immobilized capture reagents or receptors which are pre-applied to the matrix during manufacture.

In particular, lateral flow type assay strips may include a binding partner that immunospecifically binds the analyte to be detected and which bears a detectable label. The binding may be competitive binding or non-competitive. Competitive assays are particularly suited to detect smaller molecules, such as drugs and drug metabolites. Non-competitive immunoassays are primarily used for detection of large molecules such as proteins, large hormones, or molecules which have multiple binding sites. The detection zone may include a substrate for a label capable of providing a colored response in the presence of the label. The assay strip may also contain a zone in which analyte is immobilized so that labeled binding partner which is not combined due to an absence of analyte in the sample will be captured and prevented from reaching the detection zone. Multi-zone assay strips are also known, which may include a detection zone that contains an immobilized form of a binding substance for a labeled reagent. The labeled reagent bears a detectable chemical group having a detectable physical property so that it does not require a chemical reaction with another substance. Examples of such include colored species, fluorescers, phosphorescent molecules, radio-isotopes and electro-active moieties.

Results have traditionally been interpreted visually by the operator. Resulting test and control signal lines vary greatly in intensity, resulting in highly subjective user analysis. Even positive results may be indicated by an extremely faint, but present, test results signal line. In such circumstances, some operators may visually conclude that no test line is present, while other operators may correctly identify the presence of a test line. The issue is further clouded by the nature of assay strips which sometimes contain a high level of background color, that may be incorrectly identified as a positive test line. Thus, assay strips typically provide results which are at best semi-quantitative and are typically subject to variance by the person performing the assay. Since quantification cannot be performed accurately with the naked eye and hence an exact amount of an analyte cannot be determined, application is restricted. Thus, while assay strip formats provide rapid results, are simple to operate, and are more cost-effective than conventional formats, such formats are typically not subject to quantification.

Different approaches to performing assays using assay strips are desirable, particular ones that address some of the above described problems, as well as approaches that address other problems.

BRIEF SUMMARY

At least one aspect may be summarized as an assay system to perform assays using assay strips, including a housing having an interior and at least one entrance providing access to the interior, the at least one entrance sized to receive at least one assay strip therein without any assay strip carrier; an imager subsystem operable to capture images of any of the assay strips received in the interior of the housing; and a processor subsystem comprising at least one processor and at least one processor-readable memory communicatively coupled to the at least one processor, the at least one processor also communicatively coupled to the imager subsystem to receive image information representative of the images captured by the imager subsystem, the at least one processor configured to identify individual ones of the assay strips in the image from the image information, the at least one processor further configured to perform an objective assay evaluation based at least in part on at least one signal line on each of the assay strips and based at least in part on at least one configurable criteria.

At least one processor may be configured to store a respective high resolution digital representation of the captured image of each of at least some of the assay strips to a computer-readable storage medium along with at least some identification information logically associated with the respective high resolution digital representation of the captured image of each of the at least some of the assay strips.

At least one processor may be configured to store a respective high resolution digital representation of the captured image of each of at least some of the assay strips to a computer-readable storage medium along with at least some information indicative of a result of the objective assay evaluation for each of at least some of the assay strips logically associated with the respective high resolution digital representation of the captured image of each of the at least some of the assay strips.

The assay system may include the computer-readable storage medium. The assay system may include a port that removably communicatively couples to the computer-readable storage medium and that is configured to write to the computer-readable storage medium.

The at least one processor may be configured to identify individual ones of the assay strips in the image from the image information, by: a first iteration of pixel transformation based on a first color of a plurality of pixels; a first iteration of blob analysis on a set of the plurality of pixels resulting from the first iteration of pixel transformation to identify a first number of blobs; and a first iteration of blob pairing on the first number of blobs identified in the first iteration of blob analysis.

The at least one processor may be configured to identify individual ones of the assay strips in the image from the image information, further by: a second iteration of pixel transformation based on a second color of a plurality of pixels; a second iteration of blob analysis on a set of the plurality of pixels resulting from the second iteration of pixel transformation to identify a second number of blobs; and a second iteration of blob pairing on the second number of blobs identified in the second iteration of blob analysis. Additional iterations may be performed.

The at least one processor may be configured to identify any machine-readable symbols in the image from the image information, and to decode the identified machine-readable symbols, if any. At least some information decoded from the identified machine-readable symbols may be the identification information, and the at least one processor may be configured to logically associate the identification information with respective ones of the assay strips which carried the machine-readable symbol.

The assay system may include a user interface including a number of user selectable inputs that correspond to respective ones of a number of configuration modes, each of the configuration modes mapped to a respective type of assay strip, where in response to selection of one of the user selectable inputs the processor subsystem reconfigures the at least one configurable criteria. The at least one configurable criteria may include a threshold level for the objective assay evaluation. The at least one configurable criteria may include at least one aspect of a physical format of the assay strips of the respective type of assay strip. At least two of the configuration modes may be mapped to respective assay strips from at least two different flow strip producing commercial entities.

The at least one processor may be configured to perform the objective assay evaluation by objectively quantifying an intensity of at least one positive results signal line on each of the assay strips. The at least one processor may be configured to perform the objective assay evaluation by evaluating at least one control signal line on each of the assay strips.

The image subsystem may include a two dimensional array that images an area greater than an area of a single assay strip. The image subsystem may include a one dimensional array mounted for movement with respect to the at least one assay strip to image an area greater than an area of a single assay strip. The interior of the housing may be dark and the image subsystem may include a least one of a mirror, a prism, an optical filter or an image processing filter.

At least one aspect may be summarized as a method of operating an assay system to perform assays of assay strips, including receiving a number of assay strips in an interior of a housing; capturing at least one image of a portion of the interior of the housing in which the assay strips are received; computationally identifying individual ones of the assay strips in the captured image; and computationally performing the objective assay evaluation for each of the identified individual ones of the assay strips that appear in the captured image based at least in part on a representation of at least one signal line of each of the assay strips in the captured image. The captured image may be a high resolution image.

The entrance may include a plurality of slots, each slot sized and dimensioned to receive a respective one of the assay strips therein.

Receiving a number of assay strips in an interior of a housing may include receiving a plurality of assay strips in the housing arranged such that at least a portion of each of a plurality of flow strips is exposed to an imager. Capturing at least one image in the interior of the housing may include capturing at least one image of an area in the interior of the housing having a dimension that is greater than a dimension of a single assay strip. Capturing at least one high resolution image in the interior of the housing may include capturing at least one high resolution image of an area in the interior of the housing having a length and a width that is greater than a length and a width of at least two adjacent assay strips.

Computationally identifying individual ones of the assay strips in the captured high resolution image may include performing a first iteration of pixel transformation based on a first color of a plurality of pixels in the high resolution image; performing a first iteration of blob analysis on a of the plurality of pixels resulting from the first iteration of pixel transformation to identify a first number of blobs; and performing a first iteration of blob pairing on the first number of blobs identified in the first iteration of blob analysis. Computationally identifying individual ones of the assay strips in the captured image may include performing a second iteration of pixel transformation based on a second color of a plurality of pixels; performing a second iteration of blob analysis on a of the plurality of pixels resulting from the second iteration of pixel transformation to identify a second number of blobs; and performing a second iteration of blob pairing on the second number of blobs identified in the second iteration of blob analysis.

The method may further include identifying any machine-readable symbols in the captured high resolution image; and decoding the identified machine-readable symbols, if any. The method may further include logically associating identification information decoded from the identified machine readable symbols with respective ones of the assay strips which appear in the high resolution image. The method may further include storing a respective digital representation of a portion of the captured high resolution image of each of at least some of the assay strips to a computer-readable storage medium along with at least some identification information logically associated with the respective digital representation of the respective portion of the captured high resolution image of each of the at least some of the assay strips.

The method may further include storing a respective digital representation of a portion of the captured high resolution image of each of at least some of the assay strips to a computer-readable storage medium along with at least some information indicative of a result of the objective assay evaluation for each of at least some of the assay strips logically associated with the respective digital representation of the respective portion of the captured high resolution image of each of the at least some of the assay strips. The storing may include storing to a removable computer-readable storage medium.

The method may further include computationally performing the objective assay evaluation for each of the identified individual ones of the assay strips that appear in the captured high resolution image based at least in part on a representation of at least one signal line of each of the assay strips in the captured high resolution image. Such may include objectively quantifying an intensity of at least one positive results signal line on each of the assay strips represented in the captured high resolution image. Such may further include evaluating at least one control signal line on each of the assay strips represented in the captured high resolution image.

At least one aspect may be summarized as a computer-readable medium that stores instructions that cause an assay system to perform assays of assay strips, by: capturing at least one high resolution image of a portion of the interior of the housing in which a number of assay strips are received; computationally identifying individual ones of the assay strips in the captured high resolution image; and computationally performing the objective assay evaluation for each of the identified individual ones of the assay strips that appear in the captured high resolution image based at least in part on a representation of at least one signal line of each of the assay strips in the captured high resolution image.

Computationally identifying individual ones of the assay strips in the captured high resolution image may include performing a first iteration of pixel transformation based on a first color of a plurality of pixels in the high resolution image; performing a first iteration of blob analysis on a of the plurality of pixels resulting from the first iteration of pixel transformation to identify a first number of blobs; and performing a first iteration of blob pairing on the first number of blobs identified in the first iteration of blob analysis.

Computationally identifying individual ones of the assay strips in the captured image may include performing a second iteration of pixel transformation based on a second color of a plurality of pixels; performing a second iteration of blob analysis on a of the plurality of pixels resulting from the second iteration of pixel transformation to identify a second number of blobs; and performing a second iteration of blob pairing on the second number of blobs identified in the second iteration of blob analysis. Computationally identifying individual ones of the assay strips in the captured image may include performing a second iteration of pixel transformation based on additionally colors (e.g., a tertiary color).

The instructions may cause the assay system to perform assays of assay strips, further by: identifying any machine-readable symbols in the captured high resolution image; and decoding the identified machine-readable symbols, if any. The instructions may cause the assay system to perform assays of assay strips, further by: logically associating identification information decoded from the identified machine readable symbols with respective ones of the assay strips which appear in the high resolution image. The instructions may cause the assay system to perform assays of assay strips, further by: storing a respective digital representation of a portion of the captured high resolution image of each of at least some of the assay strips to a computer-readable storage medium along with at least some identification information logically associated with the respective digital representation of the respective portion of the captured high resolution image of each of the at least some of the assay strips. The instructions may cause the assay system to perform assays of assay strips, further by: storing a respective digital representation of a portion of the captured high resolution image of each of at least some of the assay strips to a computer-readable storage medium along with at least some information indicative of a result of the objective assay evaluation for each of at least some of the assay strips logically associated with the respective digital representation of the respective portion of the captured high resolution image of each of the at least some of the assay strips.

Computationally performing the objective assay evaluation for each of the identified individual ones of the assay strips that appear in the captured high resolution image based at least in part on a representation of at least one signal line of each of the assay strips in the captured high resolution image may include objectively quantifying an intensity of at least one positive results signal line on each of the assay strips represented in the captured high resolution image. Computationally performing the objective assay evaluation for each of the identified individual ones of the assay strips that appear in the captured high resolution image based at least in part on a representation of at least one signal line of each of the assay strips in the captured high resolution image may include evaluating at least one control signal line on each of the assay strips represented in the captured high resolution image.

At least one aspect may be summarized as an assay system to perform assays using assay strips, including a housing an entrance sized to receive at least one assay strip therein; an imager subsystem operable to capture images of any of the assay strips received in the interior of the housing; and a processor subsystem comprising at least one processor communicatively coupled to the imager subsystem to receive image information representative of the images captured by the imager subsystem, the at least one processor configured to perform an objective assay evaluation based at least in part on at least one test results signal line and at least one control signal line on each of the assay strips and based at least in part on at least one configurable criteria; and a user interface including a number of user selectable inputs that correspond to respective ones of a number of configuration modes, each of the configuration modes mapped to a respective type of assay strip, where in response to selection of one of the user selectable inputs the processor subsystem reconfigures the at least one configurable criteria used to perform the objective assay evaluation.

The at least one configurable criteria may include a threshold level to objectively evaluate the test results signal line. The at least one configurable criteria may include at least one aspect of a physical format of the assay strips of the respective type of assay strip. At least two of the configuration modes may be mapped to respective assay strips of at least two different types. At least two of the configuration modes may be mapped to respective assay strips of at least two different immunochromatographic tests. At least two of the configuration modes may be mapped to respective assay strips from at least two different assay strip producing commercial entities. The user interface may include indicia indicative of a plurality of different assay strip products. The user interface may include at least one input device configured to allow the entry of a subject identifier that uniquely identifies a subject from which a sample on the assay strip was taken, and a logical association between the objective assay evaluation of the assay strip and the subject identifier may be stored. The at least one processor may be configured to perform the objective assay evaluation by objectively quantifying an intensity of at least one positive results signal line on each of the assay strips. The at least one processor may be configured to perform the objective assay evaluation by evaluating at least one control signal line on each of the assay strips. The entrance may include a plurality of slots, each slot sized and dimensioned to receive a respective one or the assay strips therein.

At least one aspect may be summarized as a method of operating an assay system to perform assays of assay strips, including receiving a user input indicative of at least one value of at least one configurable criteria to be used in performing an objective assay evaluation; receiving a number of assay strips in an interior of a housing; capturing at least one image a portion of the interior of the housing in which the assay strips are received; and computationally performing the objective assay evaluation for each of the assay strips in the captured image based at least in part on a representation of at least one signal line of each of the assay strips in the captured image and based at least in part on the user input indicative of the at least one value of at least one user configurable criteria.

Receiving a user input indicative of at least one value of at least one configurable criteria to be used in performing an objective assay evaluation may include receiving a user input indicative of a threshold level for the objective assay evaluation. Receiving a user input indicative of at least one value of at least one configurable criteria to be used in performing an objective assay evaluation may include receiving a user input indicative of a threshold intensity level for a positive results signal line. Receiving a user input indicative of at least one value of at least one configurable criteria to be used in performing an objective assay evaluation may include receiving a value indicative of a physical format of the assay strips of the respective type of assay strip. Receiving a user input indicative of at least one value of at least one configurable criteria to be used in performing an objective assay evaluation may include receiving a value indicative of a type of assay strip. Receiving a user input indicative of at least one value of at least one configurable criteria to be used in performing an objective assay evaluation may include receiving a value indicative of a assay strip manufacturer. Receiving a number of assay strips in an interior of a housing may include receiving a plurality of assay strips in the housing arranged such that at least a portion of each of a plurality of flow strips is exposed to an imager.

Capturing at least one image in the interior of the housing may include capturing at least one image of an area in the interior of the housing having a dimension that is greater than a dimension of a single assay strip. Capturing at least one image in the interior of the housing may include capturing at least one image of an area in the interior of the housing having a length and a width that is greater than a length and a width of at least two adjacent assay strips.

The method may further include computationally identifying individual ones of the assay strips in the captured image. The method may further include receiving a user input indicative of at least one value of at least one configurable criteria to be used in performing an objective assay evaluation includes receiving an end user input via a user interface.

The method may further include reading a subject identifier in the form of a piece of biometric information or a piece of government issued identification; and storing a logical association between the objective assay evaluation of the assay strip and the subject identifier.

At least one aspect may be summarized as a computer-readable medium that stores instructions that cause an assay system to perform assays of assay strips, by: receiving a user input indicative of at least one value of at least one configurable criteria to be used in performing an objective assay evaluation; receiving a number of assay strips in an interior of a housing; capturing at least one image a portion of the interior of the housing in which the assay strips are received; and computationally performing the objective assay evaluation for each of the assay strips in the captured image based at least in part on a representation of at least one signal line of each of the assay strips in the captured image and based at least in part on the user input indicative of the at least one value of at least one user configurable criteria.

Receiving a user input indicative of at least one value of at least one configurable criteria to be used in performing an objective assay evaluation may include receiving a user input indicative of a threshold level for the objective assay evaluation. Receiving a user input indicative of at least one value of at least one configurable criteria to be used in performing an objective assay evaluation may include receiving a user input indicative of a threshold intensity level for a positive results signal line. Receiving a user input indicative of at least one value of at least one configurable criteria to be used in performing an objective assay evaluation may include receiving a value indicative of a physical format of the assay strips of the respective type of assay strip. Receiving a user input indicative of at least one value of at least one configurable criteria to be used in performing an objective assay evaluation may include receiving a value indicative of a type of assay strip. Receiving a user input indicative of at least one value of at least one configurable criteria to be used in performing an objective assay evaluation may include receiving a value indicative of a assay strip manufacturer. Receiving a number of assay strips in an interior of a housing may include receiving a plurality of assay strips in the housing arranged such that at least a portion of each of a plurality of flow strips is exposed to an imager.

Capturing at least one image in the interior of the housing may include capturing at least one image of an area in the interior of the housing having a dimension that is greater than a dimension of a single assay strip. Capturing at least one image in the interior of the housing may include capturing at least one image of an area in the interior of the housing having a length and a width that is greater than a length and a width of at least two adjacent assay strips.

The instructions stored on the computer-readable may further cause a processor(s) to computationally identify individual ones of the assay strips in the captured image. Receiving a user input indicative of at least one value of at least one configurable criteria to be used in performing an objective assay evaluation may include receiving an end user input via a user interface.

An assay system to perform assays using assay strips may be summarized as including a housing having an interior and at least one entrance providing access to the interior, the at least one entrance sized to receive at least one container containing a specimen and an assay strip carrier that holds at least one assay strip; an imager subsystem operable to capture images of any of the assay strips received in the interior of the housing; and a processor subsystem comprising at least one processor and at least one processor-readable memory communicatively coupled to the at least one processor, the at least one processor also communicatively coupled to the imager subsystem to receive image information representative of the images captured by the imager subsystem, the at least one processor configured to identify individual ones of the assay strips in the image from the image information, the at least one processor further configured to perform an objective assay evaluation based at least in part on at least one signal line on each of the assay strips and based at least in part on at least one configurable criteria. The at least one processor may be further configured to store a respective high resolution digital representation of the captured image of each of at least some of the assay strips to a computer-readable storage medium along with at least some identification information logically associated with the respective high resolution digital representation of the captured image of each of the at least some of the assay strips. The at least one processor may be further configured to store a respective high resolution digital representation of the captured image of each of at least some of the assay strips to a computer-readable storage medium along with at least some information indicative of a result of the objective assay evaluation for each of at least some of the assay strips logically associated with the respective high resolution digital representation of the captured image of each of the at least some of the assay strips. The at least one processor may be configured to identify individual ones of the assay strips in the image from the image information, by a first iteration of pixel transformation based on a first color of a plurality of pixels; a first iteration of blob analysis on a set of the plurality of pixels resulting from the first iteration of pixel transformation to identify a first number of blobs; a first iteration of blob pairing on the first number of blobs identified in the first iteration of blob analysis; a second iteration of pixel transformation based on a second color of a plurality of pixels; a second iteration of blob analysis on a set of the plurality of pixels resulting from the second iteration of pixel transformation to identify a second number of blobs; and a second iteration of blob pairing on the second number of blobs identified in the second iteration of blob analysis. Additional iterations of pixel transformation based on additional colors of the plurality of pixels may be performed. The at least one processor may be further configured to identify any machine-readable symbols in the image from the image information, and to decode the identified machine-readable symbols, if any.

The assay system may further include a user interface including a number of user selectable inputs that correspond to respective ones of a number of configuration modes, where in response to selection of one of the user selectable inputs the processor subsystem may reconfigure the at least one configurable criteria. The user interface may include at least one input device configured to allow the entry of a subject identifier that uniquely identifies a subject from which a sample on the assay strip was taken, and wherein the at least one processor may be configured to store a logical association between the objective assay evaluation of the assay strip and the subject identifier. The user interface may include at least one input device configured to allow the entry of a selection that identifies a type of data carrier, and wherein the at least one processor may be configured to process based on the type of data carrier indicated by the entry. The image subsystem may include a two dimensional array that images an area greater than an area of a single assay strip.

A method of operating an assay system to perform assays of assay strips may be summarized as including receiving a container enclosing a specimen along with number of assay strips in an interior of a housing; capturing at least one high resolution image of a portion of the interior of the housing in which the assay strips are received; computationally identifying individual ones of the assay strips in the captured high resolution image; and computationally performing the objective assay evaluation for each of the identified individual ones of the assay strips that appear in the captured high resolution image based at least in part on a representation of at least one signal line of each of the assay strips in the captured high resolution image. Capturing at least one high resolution image in the interior of the housing may include capturing at least one high resolution image of an area in the interior of the housing having a length and a width that is greater than a length and a width of at least two adjacent assay strips. Computationally identifying individual ones of the assay strips in the captured high resolution image may include performing a first iteration of pixel transformation based on a first color of a plurality of pixels in the high resolution image; performing a first iteration of blob analysis on a of the plurality of pixels resulting from the first iteration of pixel transformation to identify a first number of blobs; performing a first iteration of blob pairing on the first number of blobs identified in the first iteration of blob analysis; performing a second iteration of pixel transformation based on a second color of a plurality of pixels; performing a second iteration of blob analysis on a of the plurality of pixels resulting from the second iteration of pixel transformation to identify a second number of blobs; and performing a second iteration of blob pairing on the second number of blobs identified in the second iteration of blob analysis.

The method may further include identifying any machine-readable symbols in the captured high resolution image; decoding the identified machine-readable symbols, if any; and logically associating identification information decoded from the identified machine readable symbols with respective ones of the assay strips which appear in the high resolution image.

The method may further include storing a respective digital representation of a portion of the captured high resolution image of each of at least some of the assay strips to a computer-readable storage medium along with at least some identification information logically associated with the respective digital representation of the respective portion of the captured high resolution image of each of the at least some of the assay strips.

The method may further include storing a respective digital representation of a portion of the captured high resolution image of each of at least some of the assay strips to a computer-readable storage medium along with at least some information indicative of a result of the objective assay evaluation for each of at least some of the assay strips logically associated with the respective digital representation of the respective portion of the captured high resolution image of each of the at least some of the assay strips.

The method may further include reading a subject identifier in the form of a piece of biometric information or a piece of government issued identification; and storing a logical association between the objective assay evaluation of the assay strip and the subject identifier.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 22 is a screen print showing a results screen of a user interface of an assay device for an assay strip having a positive result, according to on illustrated embodiment.

FIG. 26 is a screen print showing a first instructions screen of a user interface of an assay device, according to another illustrated embodiment.

FIG. 30 is a screen print showing a fifth instructions screen of a user interface of an assay device, according to one illustrated embodiment.

FIG. 37 is a schematic diagram of a report generated by assay system according to one illustrated embodiment, the report including identification information, a summary of assay results, a detailed listing of assay results and an image of assay strip(s) in a specimen holder used to test for multiple banned substances from a single specimen.

DETAILED DESCRIPTION

Figure 1:
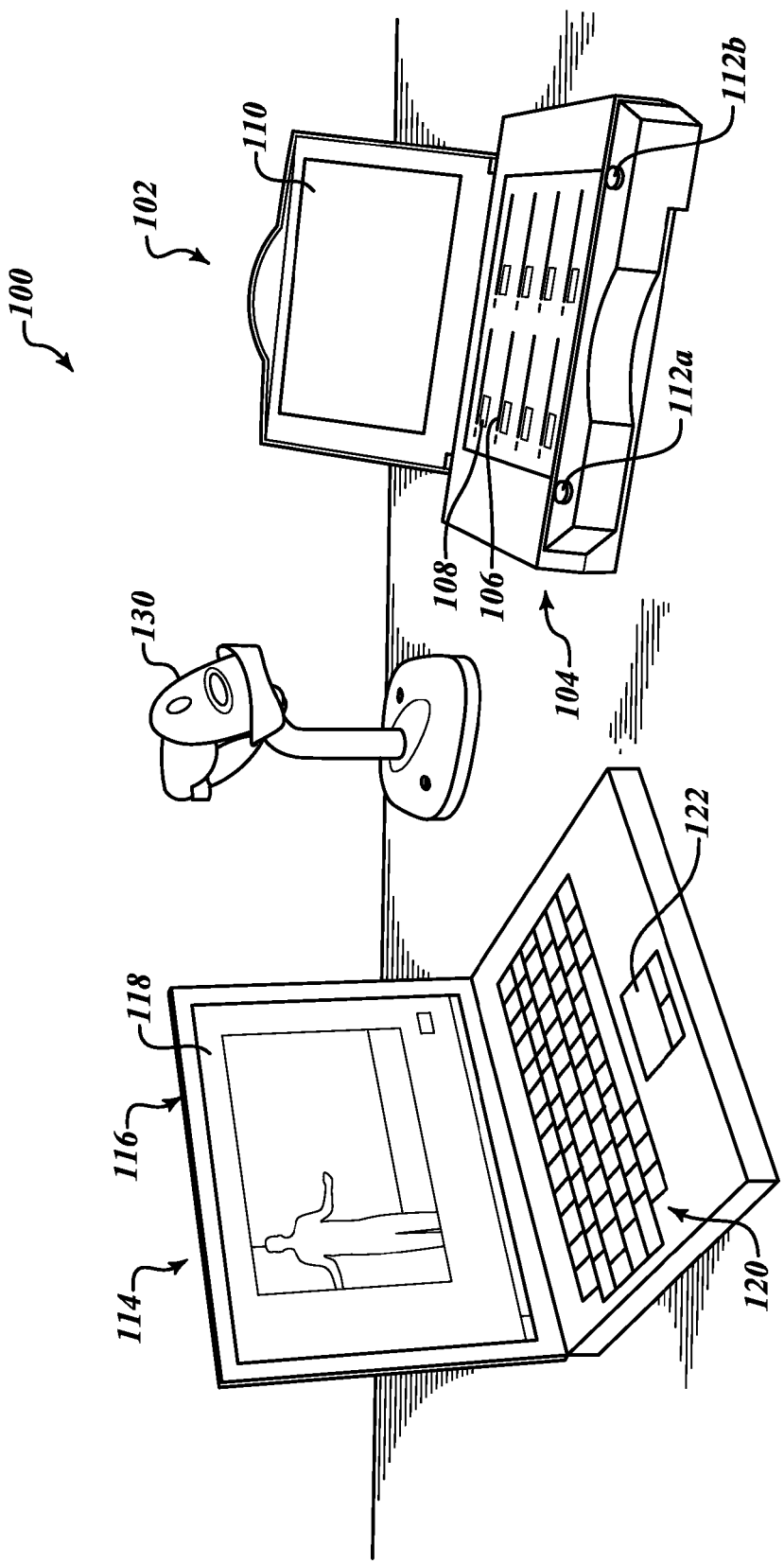
FIG. 1 is an isometric view of an assay system to perform assays, including an assay device, a computing system, and a barcode reader, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with apparatuses, methods and articles for performing assays using lateral flow strips have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

This disclosure describes various systems, methods and articles related to performing assays on various assay media. Many embodiments are capable of providing actual quantitative analysis, providing uniform results and reducing errors. Many embodiments are capable of handling multiple pieces of assay media, which may advantageously increase throughput. Many embodiments are capable of handling assay media without cumbersome carriers, such as cartridges, frames or holders. Many embodiments are capable of handling assay media of different formats, for example assay media from different manufacturers or different product lines of a given manufacturer. Many embodiments are capable of providing an intuitive graphical user interface, which can lead a user through the various steps associated with performing a given assay. Such may be based on a given configuration, which may in turn be based on a given type of assay medium or assay being performed. Such may also be easily reconfigurable, allowing a single assay system to handle many different types of assays, and reducing the need for highly skilled personnel.

These and other advantages may be realized via the various embodiments described herein.

FIG. 1 shows an assay system 100 according to one illustrated embodiment.

The assay system 100 includes an assay device 102 configured to perform assays or assay evaluations on assay strips. The assay device 102 may include a housing 104 including one or more slots 106 (only one called out in FIG. 1) sized to receive at least one assay strip therein. The assay strips may advantageously be received directly in the slots, without the need from cartridges, receivers, frames, holders or other cumbersome assay strip carrier structures. The slots 106 provide access to an interior of the housing 104. Each of the slots 106 may be identified or labeled with a respective machine-readable symbol 108 (only one called out in FIG. 1) which allows automatic identification of the slot 106 via machine reading. Such machine-readable symbols 108 may take the form of barcode symbols, matrix or area code symbols, or stacked code symbols. The assay device 102 may further include one or more displays 110 on which instructions, data, information and or a portion of a user interface (e.g., user selectable icons, pull-down menus, dialog boxes, fields, etc.) may be selectively displayed. The assay device 102 may include one or more user input devices, for example, a scan start button 112a and a scan stop button 112b. The scan start and stop buttons 112a, 112b may be used to start and stop scans when not under automatic control or under control from the graphical user interface.

The assay system 100 may also include one or more peripheral computing systems 114 communicatively coupled to the assay device 102. The computing system 114 may take a variety of forms including desktop or laptop personal computers, workstations, mini computers, mainframe computers, server or client computers. The computing system 114 may include a user input subsystem 116 which may include a display 118, keyboard or keypad 120, pointing device such as track pad 122, joystick, trackball, etc., as well as user-selectable icons. The computing system 114 may be communicatively coupled to the assay device 102 via a wired or wireless connection, which may, for example take the form of a local area network (LAN) or wide area network (WAN).

The assay system 100 may optionally include a stand-alone reader 130 communicatively coupled to the assay device 102 and/or peripheral computing system 114. The reader 130 may take a variety of forms including a scanner employing focus light or an imager employing flood illumination or ambient light. The reader 130 may take the form of any commercially available machine-readable symbol reader such as those available from Intermec Technologies of Everett, Wash. The machine-readable symbol reader may be configured to read machine-readable symbols encoded in one or more machine-readable symbologies (e.g., Code 93i, Code 39, Datamatrix code, UPC/EAN, etc.). The assay system 100 may employ other automatic data collection devices as readers, for example magnetic stripe readers, radio frequency identification readers or interrogators, etc.

Figure 2:
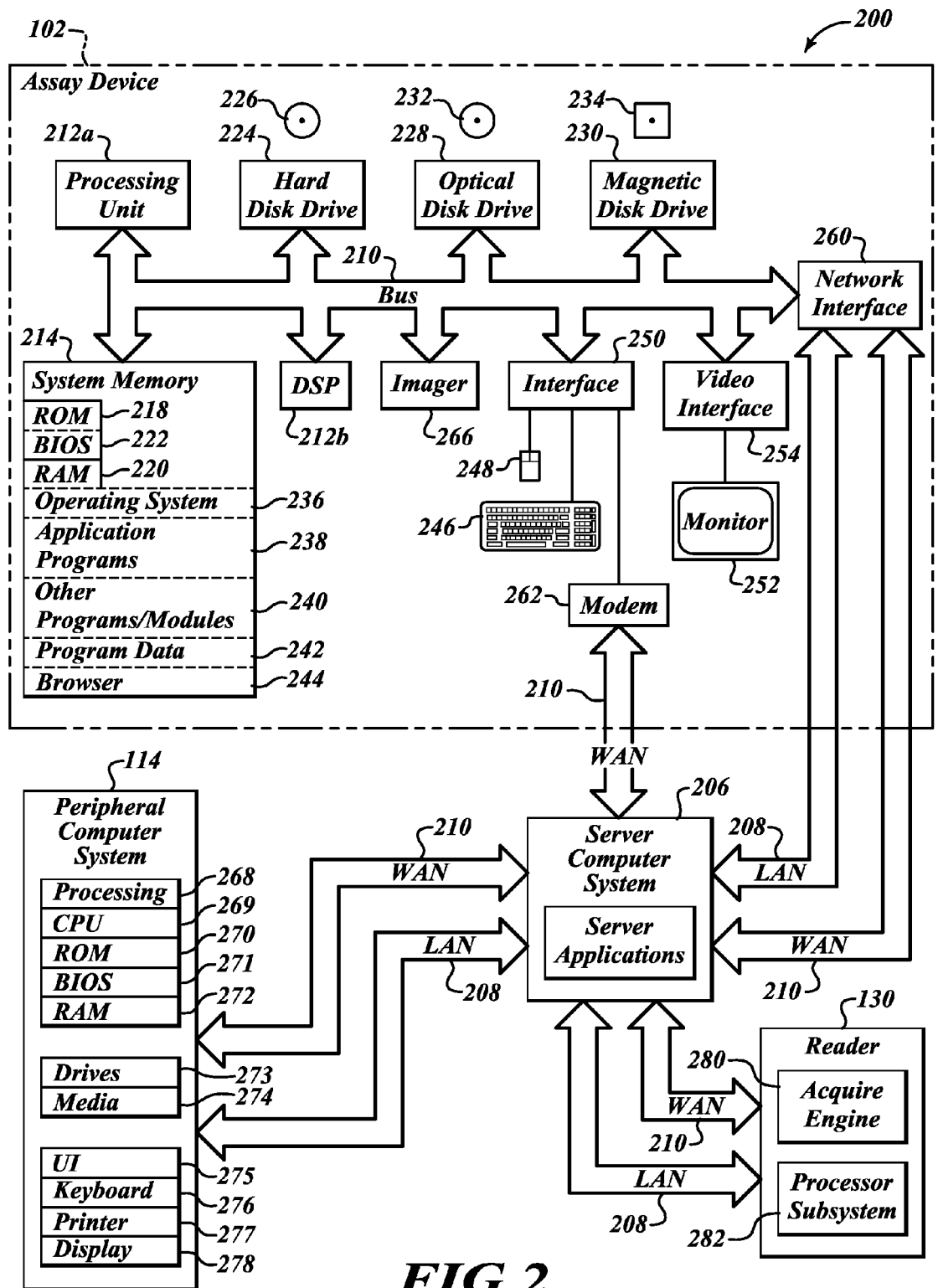
FIG. 2 is a functional block diagram of an assay system including an assay device, peripheral computing system, symbol reader, and a server computing system providing communications therebetween, according to another illustrated embodiment.

FIG. 2 and the following discussion provide a brief, general description of a suitable assay system environment 200 in which the various illustrated embodiments can be implemented. Although not required, the embodiments will be described in the general context of computer-executable instructions, such as program application modules, objects, or macros stored on computer- or processor readable-media and executed by a computer or processor. Those skilled in the relevant art will appreciate that the illustrated embodiments as well as other embodiments can be practiced with other assay system configurations and/or other computing system configurations, including hand-held devices, multiprocessor systems, microprocessor-based or programmable consumer electronics, personal computers ("PCs"), network PCs, mini computers, mainframe computers, and the like. The embodiments can be practiced in distributed computing environments where tasks or modules are performed by remote processing devices, which are linked through a communications network. In a distributed computing environment, program modules may be located in both local and remote memory storage devices.

FIG. 2 shows an assay system environment 200 comprising one or more assay devices 102, peripheral computing systems 114, readers 130 and optionally one or more server computing systems 206 coupled by one or more communications channels, for example one or more local area networks (LANs) 208 or wide area networks (WANs) 210. The assay system 200 may employ other computers, such as conventional personal computers, where the size or scale of the system allows.

The assay device 102 may include one or more processing units 212a, 212b (collectively 212), system memory 214 and a system bus 216 that couples various system components including the system memory 214 to the processing units 212. The assay device 102 will at times be referred to in the singular herein, but this is not intended to limit the embodiments to a single assay device since in typical embodiments, there may be more than one assay device or other device involved. The processing units 212 may be any logic processing unit, such as one or more central processing units (CPUs) 212a, digital signal processors (DSPs) 212b, application-specific integrated circuits (ASICs), field programmable gate arrays (FPGAs), etc. Unless described otherwise, the construction and operation of the various blocks shown in FIG. 2 are of conventional design. As a result, such blocks need not be described in further detail herein, as they will be understood by those skilled in the relevant art.

The system bus 216 can employ any known bus structures or architectures, including a memory bus with memory controller, a peripheral bus, and a local bus. The system memory 214 includes read-only memory ("ROM") 218 and random access memory ("RAM") 220. A basic input/output system ("BIOS") 222, which can form part of the ROM 218, contains basic routines that help transfer information between elements within the assay device 102, such as during start-up.

The assay device 102 may include a hard disk drive 224 for reading from and writing to a hard disk 226, optical disk drive 228 for reading from and writing to removable optical disks 232, and/or a magnetic disk drive 230 for reading from and writing to magnetic disks 234. The optical disk 232 can be a CD-ROM, while the magnetic disk 234 can be a magnetic floppy disk or diskette. The hard disk drive 224, optical disk drive 228 and magnetic disk drive 230 may communicate with the processing unit 212 via the system bus 216. The hard disk drive 224, optical disk drive 228 and magnetic disk drive 230 may include interfaces or controllers (not shown) coupled between such drives and the system bus 216, as is known by those skilled in the relevant art. The drives 224, 228 and 230, and their associated computer-readable media 226, 232, 234, provide nonvolatile storage of computer readable instructions, data structures, program modules and other data for the assay device 102. Although the depicted assay device 102 is illustrated employing a hard disk 224, optical disk 228 and magnetic disk 230, those skilled in the relevant art will appreciate that other types of computer-readable media that can store data accessible by a computer may be employed, such as magnetic cassettes, flash memory cards, digital video disks ("DVD"), Bernoulli cartridges, RAMs, ROMs, smart cards, etc.

Program modules can be stored in the system memory 214, such as an operating system 236, one or more application programs 238, other programs or modules 240 and program data 242. Program modules may include instructions for handling security such as password or other access protection and communications encryption. The system memory 214 may also include communications programs for example a Web client or browser 244 for permitting the assay device 102 to access and exchange data with sources such as Web sites of the Internet, corporate intranets, extranets, or other networks as described below, as well as other server applications on server computing systems such as those discussed further below. The browser 244 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document. A number of Web clients or browsers are commercially available such as those from America Online and Microsoft of Redmond, Wash.

While shown in FIG. 2 as being stored in the system memory 214, the operating system 236, application programs 238, other programs/modules 240, program data 242 and browser 244 can be stored on the hard disk 226 of the hard disk drive 224, the optical disk 232 of the optical disk drive 228 and/or the magnetic disk 234 of the magnetic disk drive 230.

An operator can enter commands and information into the assay device 102 through input devices such as a touch screen or keyboard 246 and/or a pointing device such as a mouse 248 and graphical user interface. Other input devices can include a microphone, joystick, game pad, tablet, scanner, etc. These and other input devices are connected to one or more of the processing units 212 through an interface 250 such as a serial port interface that couples to the system bus 216, although other interfaces such as a parallel port, a game port or a wireless interface or a universal serial bus ("USB") can be used. A monitor 252 or other display device is coupled to the system bus 216 via a video interface 254, such as a video adapter. The assay device 102 can include other output devices, such as speakers, printers, etc.

The assay device 102 includes one or more imagers 266, operable to capture high resolution images of assay strips received when received in the slots 106 (FIG. 1) of the assay device. The imager 266 may take a variety of forms, for example one- or two-dimensional arrays of charged coupled devices, CMOS sensors, digital still cameras, digital video cameras, analog video cameras with frame grabbers, etc. For example, the imager 266 may include an illumination source to illuminate the assay strips. The illumination source may, for example, take the form of one or more lamps, for instance one or more fluorescent lamps which may advantageously eliminate or reduce the need for hardware filters or software filters. Various specific embodiments of imagers 266 are discuss below with reference to FIGS. 3-5. A buffer (not shown) may buffer data from the imager 266 until the DSP 212b is ready to process the image data.

The assay device 102 can operate in a networked environment using logical connections to one or more remote computers and/or devices, for example the server computing system 206. The server computing system 206 can be another personal computer, a server, another type of computer, or a collection of more than one computer communicatively linked together and typically includes many or all of the elements described above for the assay device 102. The server computing system 206 is logically connected to one or more of the assay devices 102 under any known method of permitting computers to communicate, such as through one or more LANs 208 and/or WANs 210 such as the Internet. Such networking environments are well known in wired and wireless enterprise-wide computer networks, intranets, extranets, and the Internet. Other embodiments include other types of communication networks including telecommunications networks, cellular networks, paging networks, and other mobile networks.

When used in a LAN networking environment, the assay device 102 is connected to the LAN 208 through an adapter or network interface 260 (communicatively linked to the system bus 216). When used in a WAN networking environment, the assay device 102 may include a modem 262 or other device, such as the network interface 260, for establishing communications over the WAN 210. The modem 262 is shown in FIG. 2 as communicatively linked between the interface 250 and the WAN 210. In a networked environment, program modules, application programs, or data, or portions thereof, can be stored in the server computing system 206. In the depicted embodiment, the assay device 102 is communicatively linked to the server computing system 206 through the LANs 208 and/or WAN 210, for example with TCP/IP middle layer network protocols. However, other similar network protocol layers are used in other embodiments, such as User Datagram Protocol ("UDP"). Those skilled in the relevant art will readily recognize that the network connections shown in FIG. 2 are only some examples of establishing communication links between computers, and other links may be used, including wireless links.

The server computing system 206 is also communicatively linked to one or more other computing systems or devices, such as the peripheral computing system 114 and/or reader 130, typically through the LAN 208 or the WAN 210 or other networking configuration such as a direct asynchronous connection (not shown).

The server computing system 206 includes server applications 264 for the routing of instructions, programs, data and agents between the assay device 102, peripheral computing system 114 and/or reader 130. For example the server applications 264 may include conventional server applications such as WINDOWS NT 4.0 Server, and/or WINDOWS 2000 Server, available from Microsoft Corporation or Redmond, Wash. Additionally, or alternatively, the server applications 264 can include any of a number of commercially available Web servers, such as INTERNET INFORMATION SERVICE from Microsoft Corporation and/or IPLANET from Netscape.

The peripheral computing system 114 may take the form of a conventional mainframe computer, mini-computer, workstation computer, personal computer (desktop or laptop), or handheld computer. The computing system 114 may include a processing unit 268, a system memory 269 and a system bus (not shown) that couples various system components including the system memory 269 to the processing unit 268. The peripheral computing system 114 will at times be referred to in the singular herein, but this is not intended to limit the embodiments to a single peripheral computing system 114 since in typical embodiments, there may be more than one peripheral computing system 114 or other device involved. Non-limiting examples of commercially available systems include, but are not limited to, an 80x86 or Pentium series microprocessor from Intel Corporation, U.S.A., a PowerPC microprocessor from IBM, a Sparc microprocessor from Sun Microsystems, Inc., a PA-RISC series microprocessor from Hewlett-Packard Company, or a 68xxx series microprocessor from Motorola Corporation.

The processing unit 268 may be any logic processing unit, such as one or more central processing units (CPUs), digital signal processors (DSPs), application-specific integrated circuits (ASICs), field programmable gate arrays (FPGAs), etc. Unless described otherwise, the construction and operation of the various blocks of the peripheral computing system 114 shown in FIG. 2 are of conventional design. As a result, such blocks need not be described in further detail herein, as they will be understood by those skilled in the relevant art.

The system bus can employ any known bus structures or architectures, including a memory bus with memory controller, a peripheral bus, and a local bus. The system memory 269 includes read-only memory ("ROM") 270 and random access memory ("RAM") 272. A basic input/output system ("BIOS") 271, which can form part of the ROM 270, contains basic routines that help transfer information between elements within the peripheral computing system 114, such as during start-up.

The peripheral computing system 114 also includes one or more media drives 273 (e.g., a hard disk drive, magnetic disk drive, and/or optical disk drive) for reading from and writing to computer-readable storage media 274 (e.g., hard disk, optical disks, and/or magnetic disks). The computer-readable storage media 274 may, for example, take the form of removable media. For example, hard disks may take the form of a Winchester drives, optical disks can take the form of CD-ROMs, while magnetic disks can take the form of magnetic floppy disks or diskettes. The media drive(s) 273 communicate with the processing unit 268 via one or more system buses. The media drives 273 may include interfaces or controllers (not shown) coupled between such drives and the system bus, as is known by those skilled in the relevant art. The media drives 273, and their associated computer-readable storage media 274, provide nonvolatile storage of computer readable instructions, data structures, program modules and other data for the peripheral computing system 114. Although described as employing computer-readable storage media 274 such as hard disks, optical disks and magnetic disks, those skilled in the relevant art will appreciate that peripheral computing system 114 may employ other types of computer-readable storage media that can store data accessible by a computer may be employed, such as magnetic cassettes, flash memory cards, digital video disks ("DVD"), Bernoulli cartridges, RAMs, ROMs, smart cards, etc. Data or information, for example, high resolution images or image data, identification information, results of assays, etc., can be stored in the computer-readable storage media 274.

Program modules, such as an operating system, one or more application programs, other programs or modules and program data, can be stored in the system memory 269. Program may include instructions for handling security such as password or other access protection and communications encryption. The system memory 269 may also include communications programs for example a Web client or browser that permits the peripheral computing system 114 to access and exchange data with sources such as Web sites of the Internet, corporate intranets, extranets, or other networks as described below, as well as other server applications on server computing systems such as those discussed further below. The browser may, for example be markup language based, such as Hypertext Markup Language (HTML), Extensible Markup Language (XML) or Wireless Markup Language (WML), and may operate with markup languages that use syntactically delimited characters added to the data of a document to represent the structure of the document.

While described as being stored in the system memory 269, the operating system, application programs, other programs/modules, program data and/or browser can be stored on the computer-readable storage media 274 of the media drive(s) 273. An operator can enter commands and information into the peripheral computing system 114 via a user interface 275 through input devices such as a touch screen or keyboard 276 and/or a pointing device 277 such as a mouse. Other input devices can include a microphone, joystick, game pad, tablet, scanner, etc. These and other input devices are connected to the processing unit 269 through an interface such as a serial port interface that couples to the system bus, although other interfaces such as a parallel port, a game port or a wireless interface or a universal serial bus ("USB") can be used. A display or monitor 278 may be coupled to the system bus via a video interface, such as a video adapter. The peripheral computing system 114 can include other output devices, such as speakers, printers, etc.

The peripheral computing system 114 can operate in a networked environment using logical connections to one or more remote computers and/or devices, for example the server computing system 206.

The reader 130 may include one or more components operable to read machine-readable information carried by various articles.

The reader 130 may take the form of a machine-readable symbol reader configured to optically (e.g., visible, infrared, ultraviolet wavelengths of electromagnetic energy) read information encoded in machine-readable symbols (e.g., barcode symbols, stacked code symbols, area or matrix code symbols) carried by various articles. In such an embodiment, the reader 130 includes an information acquisition component or engine 280 to optically acquire the machine-readable symbol. Such may, for example, take the form of a scan engine that scans machine-readable symbols using a narrow beam of light (e.g., laser scanner). Alternatively, such may take the form of an image based reader that acquires images using floodlighting or ambient light. The reader 130 may be capable of capturing an image of a larger area encompassing a number of assay strips (e.g., eight strips). This can advantageously allow higher throughput as compared to conventional systems.

The reader 130 may also include a processor subsystem 282 configured to preprocess or process the optically acquire information. For instance, the processor subsystem 282 may be configured to decode information encoded in the machine-readable symbol, and may even determine which symbology to use in decoding machine-readable symbols encoded using a variety of different machine-readable symbologies (Code 39, Code 93i, DataMatrix, UPC/EAN). The processor subsystem 282 may include one or more processors (e.g., microprocessors, DSPs, ASICs, FPGAs), and memory (spinning media or solid-state media such as RAM, ROM, and FLASH media). The processor subsystem 282 may be an integral component of the reader 130 or may be a distinct dedicated component. Alternatively, the processing may be handled by another component, for instance the peripheral computing system 114 or assay device 102. A variety of suitable machine-readable symbol readers are commercially available, for example, from Intermec Technologies and Symbol Technologies.

The reader 130 may take the form of one or more magnetic stripe readers operable to information magnetically encoded in one or more magnetic stripes carried by various articles. In such an embodiment, the reader 130 includes an information acquisition component or engine 280 to magnetically acquired information encoded in the magnetic stripe.

Such an embodiment may also include a processor subsystem 282 configured to preprocess or process the magnetically acquired information. For instance, the processor subsystem 282 may be configured to decode information encoded in the magnetic stripe, and may even decode information encoded using a variety of specifications or formats. The processor subsystem 282 may include one or more processors (e.g., microprocessors, DSPs, ASICs, FPGAs), and memory (spinning media or solid-state media such as RAM, ROM, FLASH). The processor subsystem 282 may be an integral component of the reader 130 or may be a distinct dedicated component. Alternatively, the processing may be handled by another component, for instance the peripheral computing system 114 or assay device 102. Suitable magnetic stripe readers are commercially available from a variety of sources.

The reader 130 may take the form of one or more RFID readers or interrogators operable to wirelessly read information encoded into one or more RFID transponder (e.g., tags). In such an embodiment, the reader 1230 includes an information acquisition component or engine 208 to wirelessly (e.g., RF or microwave wavelengths of electromagnetic energy) interrogate an RFID transponder and to receive information encoded in a response from the RFID transponder.

Such an embodiment may also include a processor subsystem 282 configured to preprocess or process the wirelessly acquired information. For instance, the processor subsystem 282 may be configured to decode information encoded in the RFID transponder's response, and may even decode information encoded using a variety of specifications or formats. The processor subsystem 282 may include one or more processors (e.g., microprocessors, DSPs, ASICs, FPGAs), and memory (spinning media or solid-state media such as RAM, ROM, FLASH). The processor subsystem 282 may be an integral component of the reader 130 or may be a distinct dedicated component. Alternatively, the processing may be handled by another component, for instance the peripheral computing system 114 or assay device 102. Suitable RFID interrogators or readers are commercially available from a variety of sources including Symbol Technologies and Intermec Technologies.

The reader 130 may be used to read machine-readable information carried by assay strips, test tubes, cuvettes, cups, plates, wells, trays, or carried on the assay device (e.g., machine-readable symbols 108 marking respective slots 106, illustrated in FIG. 1). The machine-readable information may be carried by a tag or label which is adhered or otherwise attached to the article. Alternatively, the machine-readable information may be printed, engraved, etched, or otherwise applied to the article itself, without the use of a tag or label. The machine-readable information may include unique identification information (e.g., alphanumeric serial number, etc.), which uniquely identifies the article.

Figure 3:
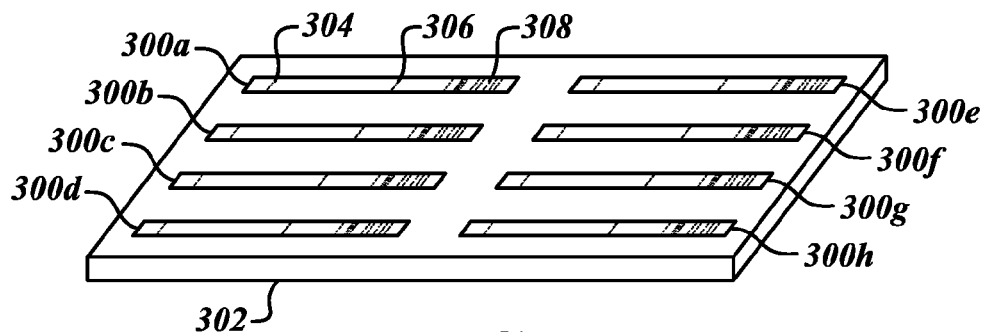
FIG. 3 is an isometric diagram of a number of test strips positioned to be read by an imager in the form of a two-dimensional imager array, according to one illustrated embodiment.

FIG. 3 shows a number of assay strips 300a-300h (collectively 300) positioned relative to an imager 302 to capture high resolution images of the assay strips 300, according to one illustrated embodiment. The assay strips 300 may include a positive test result signal line 304 (only one called out in FIG. 3) and a control signal line 306 (only one called out in FIG. 3). The positive test result signal line 304 provides a visible indication of the presence of an analyte or some other substance. The control signal line 306 provides a visible indication that the assay strip 300 is functioning correctly. The assay strip 300 may also include one or more machine-readable symbols 308 (only one called out in FIG. 3) which may encode identification information that uniquely identifies the assay strip 300 over some large set of assay strips. The machine-readable symbol 308 may, for example, take the form of a barcode symbol. Alternatively, other structures to associate identification information with the assay strip 300 may be employed, for example, RFID tags or magnetic stripes.

The imager 302 may take the form of a two-dimensional image device, for instance, a two-dimensional array of charge coupled devices (CCDs) or CMOS devices. Consequently, the imager 302 may capture an image of an area that is larger than an area of a single assay strip 300. Typically, the imager 302 captures a high resolution image of an area greater than two assay strips 300, for example eight assay strips 300.

Figure 4:
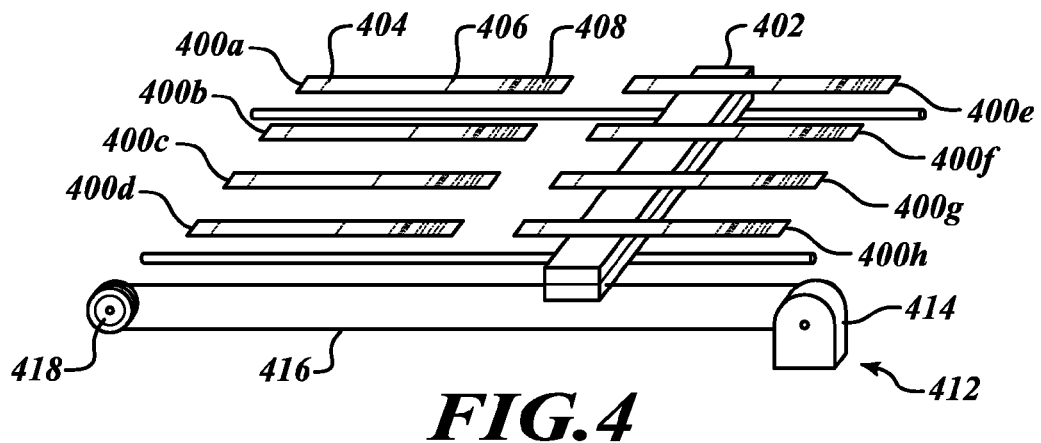
FIG. 4 is an isometric diagram of a number of test strips positioned to be read by a one-dimensional imager, driven by a motor to move with respect to the test strips, according to one illustrated embodiment.

FIG. 4 shows a plurality of assay strips 400a-400h (collectively 400) positioned to be imaged by an imager 402 according to another illustrated embodiment. The assay strips 400 include a positive result signal line 404 (only one called out in FIG. 4), a control signal line 406 (only one called out in FIG. 4) and a unique identifier 408. The imager 402 may take the form of a one-dimensional image capture device, for example, a one-dimensional array of CCDs. The imager 402 is mounted for movement relative to the assay strips 400. For example, the imager 402 may be mounted for translation along rails 410a, 410b. Alternatively, the imager 402 may be mounted for rotation or pivoting with respect to the assay strips 400. A drive system 412 may be coupled to move the imager 402 relative to the assay strips 400. The drive system 412 may include one or more actuators, for example, a motor 414 which in some embodiments may take the form of a stepper motor. The motor 414 may be coupled to one or more processors 212 (FIG. 2) to receive drive signals therefrom. The motor 414 may drive one or more linkages, for example, a belt 416 and pulley 418 to cause movement of the imager 402 to image an area larger than a single assay strip 400, for example an area occupied by eight assay strips. Other drive mechanisms may be employed.

Figure 5:
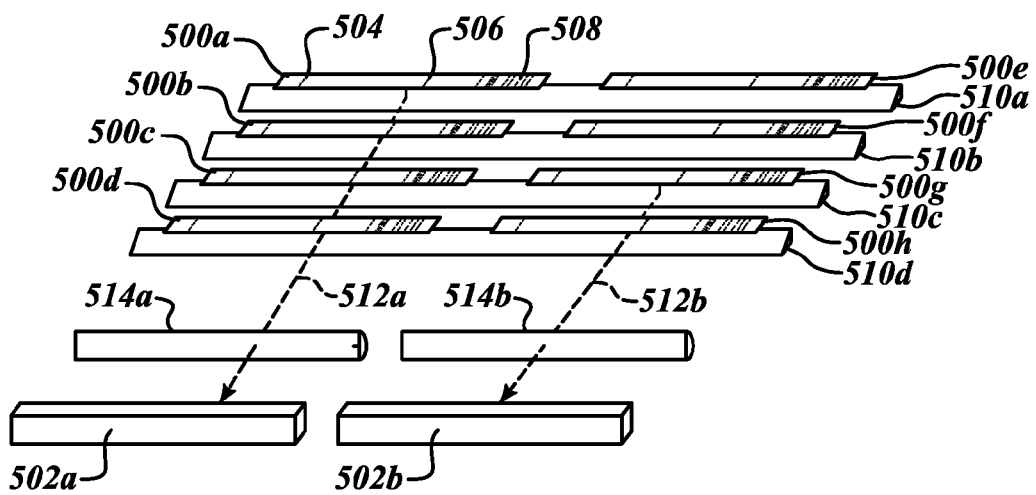
FIG. 5 is an isometric diagram of a number of test strips positioned to be read by a number of imagers that employs mirrors or prisms and lenses according to another illustrated embodiment.

FIG. 5 shows a plurality of assay strips 500a-500h (collectively 500) positioned to be read by imagers 502a, 502b (collectively 500), according to another illustrated embodiment. As noted before, the assay strips 500 include a positive result signal line 504 (only one called out in FIG. 5), a control signal line 506 (only one called out in FIG. 5) and a machine-readable identifier 508 (only one called out in FIG. 5). The imagers 502a, 502b may take a variety of forms including one- or two-dimensional arrays of charge-coupled devices, or CMOS image sensors. One or more mirrors or prisms 510a-510d (collectively 510) may be positioned to reflect or refract an image of the assay strips 500 toward the imager devices 502 as illustrated by image paths 512a, 512b (collectively 512). One or more lenses 514a, 514b (collectively 514) may be interposed in the image paths 512 to focus the images of the assay strips 500 onto the image devices 502. The lenses 514 may take a variety of forms including optical lenses of glass, acrylic or plastic, adjustable lenses including mechanically adjustable lenses or fluid lenses. The lenses 514 may, for example, take the form of cylindrical lenses. One or more mechanical apertures may also be employed. The imagers 502 are capable of imaging an area greater than an area of a single assay strip, for example an array that encompasses eight assay strips.

The various imagers discussed above can take a variety of forms. For example, the imagers may be CCDs or CMOS based, may be one- or two-dimensional arrays, may be black and white, gray-scale or color devices, may be digital still cameras, digital video cameras, analog still cameras, analog video cameras, board imagers, etc. Imagers may include frame grabbers, may couple to frame grabbers and may operate without the need for a frame grabber. Suitable imagers are commercially available in a large variety of forms from a large variety of suppliers.

Figure 6:
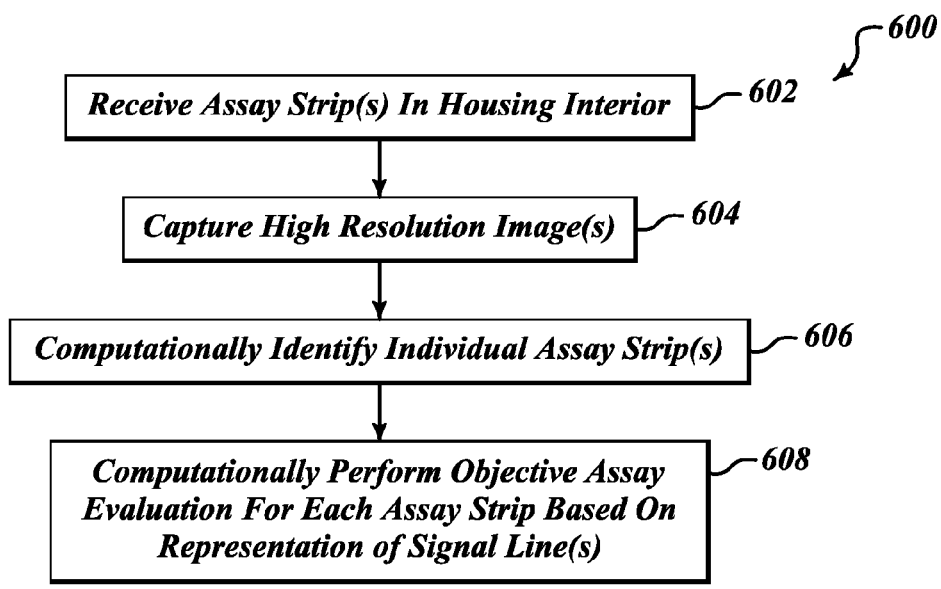
FIG. 6 is a flow diagram of a method of operating an assay system according to one illustrated embodiment including receiving assay strips, capturing high resolution images, computationally identifying individual strips, and computationally performing objective assay evaluations.

FIG. 6 shows a method 600 of operating an assay system according to one illustrated embodiment.

At 602, assay strips are received in an interior of the housing of an assay device, for example, via one or more slots. The assay strips may advantageously be received directly in the slots, without the need for a cartridge, frame, receiver, holder or other cumbersome assay strip carrier. Alternatively, the assay device may include a cover which is moveable between an open position in which access to the interior is provided and a closed position in which access to the interior is blocked. In the closed position, the cover may provide a barrier to ambient light, controlling the internal environment to enhance image capture or acquisition. The cover may, for example, be pivoted between the open and closed positions, similar to that commonly used in flat bed scanners.

At 604, one or more imagers captures a high resolution image of at least a portion of the assay strips received in the housing. The imager(s) may capture or otherwise acquire an image of an area larger than an area of a single assay strip. For example, the imager(s) may capture a high resolution image of an area that encompasses multiple assay strips, for instance eight assay strips. The imager(s) may take the form of a flat bed imager. The number of assay strips may not be known to the assay device before the high resolution image is captured, so long as an image of a sufficiently large area is captured or otherwise acquired.

At 606, a processor computationally identifies individual assay strips in the high resolution image. The processor may employ a variety of machine-vision or image processing techniques to identify individual assay strips in the high resolution image. In some embodiments, the processor may employ approximate positions in the image to locate the individual assay strips, for example where the slots cause the assay strips to be positioned in relatively fixed locations with respect to the imager(s). In other embodiments, the processor identifies the assay strips in the image without any reference to approximate positions. This may be particularly useful where the imager is a flat bed scanner, and assay strips may be positioned at widely divergent positions between successive runs.

At 608, the processing system computationally performs an objective assay evaluation for each assay strip based on a representation of one or more signal lines (e.g., positive test results, control) in the captured high resolution image. For example, the processing system may determine a magnitude of a positive test results signal line and compare the determined magnitude to a threshold value. Also for example, the processing system may determine whether a control signal line is present, indicating a positive result only where the control signal line is present and the magnitude of the positive test result signal line exceeds the threshold value. The presence of a control signal line typically indicates that the test has been completed successfully, thereby validating the result. Given a positive control signal line, the absence of a test signal line indicates a negative result. Given a positive control signal line, the presence of a test signal line indicates a positive result. The processing system may subtract out one or more background colors and/or perform other image processing to enhance or produce uniform results.

Figure 7:
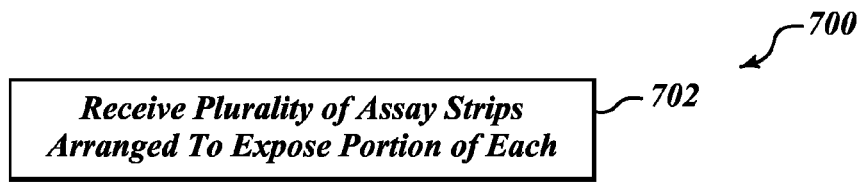
FIG. 7 is a flow diagram showing a method of receiving assay strips, according to one illustrated embodiment.

FIG. 7 shows a method 700 of receiving assay strips, according to one illustrated embodiment.

At 702, a plurality of assay strips are received in the interior of the housing arranged to expose a portion of each of the assay strips to the imager. Such allows the imager to capture high resolution images of at least a portion of each of the assay strips. While each assay strip may be fully exposed to the imager(s), some embodiments may expose only a longitudinal portion of each assay strip (e.g., assay strips in a column partially overlap one another) so long as a sufficient portion of each assay strip is exposed to perform the analysis. Such may allow a reduction in form factor for the assay device, for example allow production of a handheld device capable of analyzing multiple assay strips in a single run. As previously noted, the assay strips may be received via one or more slots, or may be received when a cover is in an open position, for instance laid out on an at least partially transparent plate (e.g., glass or acrylic).

Figure 8:
FIG. 8 is a flow diagram showing a method of capturing an image of assay strips, according to one illustrated embodiment.

FIG. 8 shows a method 800 of capturing high resolution images, according to one illustrated embodiment.

At 802, one or more imagers captures a high resolution image of an area with a dimension greater than the dimension of a single assay strip. Thus, for example, the imager may capture an image of two or more assay strips simultaneously or concurrently, for instance an area encompassing eight assay strips. This may facilitate increased throughput, allowing multiple assay strips to be processed in a single run.

Figure 9:
FIG. 9 is a flow diagram showing a method of capturing images of assay strips according to another illustrated embodiment.

FIG. 9 shows a method 900 of capturing high resolution images according to another illustrated embodiment.

At 902, the imager(s) captures an image of an area with a length and width that is greater than a length and width of at least two adjacent assay strips. Thus, for example, the imager(s) may capture an image containing portions of two or more assay strips simultaneously or concurrently, for instance an area encompassing eight assay strips. This may facilitate increased throughput, allowing multiple assay strips to be processed in a single run.

Figure 10A:
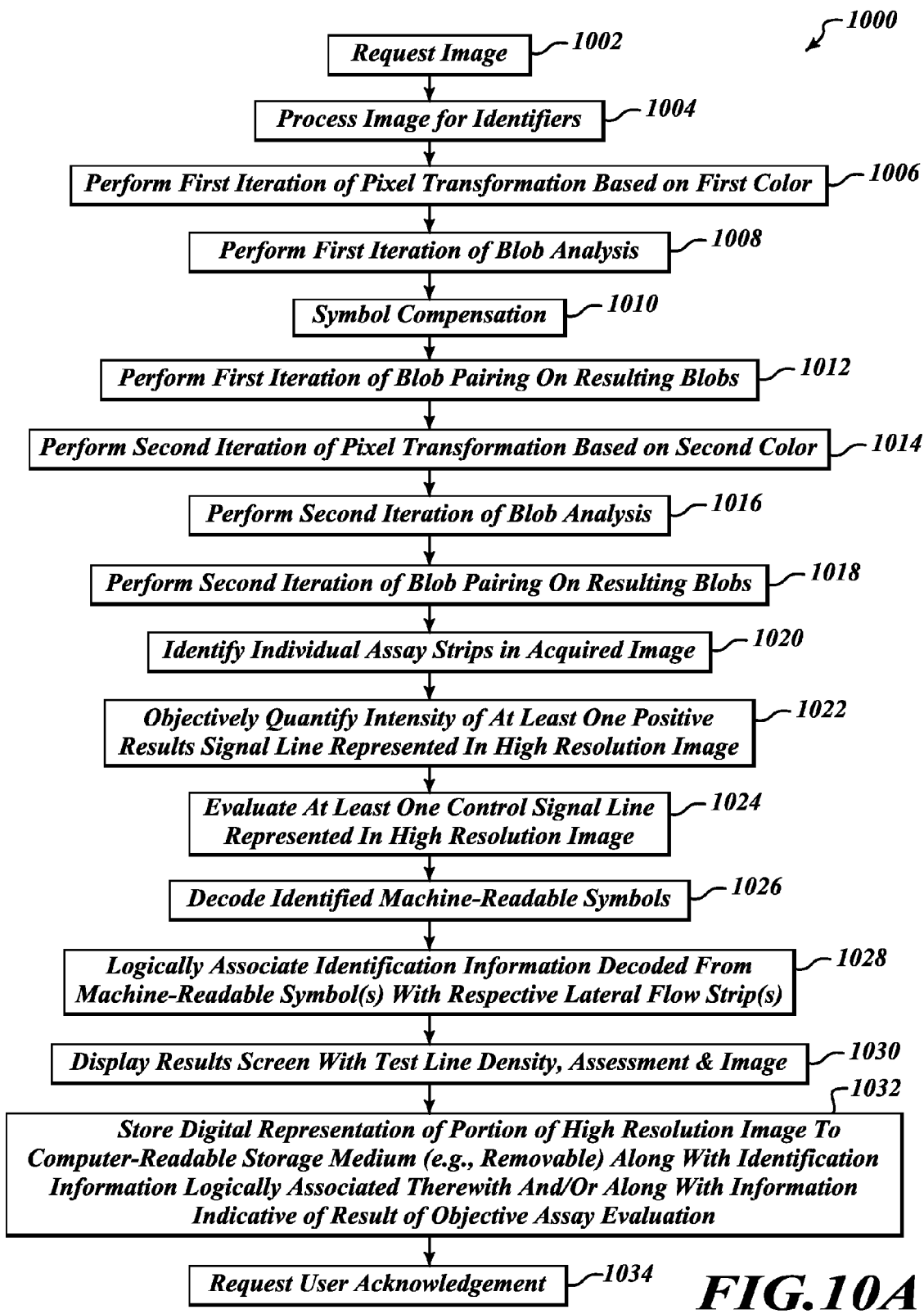
FIG. 10A is a flow diagram showing a method of operating an assay device according to one illustrated embodiment, including computationally identifying individual assay strips in an acquired high resolution image.

FIG. 10A shows a method 1000 of operating an assay device according to one illustrated embodiment, including computationally identifying individual assay strips in an acquired high resolution image. The method 1000 may determine actual color distribution of test results and control signal lines, using red, green, blue (i.e., RGB) ratios or other color ratios, which may advantageously facilitate analysis.

At 1002, at least one processor initiates a request to an imager to acquire an image, and waits for the image to become available. The current implementation uses TWAIN to communicate with an Avision AVA6+ scanner attached directly to a computer (e.g., assay device 102 or computing system 114 of FIG. 1) executing a set of BACSTAT™ software instructions.

At 1004, the processor(s) processes the acquired image for identifiers. For example, the processor may invoke a third-party software library to search the image for identifier symbols, for example barcode symbols. Thus, the processor(s) may identify any machine-readable symbols in the acquired high resolution image. The processor(s) stores the location and contents of all identifiers (e.g., barcode symbols) located in the acquired image.

The processor(s) then searches the acquired image for test strips, without relying on prior knowledge of how many assay strips might be present in the image or where the assay strips might be found in the image. The processor(s) may perform such using the sub-procedure set out as 1006.

At 1006, the processor(s) performs a first iteration of pixel transformation (i.e., Image Processing I) based on a first color. In particular, a second copy of the acquired image may be made in a memory, in which pixels falling within a particular range of "blue" colors (based on hue and saturation) are identified, and all other pixels are changed to black. The processor(s) may apply standard "erode" and "dilate" filters to reduce noise.

At 1008, the processor(s) performs a first iteration of blob analysis (i.e., Blob Analysis I). In particular, the processor(s) identify connected groups ("blobs") of non-black pixels. A bounding rectangle is recorded for each blob, as well as a "weight" value indicating the number of non-black pixels making up the blob.

At 1010, the processor(s) performs symbol compensation (i.e., Barcode Compensation). In particular, the processor(s) identifies pairs of blobs where the weight of each blob is within a particular range, the blobs' bounding rectangles overlap in the horizontal dimension, and the vertical distance between the blobs' centers is within a particular range. The processor(s) remove the blobs from the set and replaces the blobs with a single, larger, synthesized blob whose bounding rectangle is the smallest rectangle enclosing both smaller blobs, and whose weight is the sum of the smaller blobs' weights plus the area in between the two smaller blobs. The processor(s) calculates the latter area by multiplying the distance between the upper blob's lower bound and the lower blob's upper bound by the mean of the two blobs' widths.

At 1012, the processor(s) performs a first iteration of blob pairing is performed (i.e., Blob Pairing I) on blobs resulting from the first duration of blob analysis. In particular, the processor(s) identifies pairs of related blobs where the weight of one blob is greater than a particular threshold, the ratio of weights between the two blobs falls within a particular range, the blobs' bounding rectangles overlap in the horizontal dimension, and the vertical distance between the blobs' centers is below a particular threshold. When a pair is identified, it is recorded and the component blobs are excluded from further pairing. The processor(s) repeats such until all such pairs have been found.

At 1014, the processor(s) performs a second iteration of pixel transformation based on a second color (i.e., Image Processing II). In particular, the processor(s) makes a third copy of the image, in which pixels falling within a particular range of "white" colors (based on saturation and brightness) are identified, and all other pixels are changed to black. The processor(s) may apply standard "erode" and "dilate" filters to reduce noise.

At 1016, the processor(s) performs a second iteration of blob analysis on the results from the second iteration of pixel transformation (i.e., Blob Analysis II). In particular, the processor(s) identify connected groups of non-black pixels, in a fashion similar to that described at 1008.

At 1018, the processor(s) perform a second iteration of blob pairing on blobs resulting from the second iteration of blob analysis (referred to as Blob Pairing II). In particular, the processor(s) identifies pairs of related blobs in a fashion similar to that at 1012 but using a different weight threshold and range. After each pair is identified, the processor(s) attempts to match the pair against one of the "blue" pairs that was identified earlier at 1012. A potential match is accepted when all four blobs overlap in the horizontal dimension, the smaller white blob is above the larger blue blob, the larger blue blob is above the larger white blob, and the larger white blob is above the smaller blue blob.

While not illustrated, the processor(s) may perform any number of additional iterations of pixel transformation based on additional colors and/or blob analysis on the results of the additional iterations of pixel transformation. Such additional iterations may advantageously be employed to identify different or multiple assay types. Thus, the processor(s) may be configured by an end user to run a variable number of iterations and can match a variable number of blobs in each iteration, for example, based on a template customized for each new assay type. The template may take the form of a data file, which can be supplied with the system software or supplied after the sale of the system or even after some use of the system. Such allows aftermarket configuration of the system to accommodate newly introduced assay types or to accommodate a change to an existing assay type that an end user may not have previously been interested in using.

At 1020, the processor(s) identifies the individual assay strips appearing in the acquired image. In particular, the processor(s) identify each accepted match as a respective assay strip. With each assay strip are associated the bounding rectangles of the four blobs that compose the assay strip, a whole-strip bounding rectangle (i.e., the smallest rectangle enclosing all four blobs), and, if any of the identification (e.g., barcode) symbols found at 1004 intersect the whole-strip bounding rectangle, the contents of the first such identification (e.g., barcode) symbol.

Figure 10B:
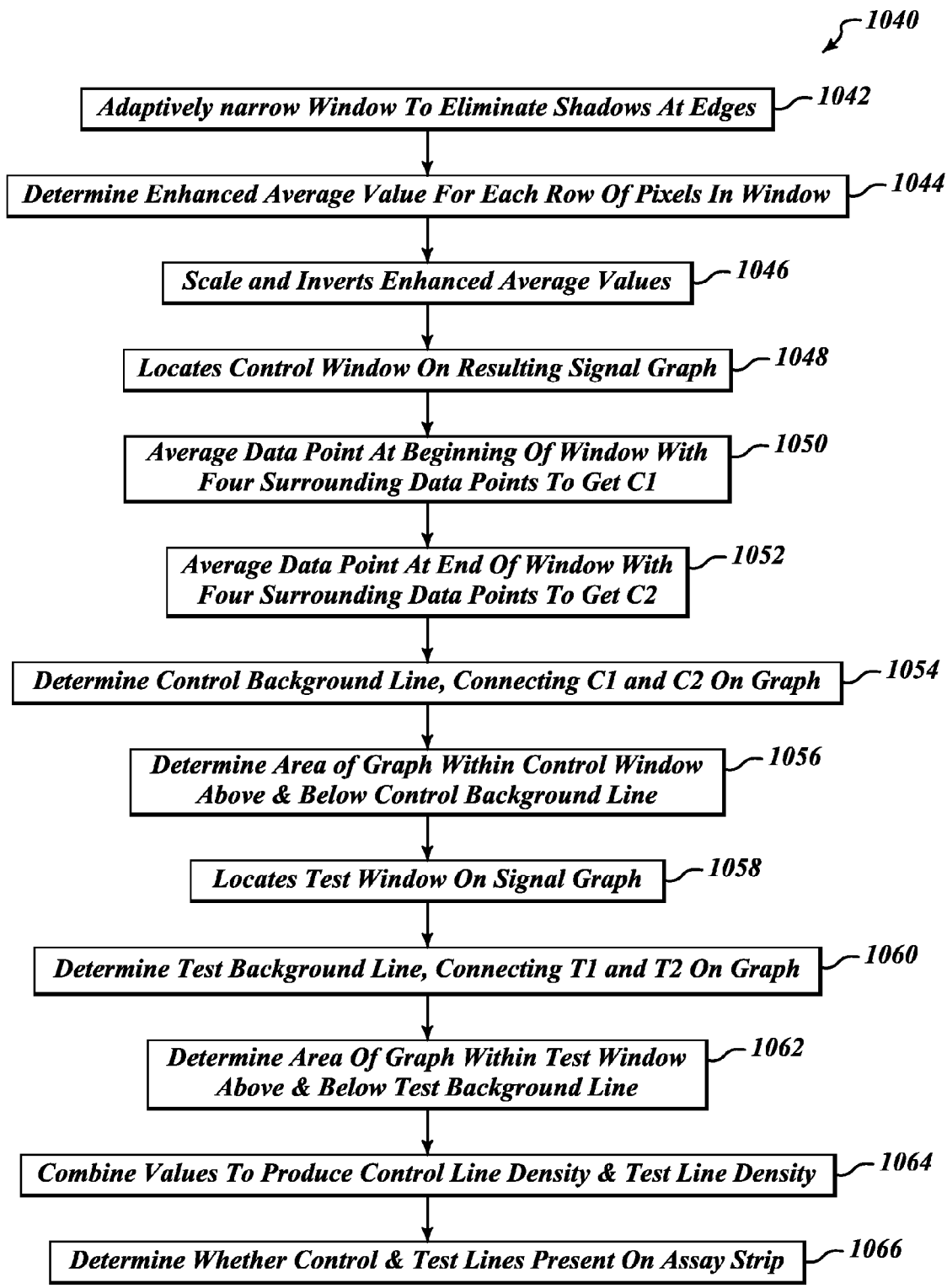
FIG. 10B is a flow diagram showing a method of objectively quantifying at least one positive results signal line and/or evaluating at least one control signal line represented in the high resolution image, according to one illustrated embodiment.

At 1022, the processor(s) objectively quantify at least one positive results signal line represented in the high resolution image. At 1024, the processor(s) evaluate at least one control signal line represented in the high resolution image. In quantifying the positive results signal line and/or evaluating control signal line, the processor(s) may analyze the section of the acquired image residing inside the bounding rectangle of the larger white blob associated with each test strip (i.e., the "window"). The performing 1022 and 1024, the processor(s) may employ a method 1030 (FIG. 10B).

At 1026, the processor(s) may decode identification information encoded in the identified machine-readable symbols. At 1028, the processor(s) may logically associate the decoded identification information with the respective assay strip.

At 1030, the processor(s) displays a results screen with information about each test strip. The information may include the test line density, the assessment (e.g., Positive, Negative, Blank), and a high resolution image of the assay strip.

At 1032, the processor(s) store results for each assay strip in a database on a computer-readable storage medium (e.g., hard disk, optical disk, floppy disk, FLASH card, etc.). Each record may include a full high resolution image of the assay strip, the assessment, the current time, a flag indicating whether the user has acknowledged the result, and the name of the user who initiated the scan or assay. Each record may also contain various data entered by the user to identify the assay strip and the sample that was tested. Information read from the symbols (e.g., barcode symbols) may be used to match each assay strip to the previously entered data.

At 1034, the processor(s) displays a screen that requires the user to acknowledge each test result, before proceeding to additional scans or assays.

FIG. 10B shows a method 1040 of objectively quantifying at least one positive results signal line and/or evaluating at least one control signal line represented in the high resolution image, according to one illustrated embodiment. The method 1030 may be employed in performing 1022 and/or 1024 of the method 1000 (FIG. 10A).

Figure 10C:
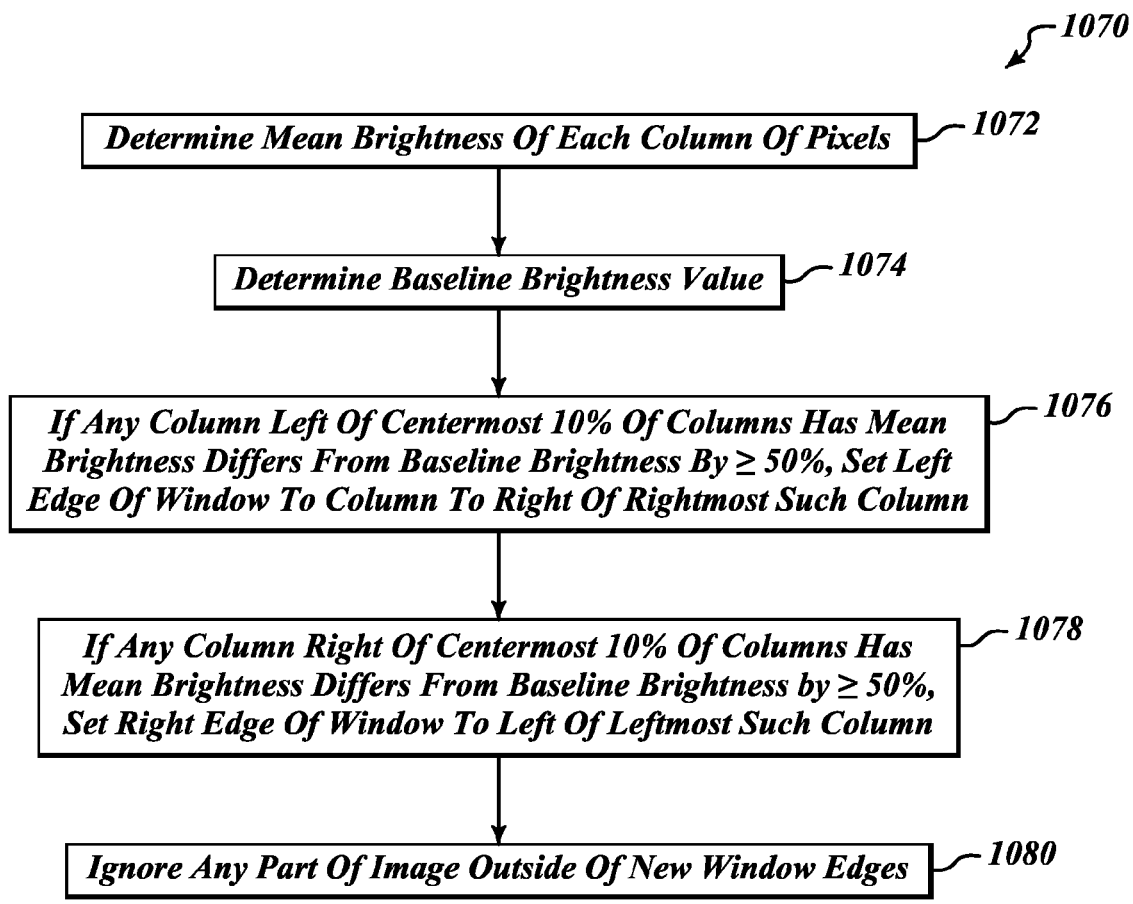
FIG. 10C is a flow diagram showing a method of adaptively narrowing a window to eliminate shadows at edges of the window, according to one illustrated embodiment.

At 1042, the processor(s) adaptively narrows the window to eliminate shadows at the edges. For example, the processor(s) may employ a method 1070 (FIG. 10C).

At 1044, the processor(s) determine an "enhanced average" value for each row of pixels in the window. This is defined as the mean brightness for rows where the difference between the darkest pixel and the mean brightness is below a particular threshold, and as the brightness of the brightest pixel for the other rows.

At 1046, the processor(s) scales and inverts the enhanced average values, producing a data set that can be visualized as a graph (i.e., the "signal graph") 1090 (FIG. 10D) whose peaks indicate darker rows in the image.

At 1048, the processor(s) locates the "control window" 1092 on the signal graph. For example, the processor(s) may search for the highest peak within a particular range of rows and centering a fixed-size window 1092 on the peak. This peak is denominated "CP" (FIG. 10D).

Figure 10D:
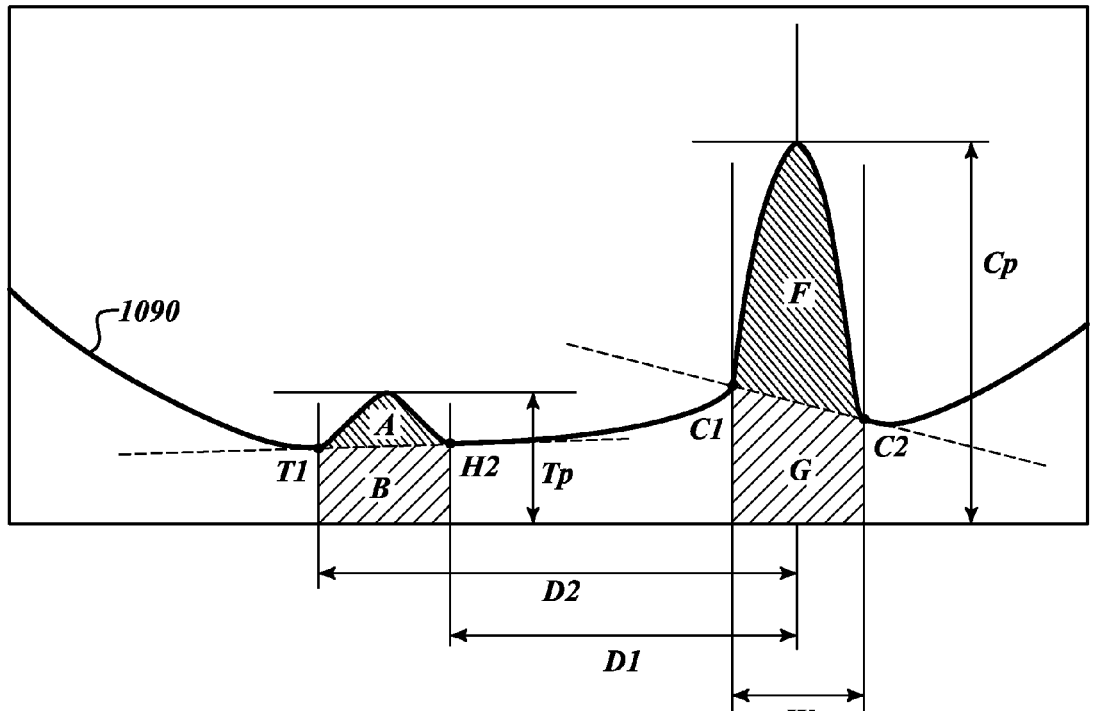
FIG. 10D is a graph representing the interrelationship of various parameters and variables in performing an assay, according to one illustrated embodiment.

At 1050, the processor(s) averages a data point at the beginning of the window 1092 with the four surrounding data points, to obtain a point denominated "C1" (FIG. 10D). At 1052, the processor(s) averages a data point at the end of the window 1092 with the four surrounding data points to obtain a point denominated "C2" (FIG. 10D).

At 1054, the processor(s) determines the "control background line" 1094 which is a line connecting C1 and C2 on the graph 1090 (FIG. 10D). At 1056, the processor(s) determines an area of the graph 1090 within the control window 1092 that is above the control background line 1094, which area is denominated as "F" (FIG. 10D). At 1056, the processor(s) also determines an area of the graph within the control window 1092 that is below the control background line 1094, which area is denominated as "G" (FIG. 10D). A point at which the control background line 1094 intersects a vertical line drawn through CP is denominated "CB" (FIG. 10D).

At 1058, the processor(s) locates a "test window" 1096 on the signal graph 1090 (FIG. 10D). For example, the processor(s) may place a fixed-size window 1096 at a particular constant distance D1, D2 away from the control window 1092. The highest peak within the test window is located, denominated "TP" (FIG. 10D). Data points at the beginning and end of the test window 1096 are denominated "T1" and "H2" (FIG. 10D), respectively.

At 1060, the processor(s) determines a "test background line" 1098, the line connecting T1 and H2 on the graph 1090 (FIG. 10D). At 1062, the processor(s) determines an area of the graph within the test window 1096 that is above the test background line 1098, which area is denominated "A" (FIG. 10D). At 1062, the processor(s) also determines an area of the graph within the test window 1096 that is below the test background line 1098, which area is denominated "B" (FIG. 10D). A point at which the test background line 1098 intersects a vertical line drawn through TP is denominated "TB" (FIG. 10D).

At 1064, the processor(s) combine the values obtained at 1048-1062 to produce "control line density" and "test line density" values. The current implementation subtracts CB from CP to obtain the control line density, and subtracts TB from TP to obtain the test line density, although other calculations may be employed.

At 1066, the processor(s) determines whether the control and test results signal lines are present on the assay strip in the acquired image. For example, the processor(s) may compare control and test line densities against thresholds (e.g., factory-calibrated thresholds). Such results in a categorical assessment of the assay strip. For example, if both the control and test results signal lines are determined to be present, the assay strip is deemed "Positive". If the control signal line is present but the test results signal line is absent, the assay strip is deemed "Negative". If the control signal line is absent, the assay strip is deemed "Blank".

FIG. 10C shows a method 1070 of adaptively narrowing a window to eliminate shadows at edges of the window, according to one illustrated embodiment. The method 1070 may be employed in performing 1042 of method 1040 (FIG. 10B).

At 1072, the processor(s) determines a mean brightness of each column of pixels.

At 1074, the processor(s) determines a baseline brightness value. For example, the processor(s) may average the mean brightness values of a centermost 10% of columns together, giving a baseline brightness value.

At 1076, the processor(s) determines if any column to the left of the centermost 10% of columns has a mean brightness that differs from the baseline brightness by at least 50% of the baseline brightness. If so, the processor(s) sets the left edge of the window to the column to the right of the rightmost such column.

At 1078, the processor(s) determine if any column to the right of the centermost 10% of columns has a mean brightness that differs from the baseline brightness by at least 50% of the baseline brightness. If so, the processor(s) sets the right edge of the window to the column to the left of the leftmost such column.

At 1080, the processor(s) ignores any part of the image that falls outside the edges of the new window.

FIG. 10D shows a graph 1090 representing the interrelationship of various parameters and variable values in performing an assay, according to one illustrated embodiment.

In particular, the graph 1090 shows the interrelationship of many of the parameter and variable values identified in the methods 1000, 1040, 1070 (FIGS. 10A-10C). For example, the areas F and G above and under the control background line 1094, respectively. Also for example, the areas A and B above and below the test background line 1098, respectively. A number of user controlled parameters are also noted, including parameters D1, D2 that set the distance of the test window 1096 from the control window 1092 as well as the width of the test window 1096, the parameter W that sets the width of control window W, and the parameter T that may set the width of the test window T. FIG. 10D also sets out a number of the geometric relationships that may be employed in the methods 1000, 1040, 1070 including: A, A/F, (A+B)/(F+G), A/(D2−D1), and (A/F)*(W/(D2−D1)), where the symbol "*" indicates multiplication, the symbol "/" indicates division, the symbol "+" indicates addition and the symbol "−" indicates subtraction.

Figure 11:
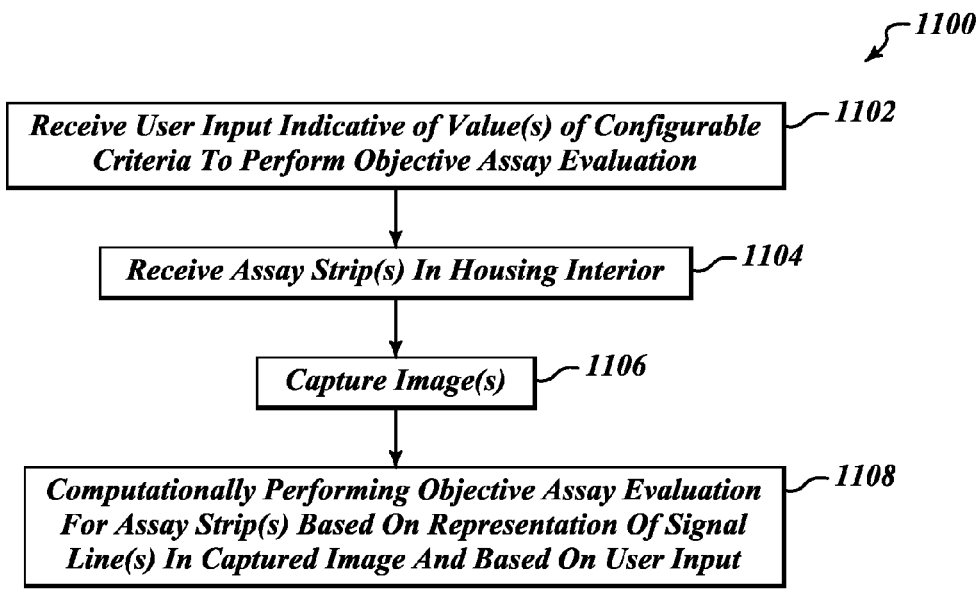
FIG. 11 is a flow diagram of a method of performing assays, according to another illustrated embodiment including receiving user input, receiving assay strips, capturing images and computationally performing objective assay evaluation based on the user input.

FIG. 11 shows a method 1100 of operating an assay system according to one illustrated embodiment.

At 1102, an assay device receives user input indicative of one or more values of configurable criteria used to perform objective assay evaluation. The user input may be entered by a user via a user input device (e.g., keyboard, keypad, pointer device, touch-screen, etc.). At 1104, assay strips are received in an interior of a housing of the assay device. As previously noted assay strips may be received in respective slots, or may be placed under a cover.

At 1106, one or more imagers of the assay device capture high resolution images of the assay strips. As previously noted, the imager(s) may be stationary or may move relative to the assay strips. The imager may be capable of acquiring an image of an area encompassing multiple assay strips.

At 1108, a processor computationally performs objective assay evaluation for the assay strips based on representations of signal lines in the captured high resolution image and based on the received user input. For example, a processor may employ some of the techniques set out in FIGS. 10A-10C.

Figure 12:
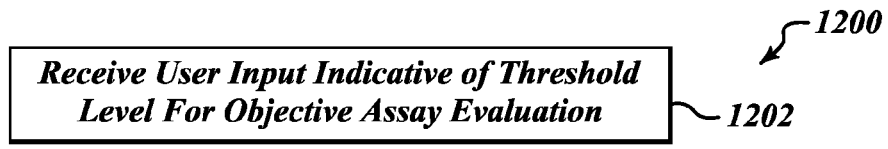
FIG. 12 is a flow diagram showing a method of receiving user input according to one illustrated embodiment.

FIG. 12 shows a method 1200 of receiving user input according to one illustrated embodiment. At 1202, the assay device receives user input indicative of a threshold level for objective assay evaluation. The user input may be entered by a user via a user input device.

Figure 13:
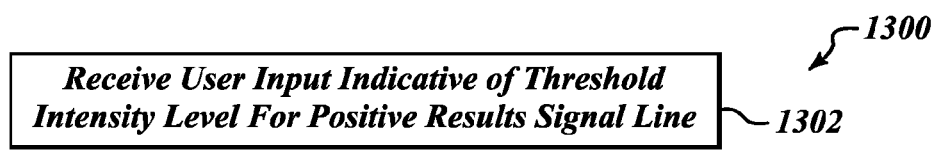
FIG. 13 is a flow diagram showing a method of receiving user input according to another illustrated embodiment.
Figure 14:
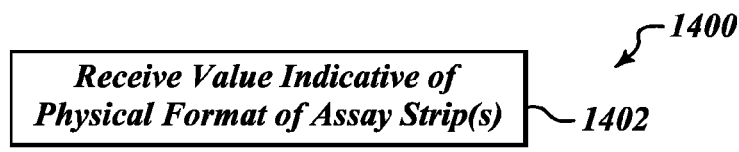
FIG. 14 is a flow diagram showing a method of receiving user input according to a further illustrated embodiment.
Figure 15:
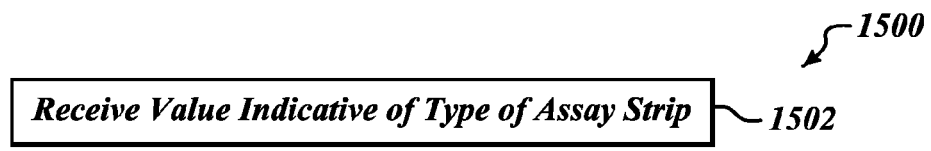
FIG. 15 is a flow diagram showing a method of receiving user input according to yet a further illustrated embodiment.
Figure 16:
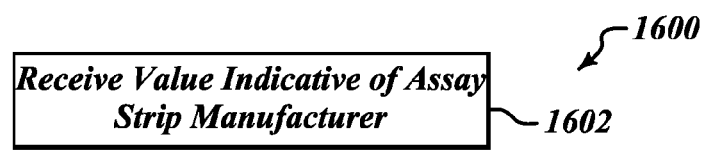
FIG. 16 is a flow diagram showing a method of receiving user input according to yet an even further illustrated embodiment.

FIG. 13 shows a method 1300 of receiving user input according to another illustrated embodiment. At 1302, the assay device receives user input indicative of a threshold intensity level for positive result signal lines. The user input may be entered by a user via a user input device FIG. 14 shows a method 1400 of receiving user input according to yet another illustrated embodiment. At 1402, the assay device receives a value indicative of a physical format of an assay strip. Such values may be indicative of a size (e.g., length, width) of the assay strip or a number and/or position of positive result lines and/or control lines on the assay strip. The user input may be entered by a user via a user input device FIG. 15 shows a method 1500 of receiving user input according to yet another illustrated embodiment. At 1502, the assay device receives a value indicative of a type of assay strip. For example, the value may be indicative of a make and model of assay strip. The user input may be entered by a user via a user input device FIG. 16 shows a method 1600 of receiving user input according to yet a further illustrated embodiment.

At 1602, the assay device receives a value indicative of an assay strip manufacturer. Such may be logically associated with one or more characteristics of the assay strip, for example, physical format including overall dimensions, number and/or position of positive result signal lines, control signal lines, colors, intensity, and/or dimensions of signal lines. The user input may be entered by a user via a user input device or may be scanned or otherwise read using automatic data collection equipment (e.g., machine-readable symbol reader, RFID reader or interrogator, magnetic stripe reader, etc.).

Figure 17:
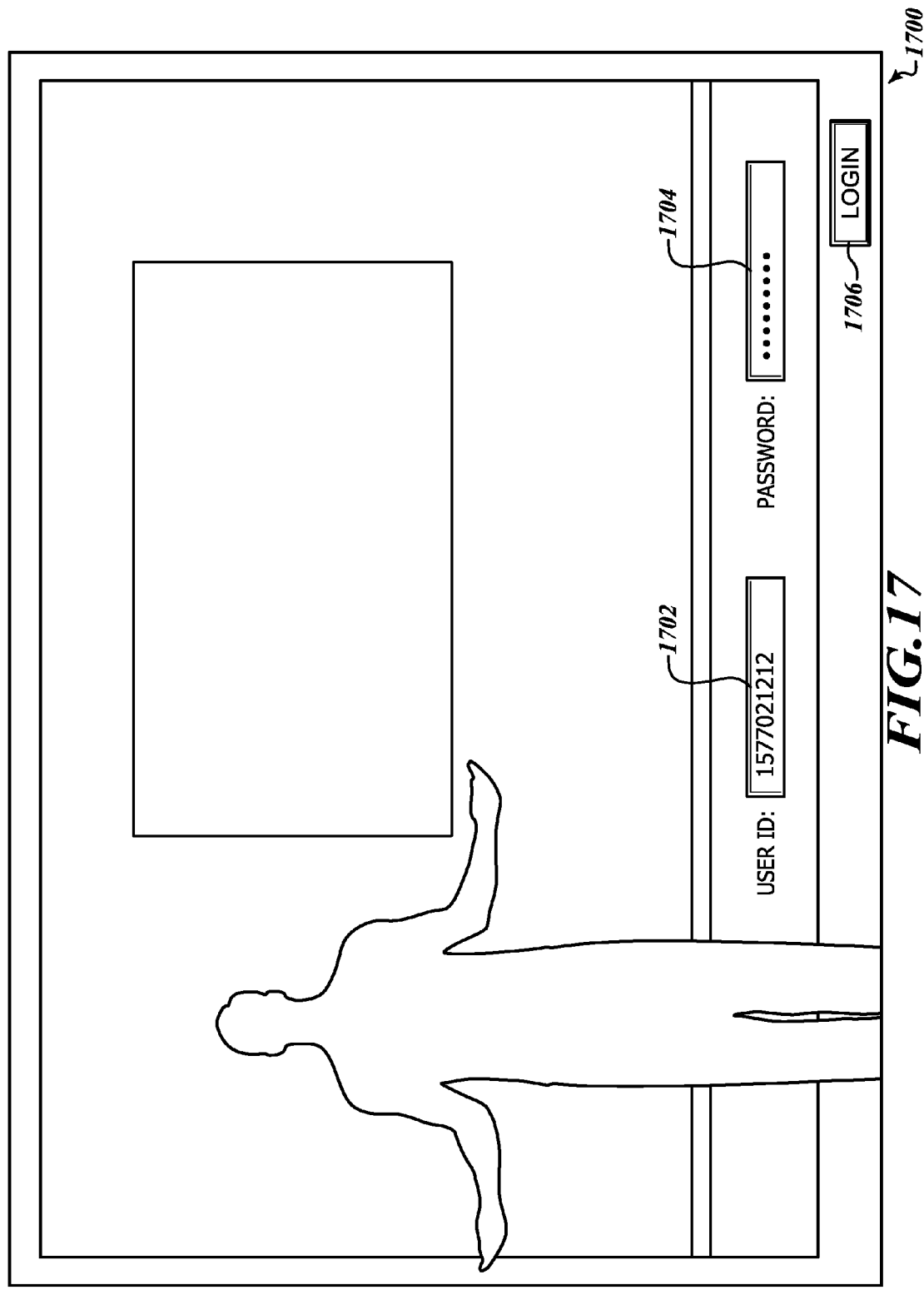
FIG. 17 is a screen print showing an introductory screen of a portion of a user interface of the assay device, according to one illustrated embodiment.

FIG. 17 is a screen print showing an introductory screen 1700 of a portion of a user interface of the assay device, according to one illustrated embodiment. The introductory screen includes a user identifier field 1702 into which an end user may enter a user identifier, for example, via a keyboard. The introductory screen 1700 also includes a password field 1704 into which an end user may enter a password, for example, via a keyboard. The introductory screen 1700 further includes a user-selectable login icon 1706 which a user may select, for example, via a pointer device or a touch on a touch-screen, to log into the assay device. In response to selection of the user-selectable login icon 1706, a processor system of the assay device may evaluate whether the entered user identifier and password are valid and correctly match one another. If validated, entry into the rest of the assay program is granted.

Figure 18:
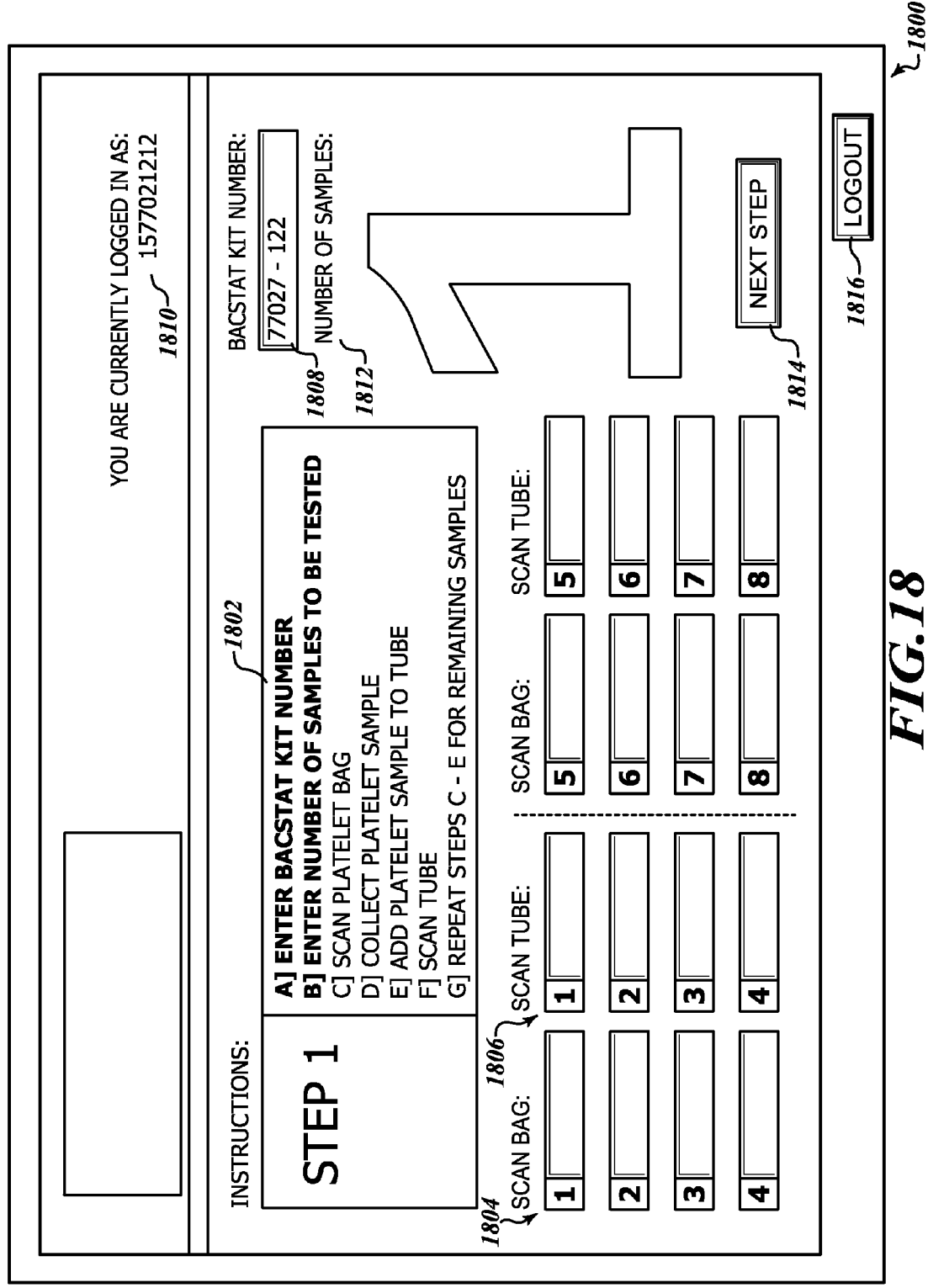
FIG. 18 is a screen print showing a STEP 1 screen of the user interface of the assay device, according to one illustrated embodiment.
Figure 19:
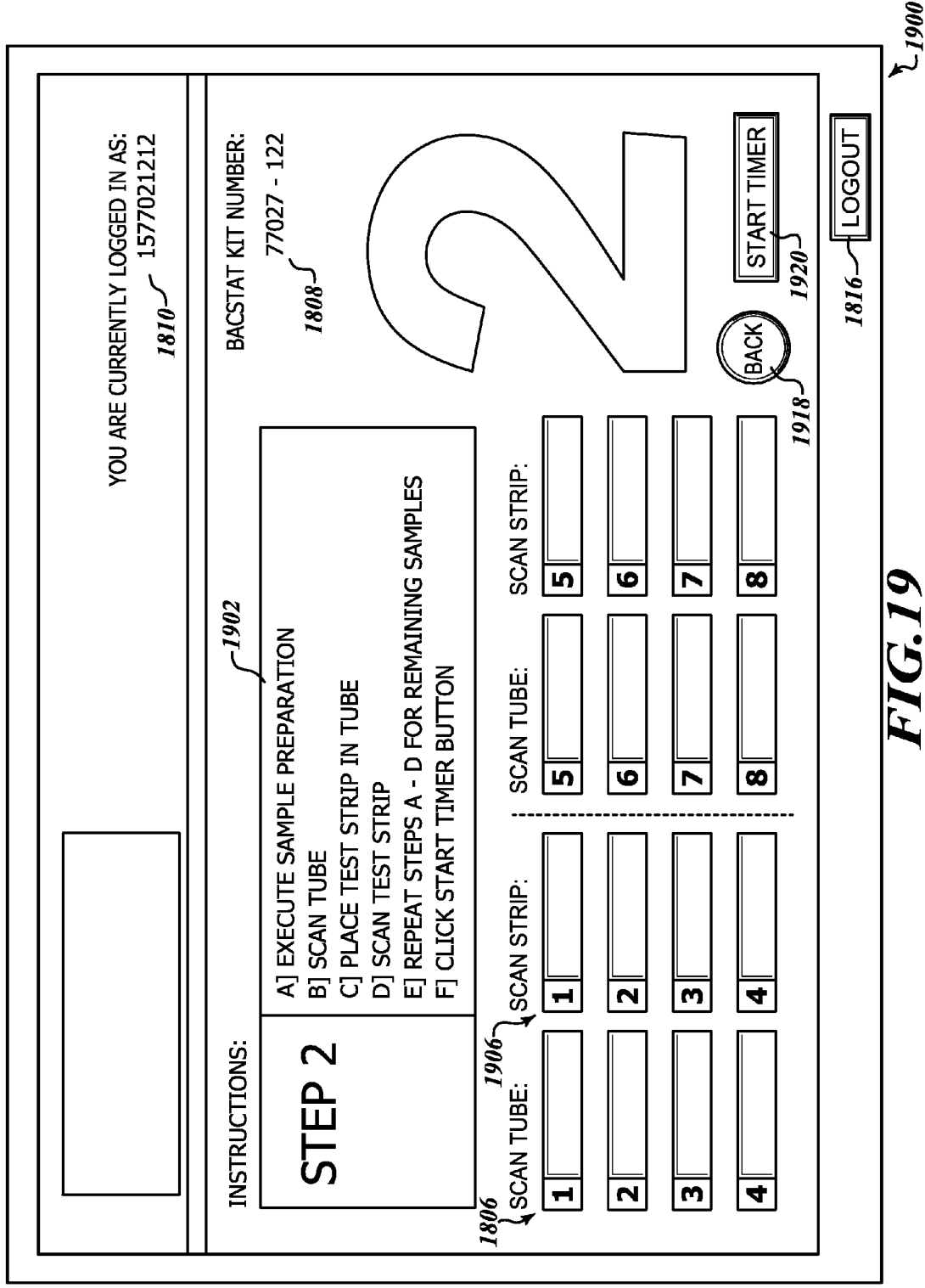
FIG. 19 is a screen print showing a STEP 2 screen of a user interface of the assay device, according to one illustrated embodiment.

FIG. 18 shows a STEP 1 screen 1800 of the user interface of the assay device, according to one illustrated embodiment. The STEP 1 screen 1800 includes an instruction dialog box 1802 which lists various acts or instructions involved in a step 1 of the assay process. For example, the acts or instructions may include: A) entering a bacstat kit number, B) entering a number of samples to be tested, C) scanning platelet bag, D) collecting platelet sample, E) adding platelet sample to tube, F) scanning a tube, and G) repeating the scanning, collecting, adding and scanning for each sample. The STEP 1 screen 1800 includes a number of scan bag fields 1804 (only one called out in FIG. 18) for displaying identifiers read from a platelet bag, and a number of scan tube fields 1806 (only one called out in FIG. 18) for entering or displaying identifiers read from tubes. The STEP 1 screen 1800 may include a kit number field 1808 that displays the identifier of the kit (bacstat kit number). The STEP 1 screen 1800 may include a login identity field 1810 that displays an identifier associated with the end user currently logged in. The STEP 1 screen 1800 includes a sample number field 1812 that indicates the number of samples being assayed. The STEP 1 screen 1800 also includes a user-selectable next step icon 1814. Selection of the next step icon 1814 causes presentation of a STEP 2 screen 1900 (FIG. 19). The STEP 1 screen 1800 also includes a user-selectable logout icon 1816. Selection of the logout icon 1816 causes the user to be logged out of the assay device.

Various screens described below include some fields and/or icons that are identical or similar to other screens. Such fields or icons are identified in the Figures with common reference numbers. In the interest of clarity and brevity, only significant differences between the various screens will be discussed.

FIG. 19 shows a STEP 2 screen 1900 of a user interface of the assay device, according to one illustrated embodiment. The STEP 2 screen 1900 includes a step 2 dialog box 1902 which displays acts or steps associated with step two. For example, the acts may include: A) execute sample preparation, B) scan tube, C) place test strip in tube, D) scan test strip, E) repeating the execute, scan, place and scan for remaining samples and finally F) start a timer. The STEP 2 screen 1900 may include scan tube fields 1904 (only one called out in FIG. 19) to display identifiers read from tubes and scan strip fields 1906 (only one called out in FIG. 19) to display identifiers read from assay strips. The STEP 2 screen 1900 also includes a user-selectable start timer icon 1920, selection of which will cause the assay device to start a timer. The STEP 2 may include a user-selectable back icon 1918, selection of which allows the user to move back to the STEP 1 screen 1800.

Figure 20:
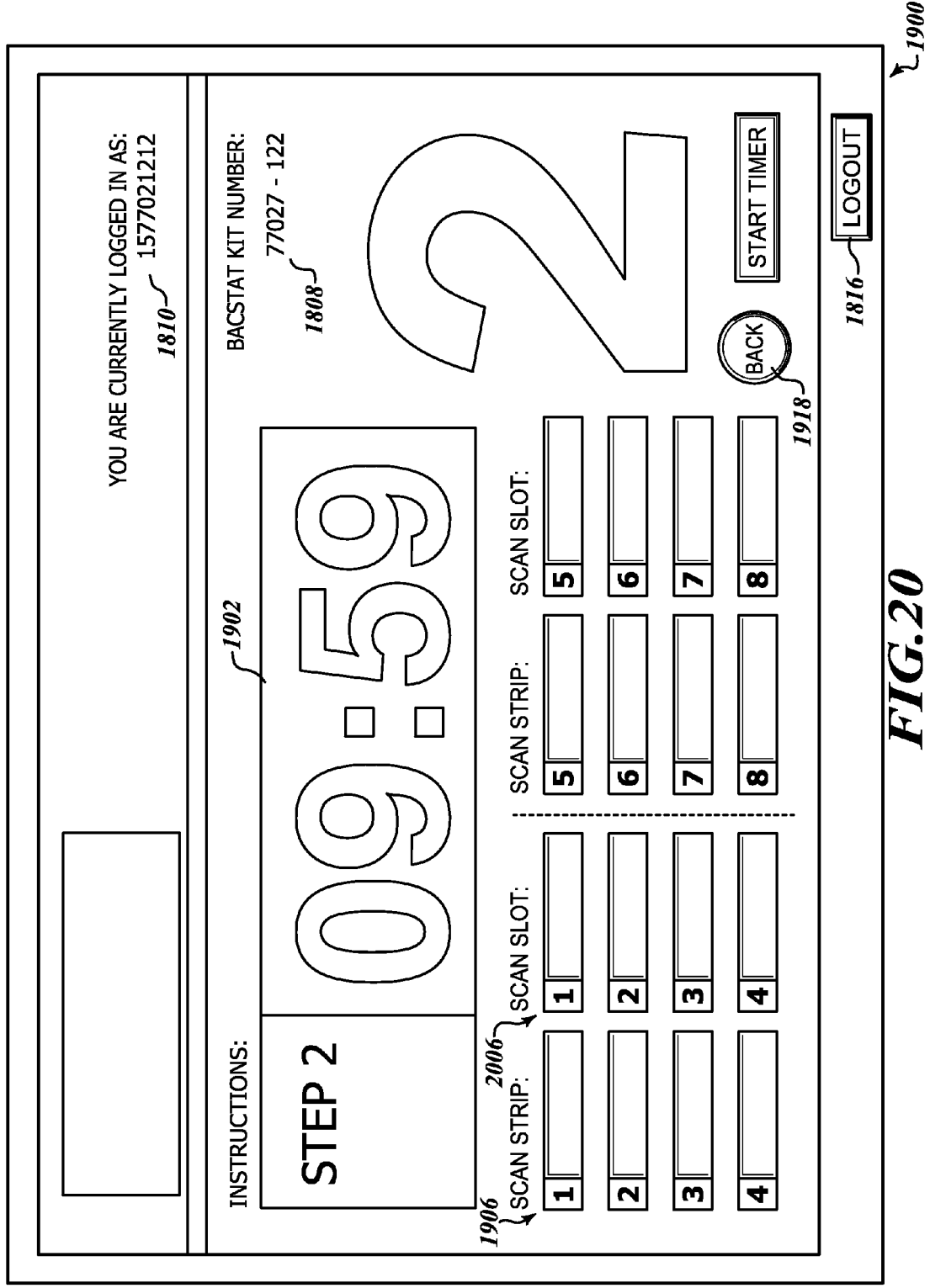
FIG. 20 is a screen print showing the STEP 2 screen of FIG. 19 after selection of the start timer icon.

FIG. 20 shows the STEP 2 screen 1900 after selection of the start timer icon 1920. The dialog box 1902 displays a time of the timer, for example, counting down or counting up.

Figure 21:
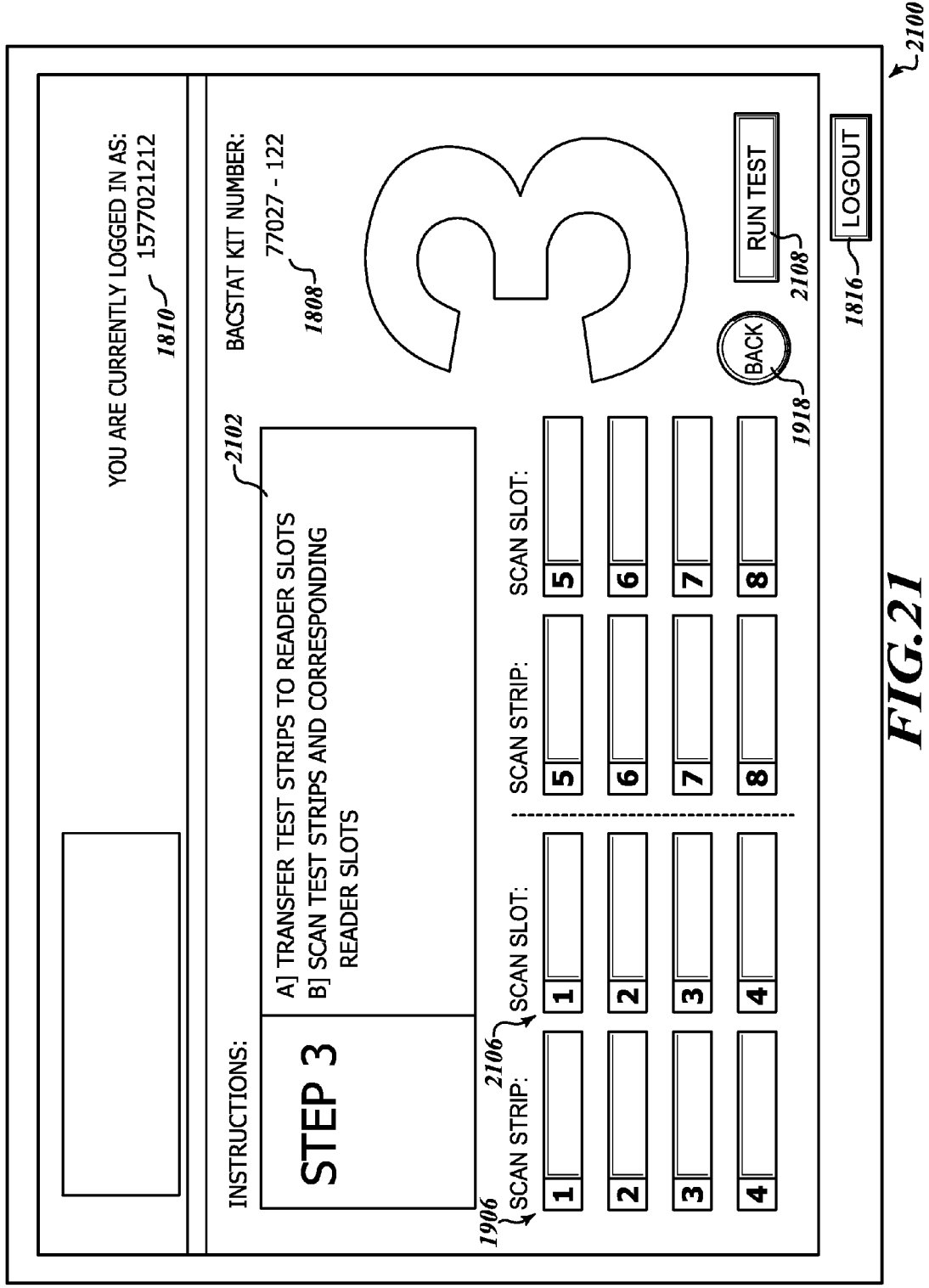
FIG. 21 is a screen print showing a STEP 3 screen of a user interface of an assay device, according to one illustrated embodiment.

FIG. 21 shows a STEP 3 screen 2100 of a user interface of an assay device, according to one illustrated embodiment. The STEP 3 screen 2100 includes a dialog box 2102, displaying acts or steps associated with a step 3. For example, step 3 may include: A) a transfer of test strips to reader slots; and B) imaging of test strips in the slots, as well as reading of identifiers associated with the respective reader slots. The STEP 3 screen 2100 includes scan strip fields 2104 (only one called out in FIG. 21) for displaying identifiers read from assay strips. The STEP 3 screen 2100 also includes scan slot fields 2106 (only one called out in FIG. 21) for displaying identifiers read from slots of the assay device. The STEP 3 screen 2100 further includes a user-selectable run test icon 2108. Selection of the run test icon 2108 causes the assay device to perform an assay or evaluation of the assay strips.

Figure 22:
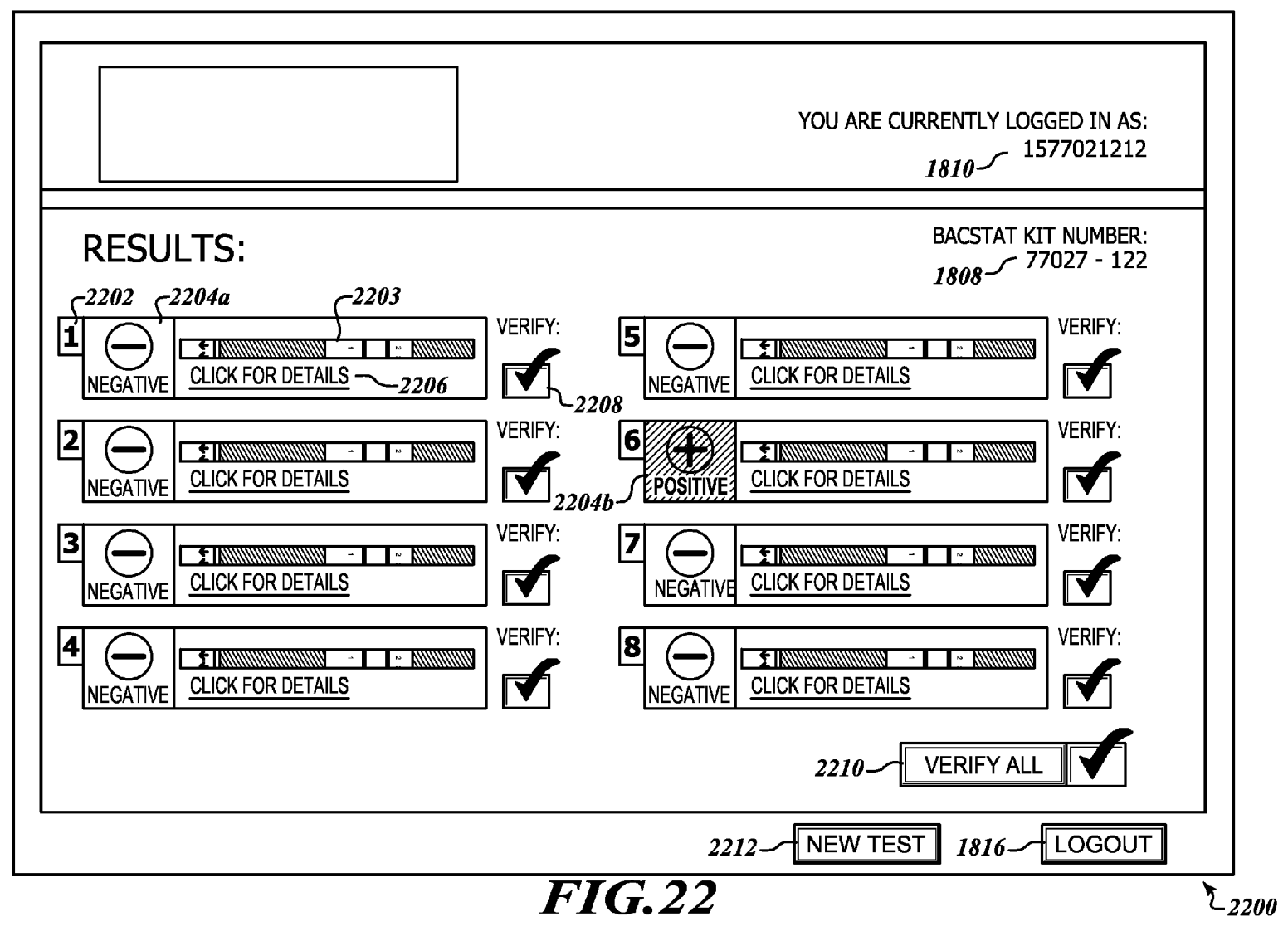

FIG. 22 shows a results screen 2200 of a user interface of an assay device, according to one illustrated embodiment. The results screen 2200 may include a number of results fields 2202 (only once called out in FIG. 22), one for each assay strip that was analyzed. The results fields 2202 includes an image field 2203 (only one called out in FIG. 22) which includes an image of the particular assay strip. A positive results signal line 2306 and a control signal line 2308 are clearly visible in the high resolution image 2304. Associated with each result field 2202, is an indication of the result 2204a, 2204b, collectively 2204. The indications of the result 2204 provide visual feedback on the outcome of the assay. For example, a negative result indication 2204a may be displayed in a first color (e.g., green), include a negative sign as well as the word "NEGATIVE." A positive result indication 2204b may be displayed in a different color (e.g., red), include a plus sign, and the word "POSITIVE." Each of the results fields 2202 may include a user-selectable details icon 2206. Selection of the details icon 2206 brings up a details screen 2300 (FIG. 23) for the particular assay strip.

The results screen 2200 may also include verify fields or icons 2208 (only one called out in FIG. 22). The user may indicate verification of individual results by selecting the respective verify field or icon 2208. The results screen 2200 may further include a verify all results icon or field 2210. A user may indicate verification of all of the results by selecting the verify all field or icon 2210.

The results screen 2200 may also include a user-selectable new test icon 2212. Selection of the new test icon 2212 returns the user to the STEP 1 screen 1800 with all fields initialized.

Figure 23:
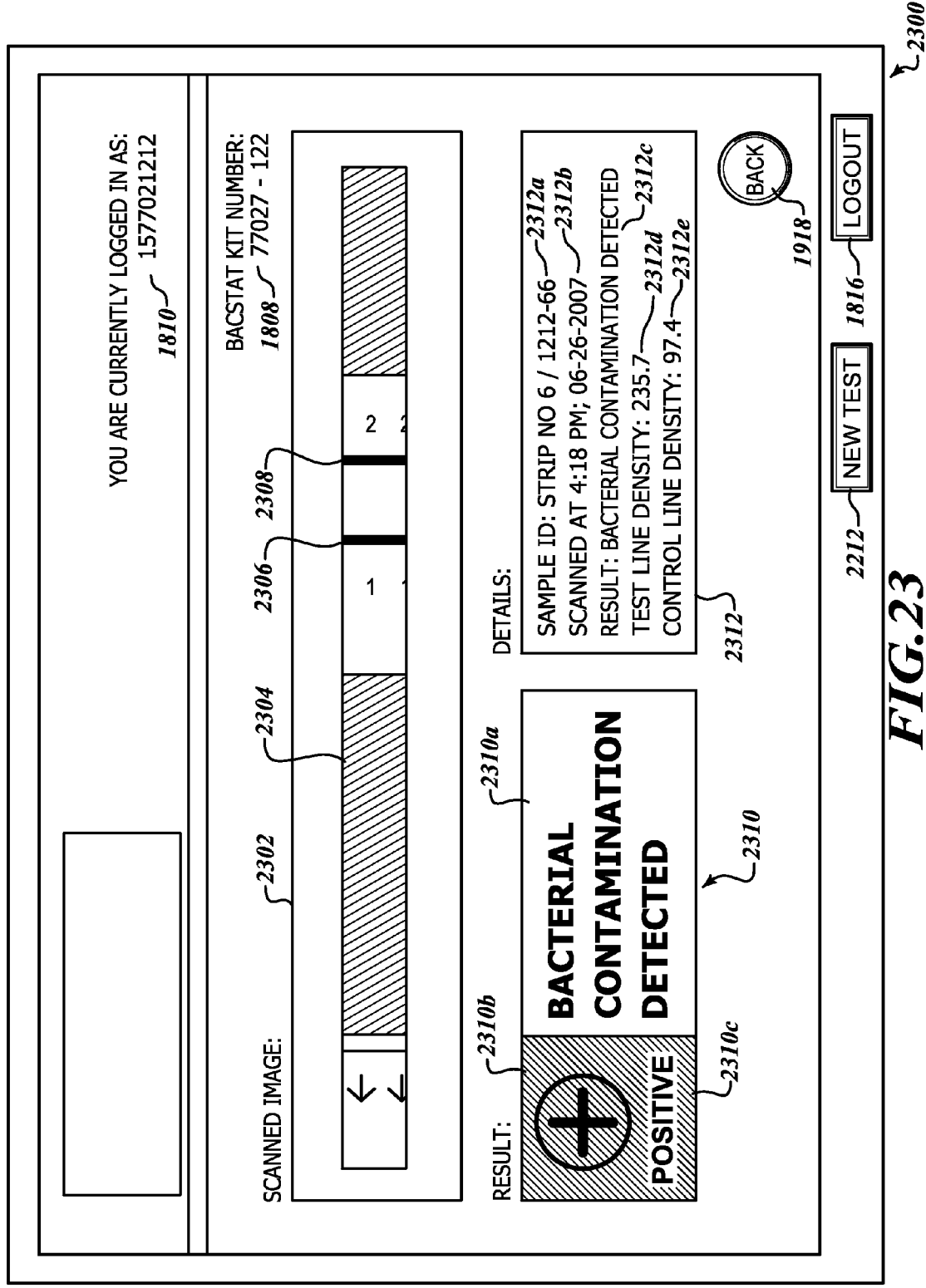
FIG. 23 shows a details screen for the particular assay strip of FIG. 22.

FIG. 23 shows details screen 2300 for assay strip in which a positive result was determined, according to one illustrated embodiment. The details screen 2300 includes an image field 2302 (only one called out in FIG. 22) which includes a high resolution image 2304 of the particular assay strip. A positive results signal line 2306 and a control signal line 2308 are clearly visible in the high resolution image 2304. The detail screen 2300 also includes a results field 2310, displaying the outcome of the assay for the assay strip. The result field 2310 may, for example, display a message which indicates that bacterial contamination was detected 2310a, a plus sign 2310b, and the word "POSITIVE" 2310c to provide a clear indication of the outcome. The result field 2310 may employ a particular color (e.g., red) to further emphasize of results. The detail screen 2300 may further include a details dialog box 2312 including relevant information. Such information may include a sample identifier 2312a, indication of a time and date of a scan 2312b, an indication of results 2312c, an indication of a test line density 2312d, and an indication of a control line density 2312e.

Figure 24:
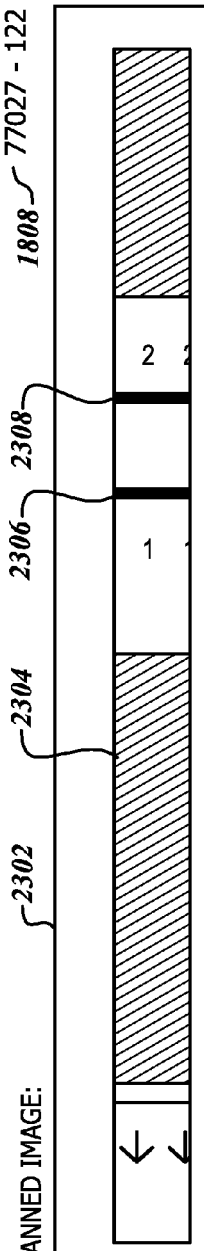
FIG. 24 is a screen print showing the details screen for an assay strip in which a negative result was determined.

FIG. 24 shows the details screen 2400 for another assay strip in which a negative result was determined, according to one illustrated embodiment. The detail screen 2400 includes the same fields and icons as the detail screen 2300. The content of the fields, dialog boxes, are updated to reflect the different assay strip and result. For example, the results dialog box 2310 may include a message which indicates that no bacterial contamination was detected 2310a, a negative sign 2310b, and the word "NEGATIVE" 2310c. The results field 2310 may employ a particular color (e.g., green) to further emphasis the result. Likewise, the details dialog box 2312 may include information that correctly identifies the respective assay strip, time and date of analysis, and results.

Figure 25:
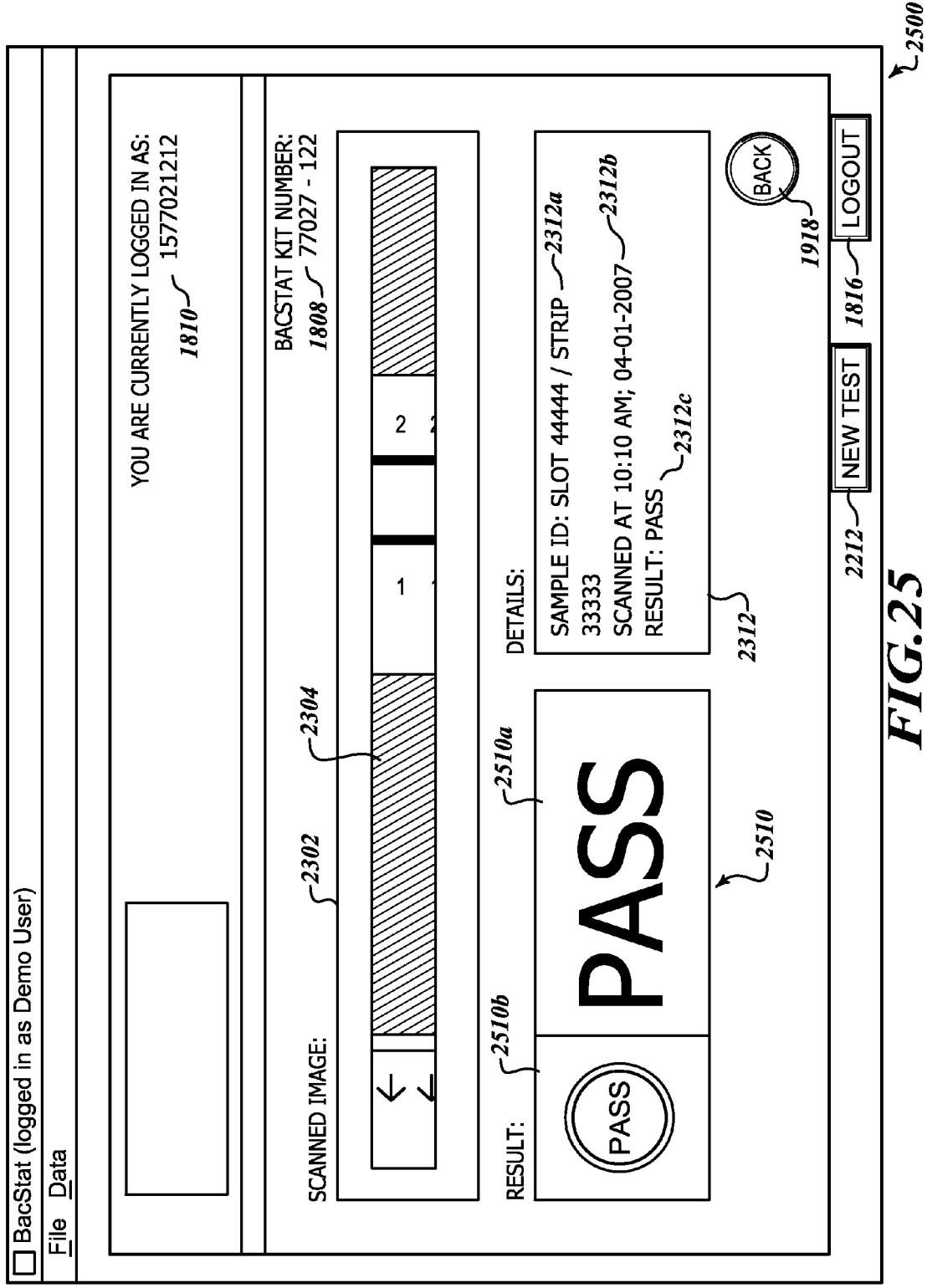
FIG. 25 is a screen print showing a details screen of a user interface of an assay device, according to another illustrated embodiment.

FIG. 25 shows a detail screen 2500 of a user interface of an assay device, according to another illustrated embodiment. The detail screen 2500 may present data in a different fashion than the detail screen 2300 (FIG. 23) and detail screen 2400 (FIG. 24). For example, a results dialog box 2510 may provide a pass/no pass indication 2510a indicating whether the particular assay strip has passed or not passed. Likewise, the results dialog box 2510 may include an iconic representation of a pass or no pass status 2510b and may employ different colors for different outcomes. In some embodiments, outcomes may include an inconclusive outcome in addition to the pass and no pass outcomes. The detail screen 2500 may present pass information as well as identification information and scan time and date in a details dialog box 2312.

FIG. 26 shows a first instruction screen 2600 of a user interface of an assay device, according to another illustrated embodiment. An instructions dialog box 2602 contains a set of instructions 2602a that are different from the set of instructions in the instruction dialog box 1802 of the STEP 1 one instruction screen 1800 (FIG. 18). For example, instead of instructing that a kit number be entered, the instruction dialog box 2602 indicates that A) the kit number should be scanned. The instructions 2602a include B) enter a number of samples to be tested, C) scan platelet bag, D) collect platelet sample in tube and scan, and E) repeat C & D for remaining samples. Notably, the instruction dialog box 2602 also collects the separate acts or steps of the dialog box 1802 into a single act or step (labeled D). In some embodiments, entering the number of samples may be optional, since the number of assay strips may be determined via the image processing. The first instruction screen 2600 also includes a pull-down menu 2612 for selecting the number of samples.

Figure 27:
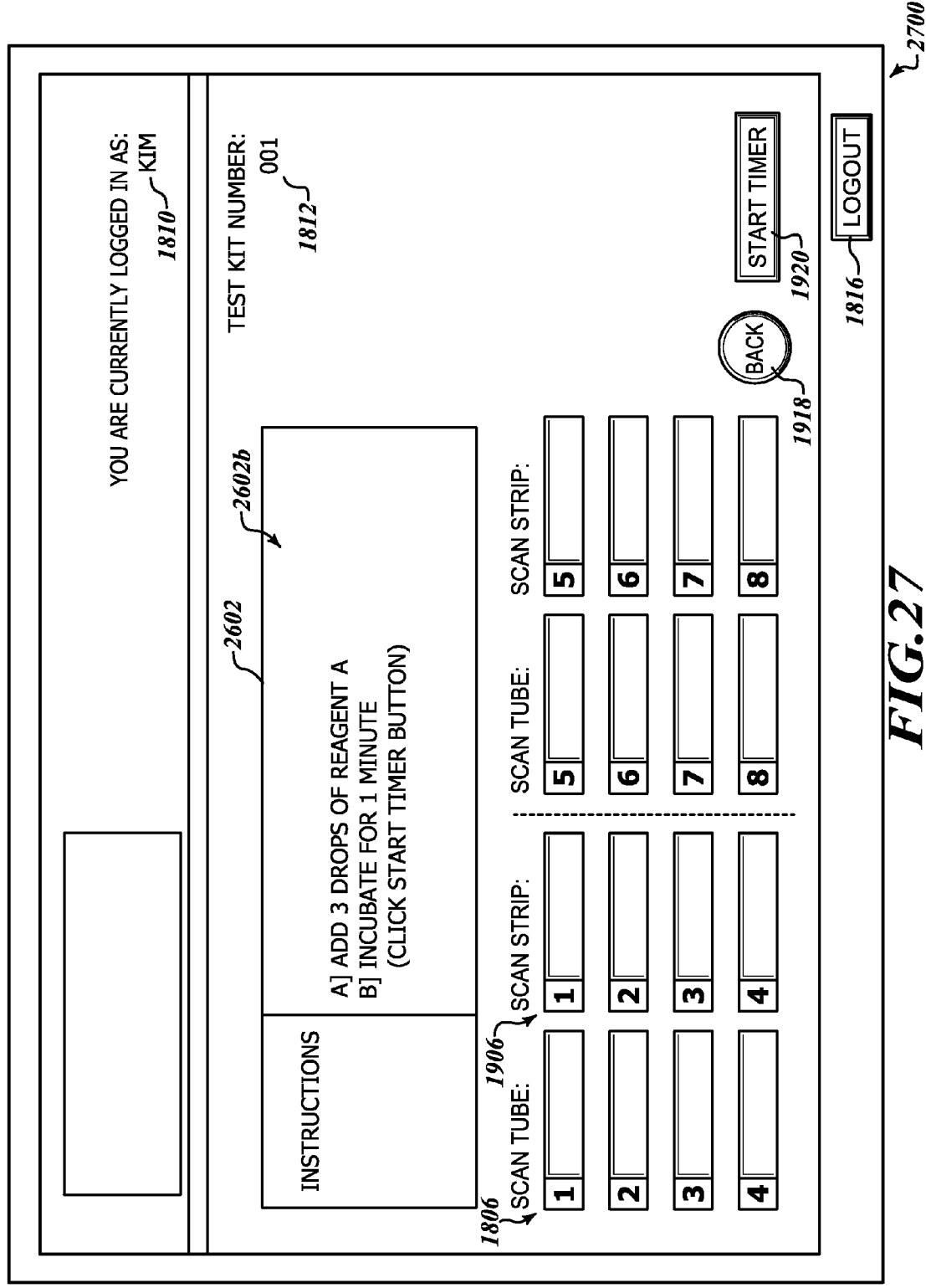
FIG. 27 is a screen print showing a second instructions screen of a user interface of an assay device, according to one illustrated embodiment.

FIG. 27 shows a second instruction screen 2700 of a user interface of an assay device, according to one illustrated embodiment. The second instruction screen 2700 provides instructions 2602*b* for preparing samples which correspond to some of the instructions in the step two instruction screen 1900 (FIG. 19). The instruction dialog box 2602 instructs a user to add drops of reagent and to incubate including: A) adding reagent and B) incubate including a prompt to the end user to start a timer by selecting the start timer icon 1920. Selection of the start timer icon 1920 causes the assay device to start a timer set to the time indicated in the instructions 2602*b*. The second instruction screen 2700 also includes scan tube fields 2704 (only one called out in FIG. 27) to display identifiers read from tubes and scan strip fields 2706 (only one called out in FIG. 27) to display identifiers read from specific assay strips.

Figure 28:
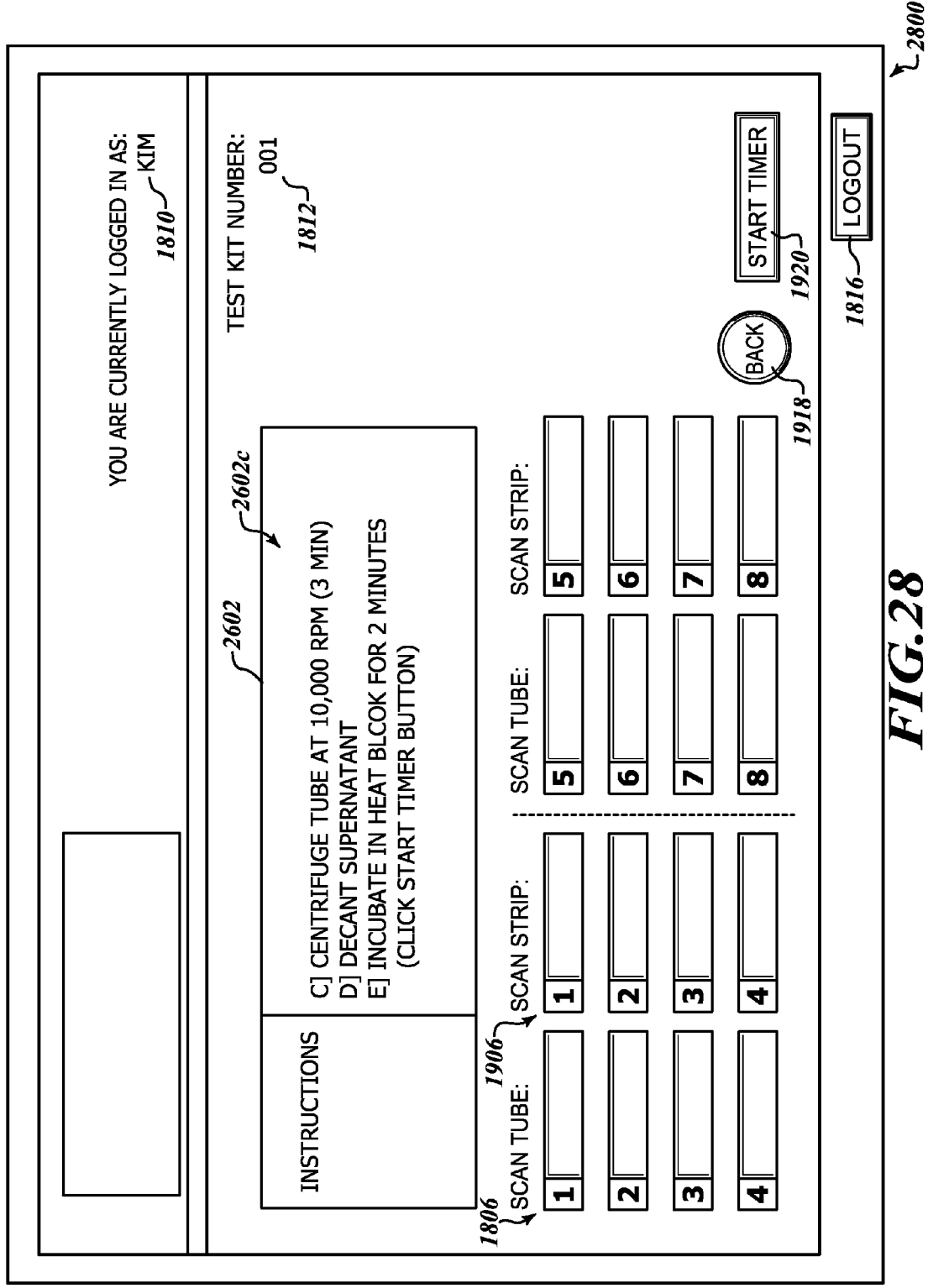
FIG. 28 is a screen print showing a third instructions screen of a user interface of an assay device according to one illustrated embodiment.

FIG. 28 shows a third instruction screen 2800 of a user interface of an assay device according to one illustrated embodiment. The instruction dialog box 2600 provides further instructions 2602*c* for preparing samples to be tested or assayed. Instructions may include: C) centrifuging a tube, D) decant supernatant, and E) Incubated, including a prompt to start a timer by selecting the start timer icon 1920. Selection of the start timer icon 1920 causes the assay device to start a timer set to the time indicated in the instructions 2602*c*.

Figure 29:
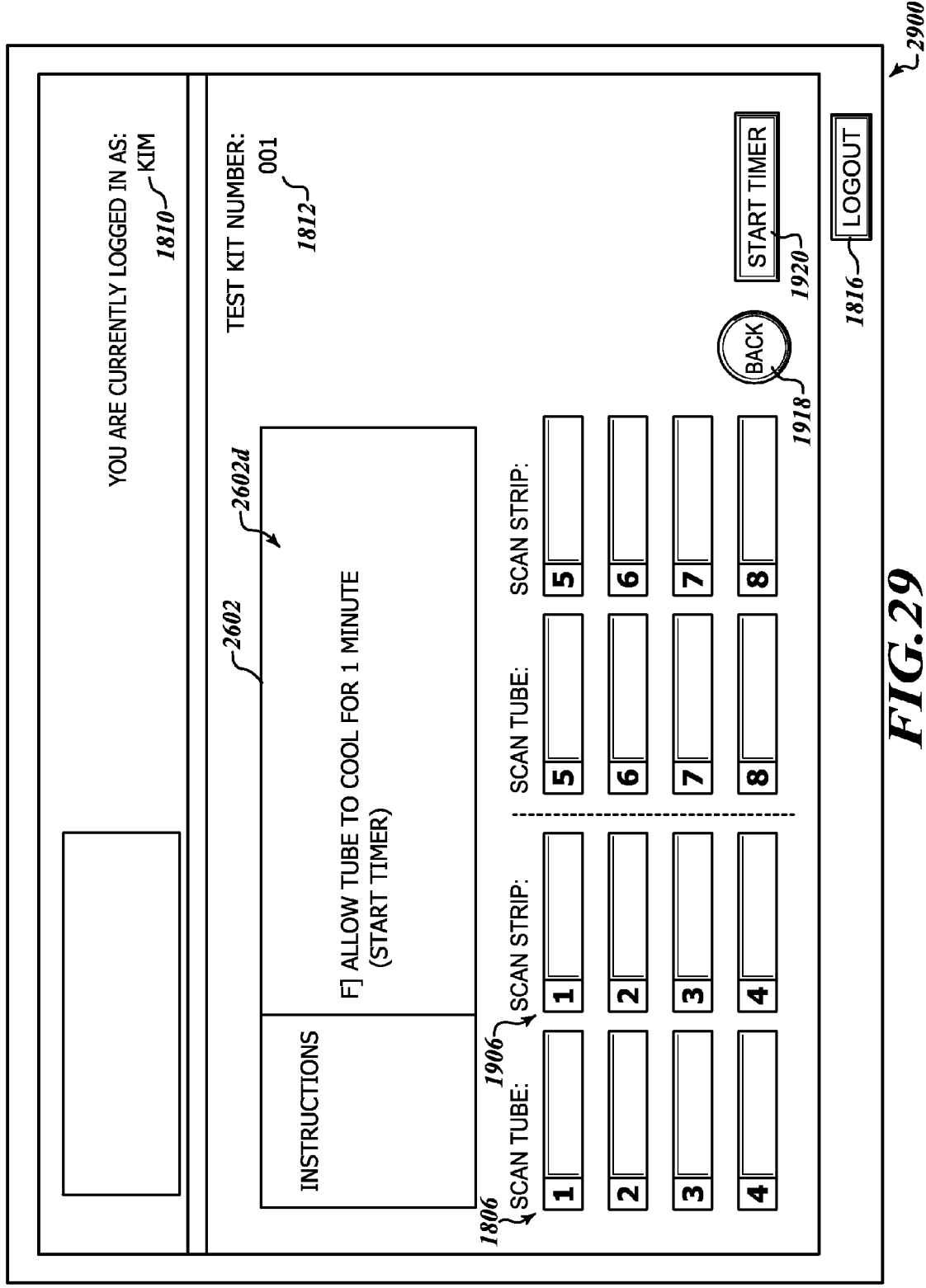
FIG. 29 is a screen print showing a fourth instructions screen of a user interface of an assay device, according to one illustrated embodiment.

FIG. 29 shows a fourth instruction screen 2900 of a user interface of an assay device, according to one illustrated embodiment. The instruction dialog box 2602 displays further instructions 2602*d* for preparing samples to be tested or assayed. For instance, the instructions 2602*d* may include allowing tube to cool, including a prompt to the user to start a time by selecting the start timer icon 1920. Selection of the start timer icon 1920 causes the assay device to start a timer set to the time indicated in the instructions 2602*d*.

Figure 30:
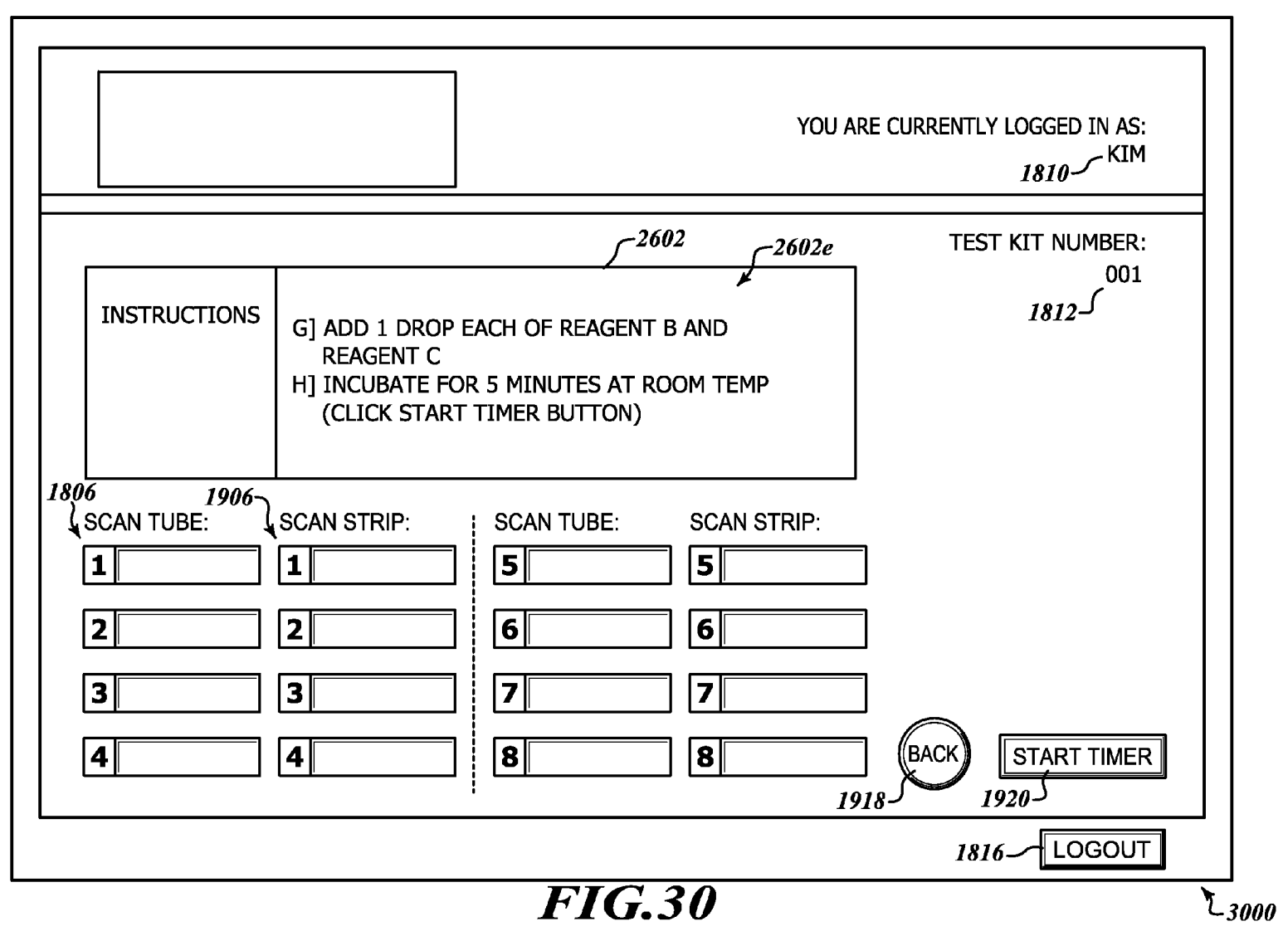

FIG. 30 shows a fifth instruction screen 3000 of a user interface of an assay device, according to one illustrated embodiment. The instruction dialog box 2602 displays further instructions 2602*e* for preparing samples to be tested or assayed. The instructions 2602*e* may include G) adding reagents and H) incubating with a prompt to the user to stat a time by selecting the start timer icon 1920. Selection of the start timer icon 1920 causes the assay device to start a timer set to the time indicated in the instructions 2602*e*.

Figure 31:
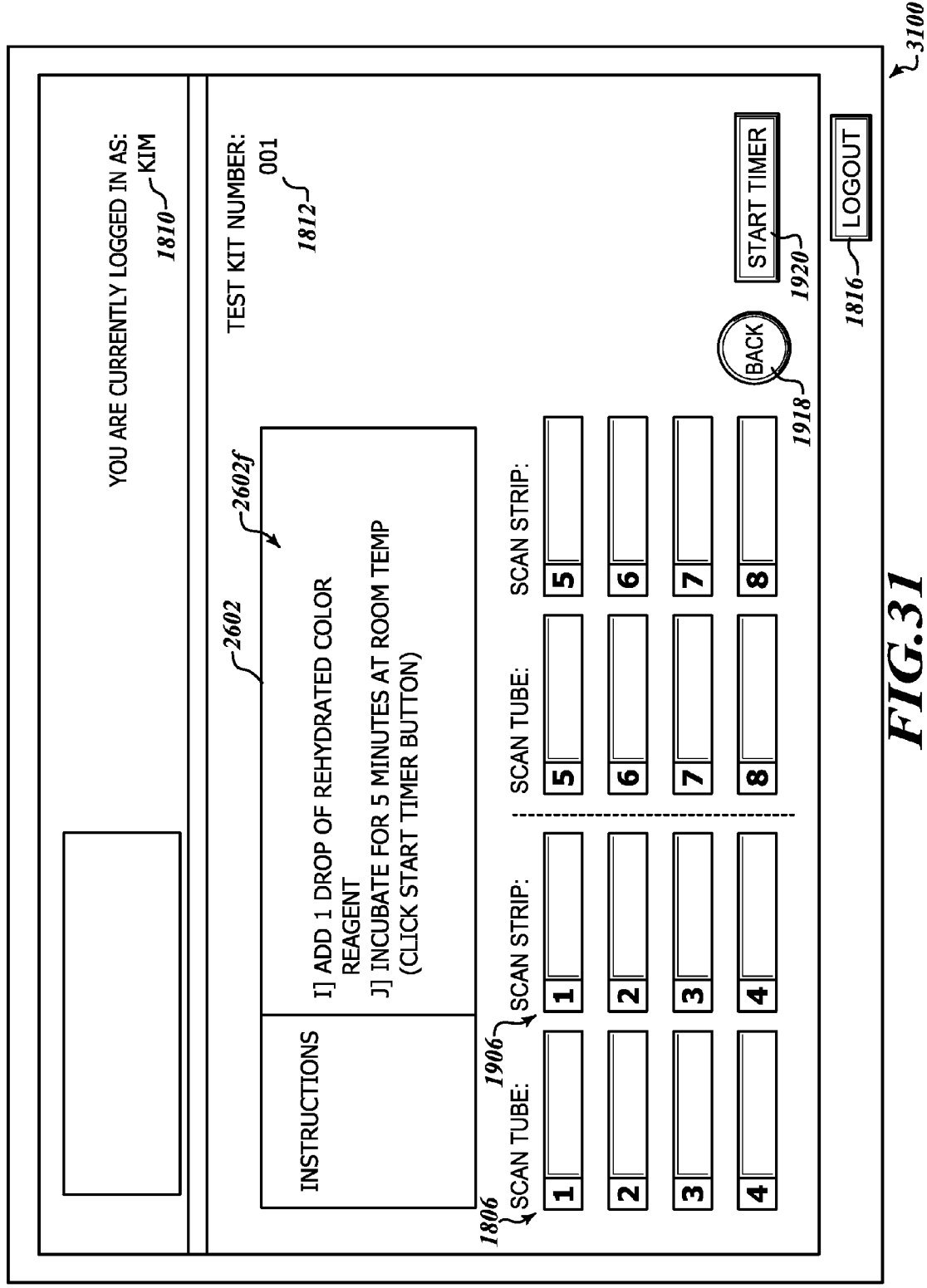
FIG. 31 is a screen print showing a sixth instructions screen of a user interface of an assay device, according to one illustrated embodiment.

FIG. 31 shows a sixth instruction screen 3100 of a user interface of an assay device, according to one illustrated embodiment. The instructions dialog box 2602 displays even further instructions 2602*f* for preparing samples to be tested or assayed. Instructions 2602*f* may include H) add rehydrated color reagent and J) incubate including a prompt to the user to stat a time by selecting the start timer icon 1920. Selection of the start timer icon 1920 causes the assay device to start a timer set to the time indicated in the instructions 2602*f*.

Figure 32:
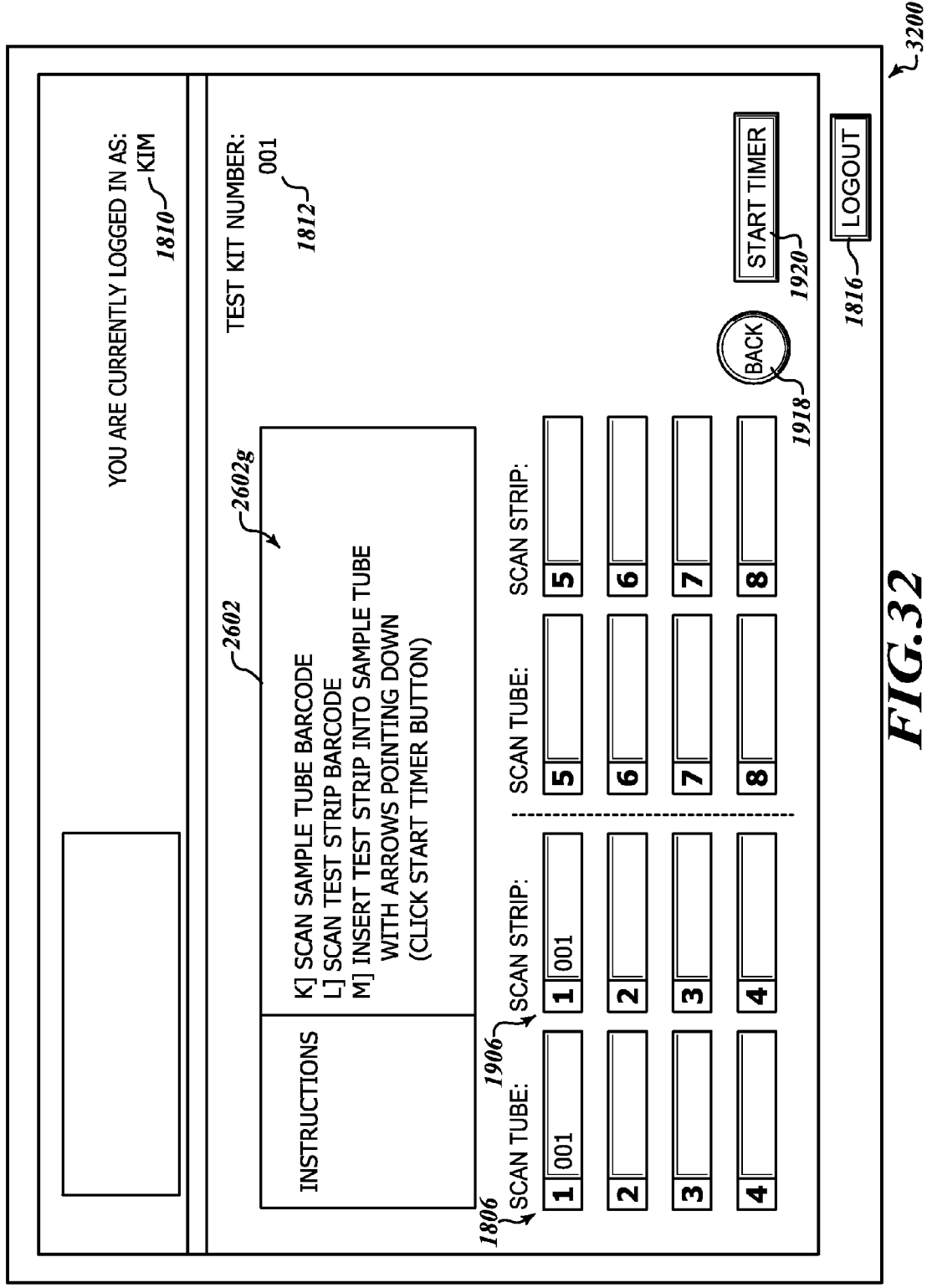
FIG. 32 is a screen print showing a seventh instructions screen of a user interface of an assay device, according to one illustrated embodiment.

FIG. 32 shows a seventh instruction screen 3200 of a user interface of an assay device, according to one illustrated embodiment. The instructions dialog box 2602 displays instructions 2602*g*, including K) reading identifiers from sample tubes, L) reading identifiers from test or assay strips, and M) placing the test or assay strips into sample tubes, along with a prompt to start a timer, for example, by selecting user-selectable start timer icon 1920. Selection of the start timer icon 1920 causes the assay device to start a timer set to the time indicated in the instructions 2602*g*. Notably, the instructions 2602*g* correspond to instructions labeled D-F of the step two instruction screen 1900 (FIG. 19).

Figure 33:
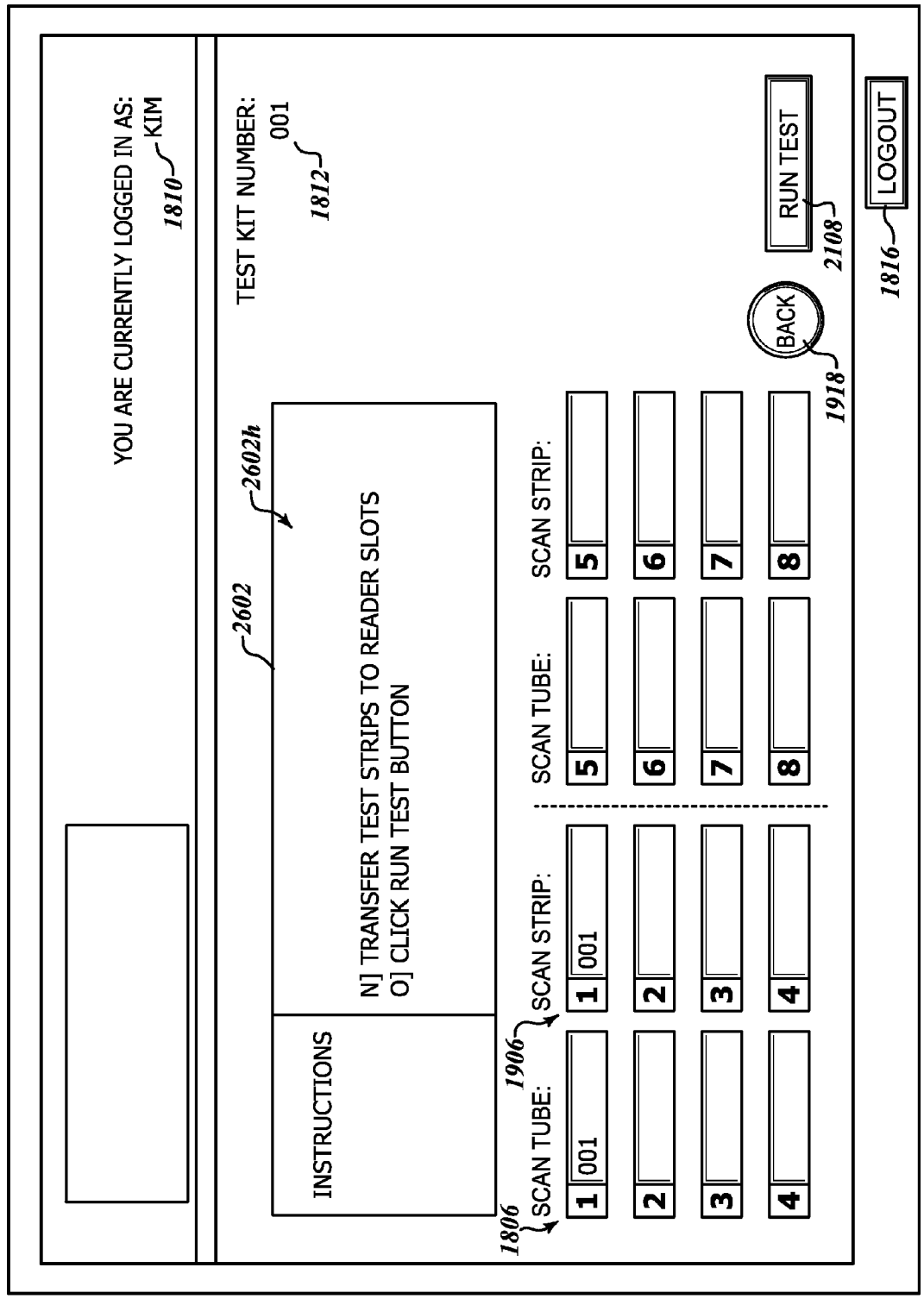
FIG. 33 is a screen print showing an eighth instructions screen of a user interface of an assay device, according to one illustrated embodiment.

FIG. 33 shows an eighth instruction screen 3300 of a user interface of an assay device, according to one illustrated embodiment. The instruction dialog box 2602 displays instructions 2602*h*, including N) prompting the user to transfer test or assay strips to slots in the assay device, and O) prompting the user to start the test by selecting the user-selectable run test icon 1920. Notably, the instructions 2602*h* correspond to the instructions of the step three instruction screen 2100 (FIG. 21).

Figure 34:
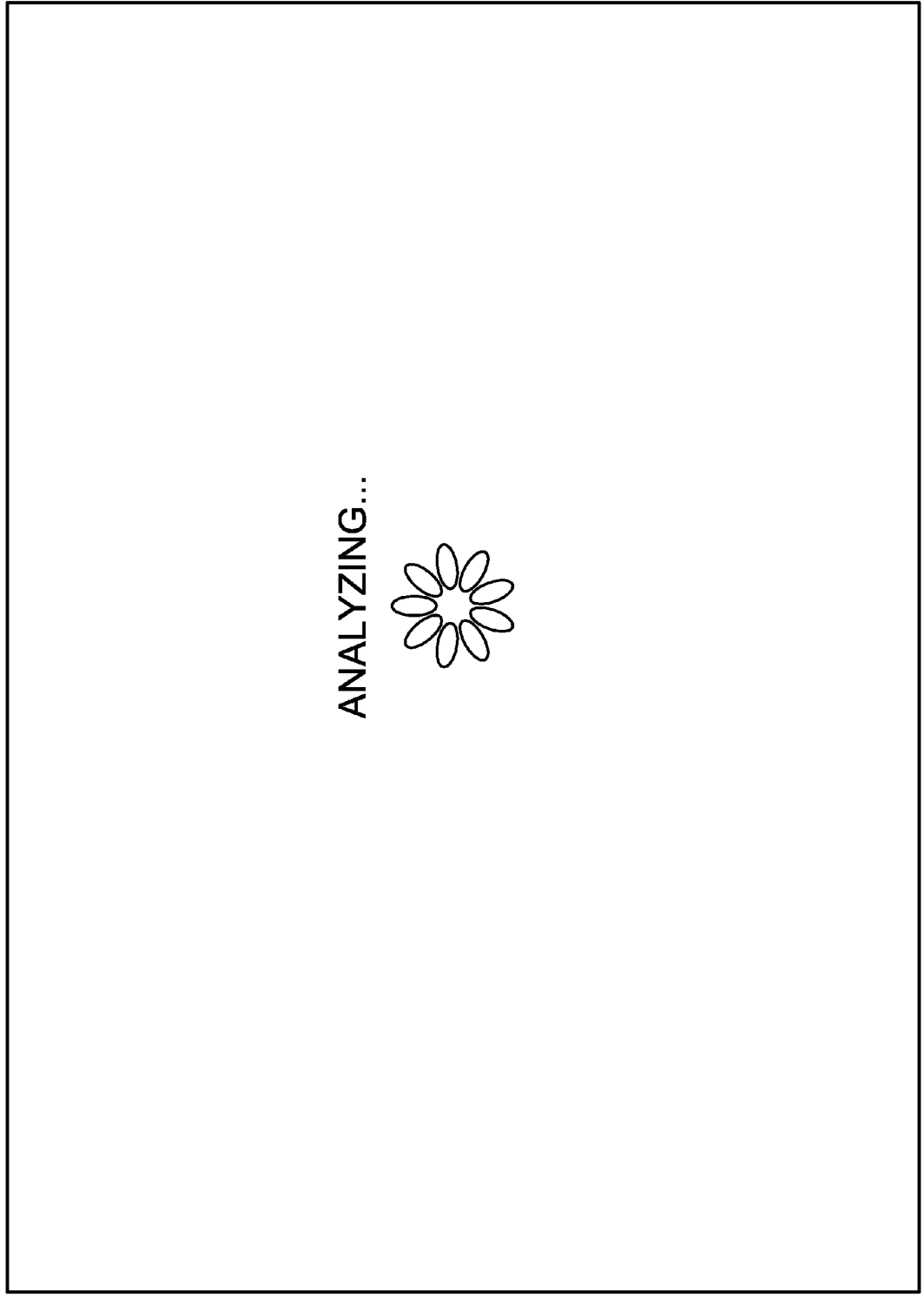
FIG. 34 is a screen print showing an analyzing screen, according to one illustrated embodiment, which may be displayed while the assay device performs analysis, providing the end user visual feedback indicating that the assay device is processing samples.

FIG. 34 shows an analyzing screen 3400 which may be displayed while the assay device performs analysis, providing the end user with visual feedback indicating that the assay device is processing samples.

Figure 35:
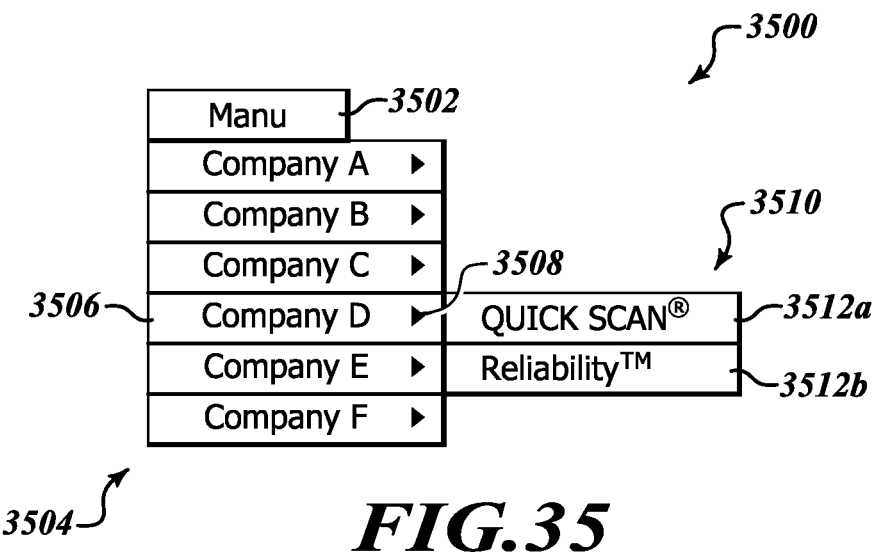
FIG. 35 is a screen print showing a portion of a graphical user to select manufacturer/distributors and/or model/product, according to one illustrated embodiment.

FIG. 35 shows a portion 3500 of a graphical user interface which may be displayed by an assay device or supporting computer, according to one illustrated embodiment. The portion 3500 of the user interface includes a user-selectable manufacturer selection tab 3502 which may appear on a control bar of a user interface. Selection of the manufacturer selection tab 3502 causes the presentation of a manufacturer pull-down menu 3504, which displays a list of assay strip manufacturers or distributors 3506 (only one called out in FIG. 35). A user selectable sub-menu icon 3508 is present if there are multiple options for a given assay strip manufacturer or distributor 3506. Selection of the sub-menu icon 3508 causes presentation of a model pull-down menu 3510. The model pull-down menu 3510 presents a user selectable model icon 3512*a*, 3512*b* for each model of assay strips produced or sold by the manufacturer or distributor. Selection of a model icon 3512*a*, 3512*b* causes the assay device to retrieve specific parameters and variables for the selected assay strip product and to configure the processor executable instructions to perform assays based on the retrieved parameters and variables. The specific parameters and variable for different products may be stored at the assay device, or may be stored remotely therefrom. In some embodiments, that assay device may automatically query manufacturers or distributors (e.g., Website) for specific parameters and variables in response to the selection. In some embodiments, manufacturer/distributors (e.g., server) may transmit (i.e., push) specific parameters and variables to assay devices as products are updated or introduced. This may eliminate the need for the operator or end user to download (i.e., pull) such parameters and variables.

Figure 36:
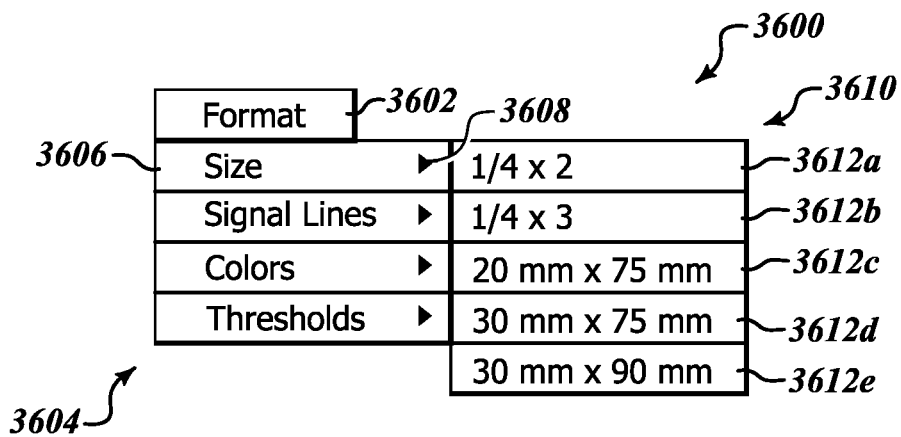
FIG. 36 is a screen print showing a portion of a graphical user to select format options and choices, according to one illustrated embodiment.

FIG. 36 shows a portion 3600 of a graphical user interface which may be displayed by an assay device or supporting computer, according to one illustrated embodiment. The portion 3600 of the user interface includes a user-selectable format selection tab 3602 which may appear on a control bar of a user interface. Selection of the format selection tab 3602 causes the presentation of a format pull-down menu 3604, which displays a list of format options 3606 (only one called out in FIG. 36). A user selectable sub-menu icon 3608 is present if there are multiple choices for a given format option 3606. Selection of the sub-menu icon 3608 (e.g., size) causes presentation of a format choices pull-down menu 3610. The format choices pull-down menu 3610 presents a user selectable format choices icon 3612*a*-3612*e* for each choice of format for the selected format option. Selection of a format choices icon 3612*a*-3612*e* causes the assay device to retrieve specific parameters and variables for the selected format choice and to configure the processor executable instructions to perform assays based on the retrieved parameters and variables. The format pull-down menu 3604 may include numerous other options for configuring the assay device to perform assays.

FIG. 37 shows a report 3700 generated by an assay system according to one illustrated embodiment.

In particular, FIG. 37 illustrates the use of an assay system to quickly and efficiently test for multiple banned substances in a specimen. For example, an assay system may be used to test for instances of drugs of abuse in a urine specimen. The specimen may be held in a container of cup along with one or more assay strips. Advantageously, a single assay strip with multiple assays or test and control lines may be employed. Thus, for example, a holder 3710 may hold multiple assay strips 3712a-3712e (only two called out in FIG. 37), some of which assay strips 3712a, 3712e may have assays for two or more substances (e.g., assay strip 3712a: BZO, MTD, BAR; assay strip 3712e: mAmp, COC, THC).

The assay system may also establish a "chain-of-custody" by, for instance, reading or receiving unique identification information identifying an individual being tested or otherwise associated with a specimen and logically associating such unique identification information with the results of the analysis and/or with the images on which the analysis is based. A time stamp 3714 may be useful in establishing chain-of-custody.

The report 3700 may include identification information 3702 identifying the individual being subjected to testing. The identification information 3702 may be read or captured directly from an individual being subjected to testing or from identification material, such as government issued identification (e.g., drivers license, identity card, passport, military identification card), issued to the individual being subjected to testing. For example, the assay system may include or may be communicatively coupled to a reader that automatically reads information identifying information, either from the individual directly and/or from identification carried by or otherwise associated with the individual. The reader may include a sensor or transducer, for example an optical sensor or transducer and/or an audio sensor or transducer. The reader may read or capture biometric data or characteristics of the individual, for instance, a digital fingerprint, iris scan, facial scan, voiceprint, other physiological data, etc. The reader may read or capture an identifier from a piece of identification, for example by scanning or imaging the piece of identification. For instance, the reader may take the form of a machine-readable symbol reader such as a barcode scanner or imager to read machine-readable symbols (e.g., barcode symbols, area or matrix code symbols, stacked code symbols). Additionally or alternatively, the reader may take the form of a radio frequency identification (RFID) reader or interrogator to wirelessly read identification information from a wireless transponder such as an RFID tag, for instance via radio or microwave signals. The reader may additionally or alternatively take other forms, for instance an image or scanning for capturing human-readable information and pictures carried by the piece of identification. Additionally, or alternatively, the assay system may include or may be coupled to a user input device such as a keyboard or keypad which allows a user to enter identification information, which may, for example, be read by the user from a piece of identification carried by or otherwise associated with the individual being subjected to testing. Additionally, or alternatively, histories for the individual may be logically associated with the analysis. For instance, a patient history or a history of prior testing or analysis may be logically associated with the current analysis, and may optionally be reflected in report 3700.

The report 3700 may include a summary of assay results 3704. The summary of assay results 3704 may provide an abbreviated version of some or all of the results of the analysis performed. For example, the summary of assay results 3704 may simply indicate whether results where positive or negative.

The report 3700 may include a detailed listing of assay results 3706. The detailed listing of assay results 3706 may provide detailed information about all of the analysis. For example, detailed listing of assay results 3706 may provide density values, threshold values and results for each separate assay or control line of the particular assay or assay strip.

The report 3700 may include an image 3708 of the assay strip or strips. The image 3708 may show the results of multiple assays used to identify the presence and/or absence of multiple drugs of abuse from a single specimen. The image 3708 may also show identifying information, for example a machine-readable symbol that encodes a unique identifier that identifies the particular assay or assay strip. Such may be logically associated with an identifier that uniquely identifies the individual being subjected to the testing. While discussed herein as being used on a human individual, assay testing may be used on non-human animals as well, for example race horses.

Figure 38:
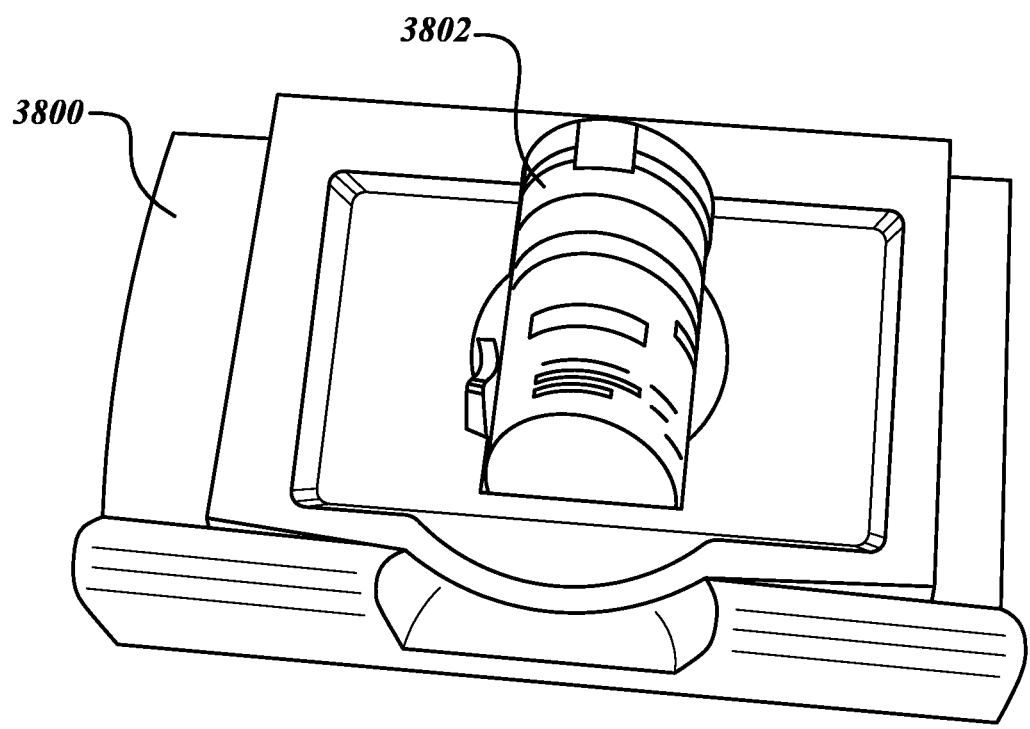
FIG. 38 is an isometric view of an assay system according to another illustrated embodiment for use with a container that holds a specimen and one or more assay strips.

FIG. 38 shows an assay system 3800 for use with a container 3802, according to one illustrated embodiment.

The assay system 3800 may be similar to the previously described assay systems, however includes at least one opening or slot 3804 sized to at least partially receive the container 3802 therein.

Figure 39:
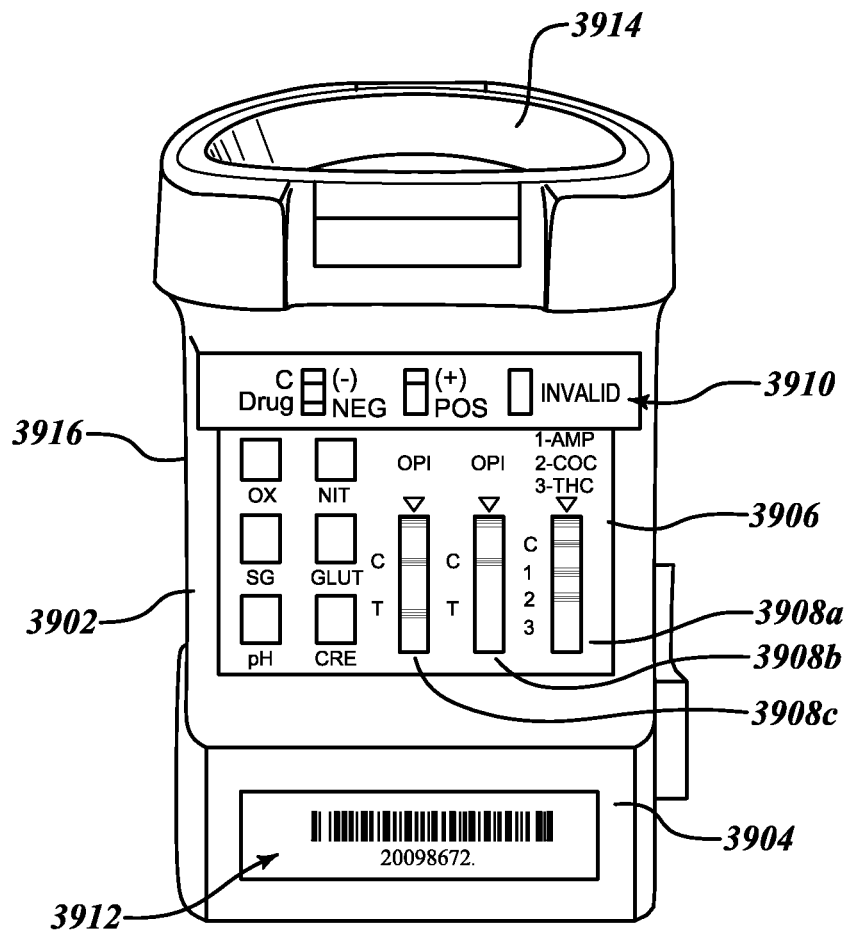
FIG. 39 is an isometric view according to one illustrated embodiment, of a container which holds a specimen and an assay carrier which holds a number of assay strips and which bears human-readable information.

FIG. 39 shows a container 3902, according to one illustrated embodiment.

The container 3902 contains or holds a specimen 3904, for example a bodily substance, for instance a bodily fluid such as urine or blood, taken or collected from an individual who is undergoing testing. The container 3902 may hold a strip carrier 3906 that carries one or more assay strips 3908a-3908c (only three called out in FIG. 39, collectively referred to as 3908). The assay strips 3908 may be similar to those previously described. Alternatively, the assay strips 3908 may be held in the container 3902, either in a free state or attached to the wall of the container 3902. The strip carrier 3906 may include various indicia, generally indicated as 3910. The indicia 3910 may, for example, identify a manufacturer and/or a test, as well as identify the various analysis or substances being tested for at various locations on the strip carrier 3906. For instance, an indication "OPI" may indicate a test for opiates, and indication "PCP" for the drug PCP, "AMP" for amphetamines, "COC" for cocaine, and "THC" for the active ingredient in cannabis. The strip carrier 3906 and/or the container may include identifying indicia 3912, which may be in machine-readable form such as a one- or two-dimensional symbol (e.g., barcode symbol, area or matrix code symbol, or stacked code symbol) and/or in human-readable form. Such may uniquely identify an individual from which the specimen was taken or collected, for example via a database that maps a unique identifier to the individual by name and/or identification number (e.g., social security number, driver's license number, employee number).

The container 3902 may include a top or cover 3914 to seal the contents within the container 3902. The container 3902 may advantageously have a relative flat portion 3916, which may facilitate imaging or image capture of the assay strips. While FIG. 39 illustrates only one shape and size of container, the assay system 3800 (FIG. 38) may accommodate any number of shapes and sizes of containers 3902. Further, while FIG. 39 only illustrates on shape and size of strip carrier 3906, any variety of shapes or sizes of strip carrier may be employed. Even further, any shape, size or number of assay strips 3908 may be employed.

Figure 40:
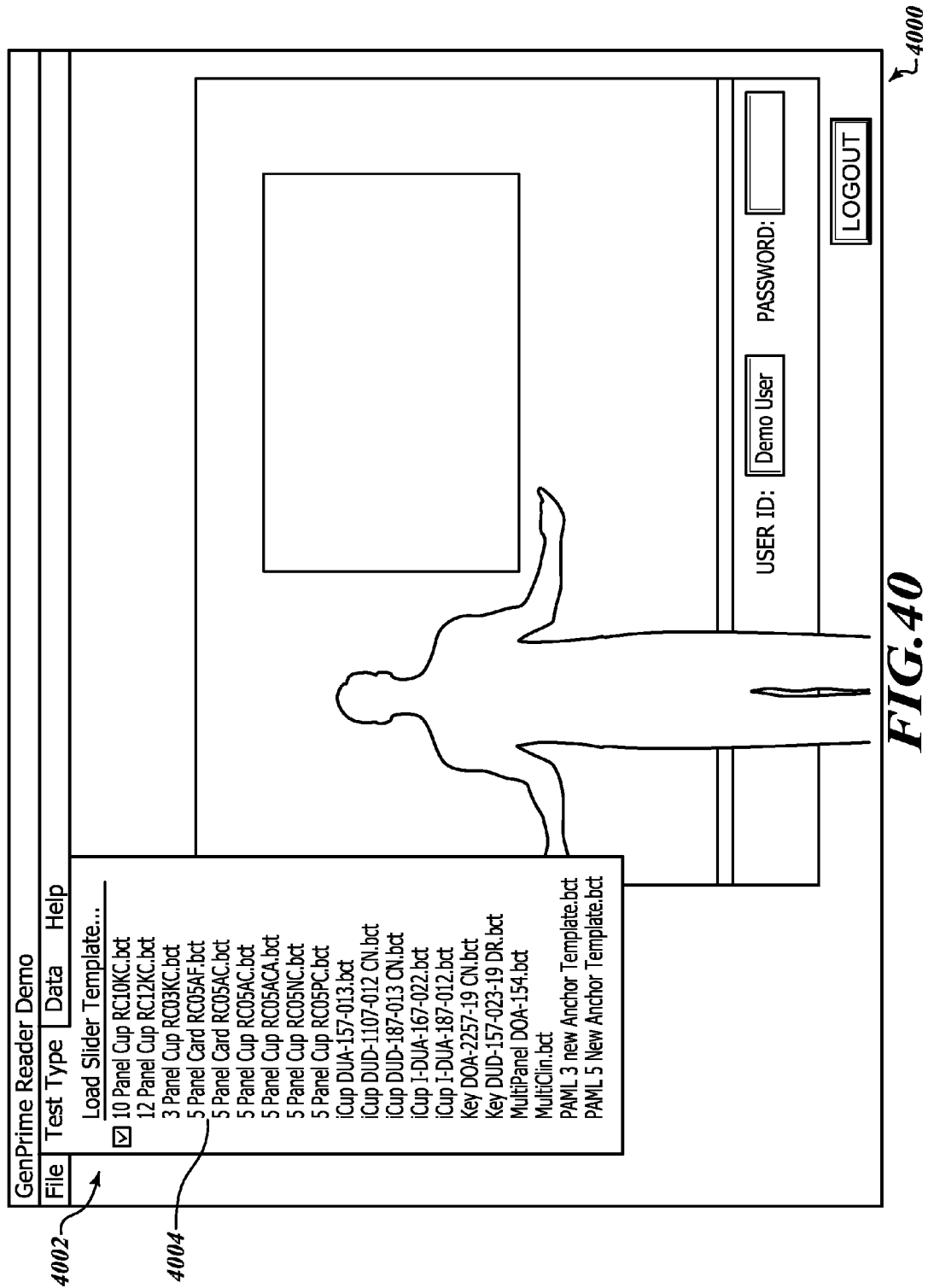
FIG. 40 is a screen print of a configuration screen of a user interface of the assay system of FIG. 38, according to one illustrated embodiment, the configuration screen allowing the user to configure the assay system 3800 to process different types of container, strip carriers and/or assay strips.

FIG. 40 shows a user interface of an assay system, according to one illustrated embodiment.

The assay system 3800 (FIG. 38) may provide a user interface 4000 to facilitate such variability, and ability to accommodate containers 3902 and/or strip carriers 3906 and/or assay strips 3908 from a large variety of manufacturers, producers or distributors. In particular, the assay system 3800 may have one or more user input devices, for instance one or more menus with user selectable icons, which allows a user to configure the assay system 3800 to analyze a particular container, strip carrier and/or assay strip. For instance, a pull-down menu 4002 may include a list of choices 4004 (only one called out in FIG. 40) which the user may select from. The choices 4004 may include selections indicative of various container types (e.g., cups). The choices 4004 may include selections indicative of various strip carrier formats (e.g., physical size, shape and/or position of assay strips on the strip carrier). The choices 4004 may include selections indicative of various assay strips (e.g., whether appearance or absence of line is a positive result, threshold, various substances being tested, size and dimension of assay strip, location of control line, etc.)

Such may be particularly suited for testing for banned or illicit substances such as prohibited drugs. Thus, a specimen (e.g., urine) 3904 may be collected in a container 3902 which holds an assay strip carrier 3906 that in turn holds one or more assay strips 3908. The container is sealed with the top or cover 3914, which may include a tamper resistance or tamper indicative seal which indicates if the top or cover has been tampered with after sealing. The container 3902 may include identifying information 3912, uniquely identifying the individual from which the specimen was taken. Thus, a chain-of-custody may be established. The contents of the container 3902 may be automatically analyzed or assessed via the assay system 3800, without opening the container 3902. Such may not only ensure that the chain-of-custody has not be broken, but may be more hygienic and efficient than other approaches to drug testing.

Figure 41:
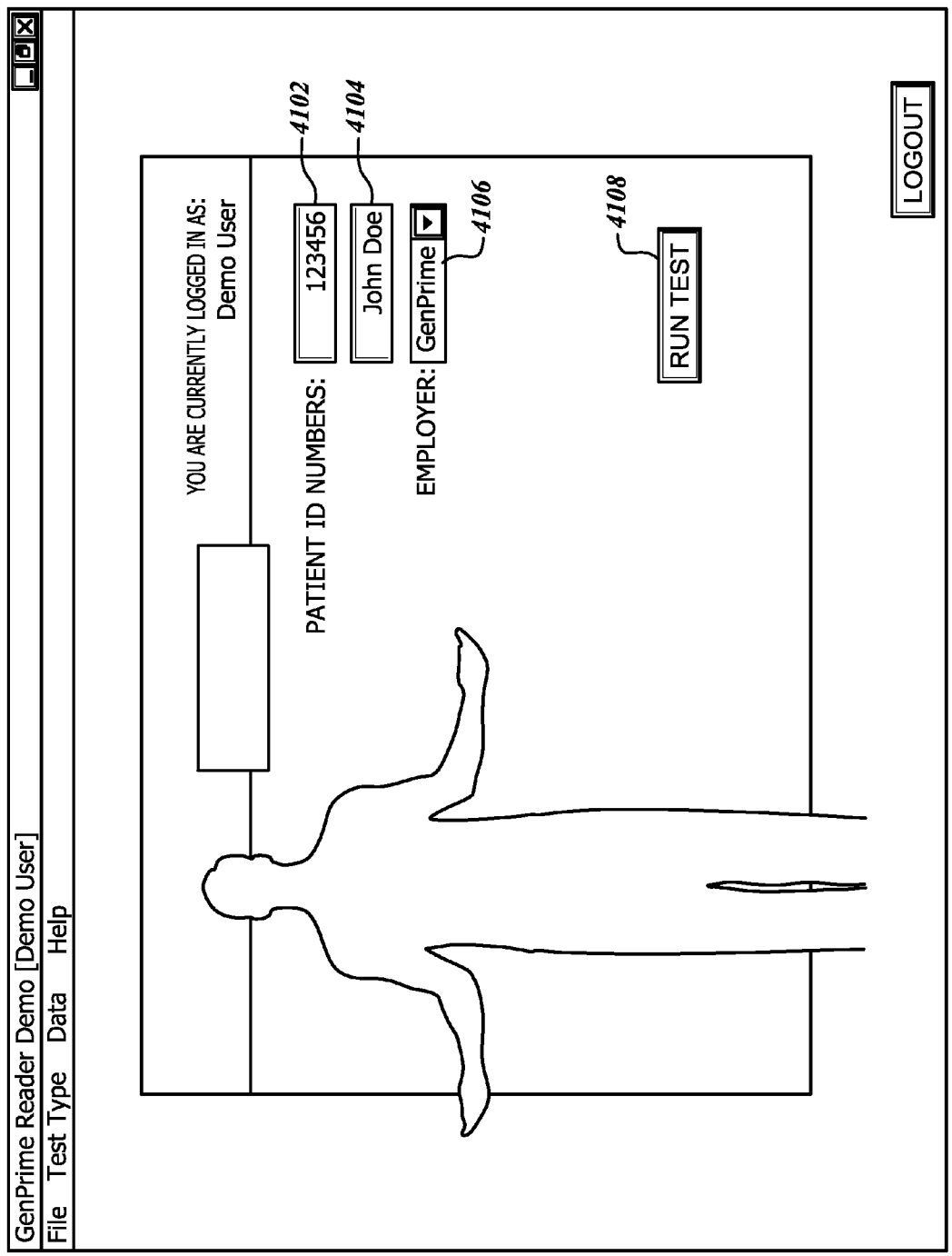
FIG. 41 is a screen print of an information entry screen of a user interface of the assay system of FIG. 38, according to one illustrated embodiment.

FIG. 41 shows a portion of a user interface in the form of a screen 4100, according to one illustrated embodiment.

The screen 4100 includes a unique identifier field 4102 that allows a user to enter a unique identifier for the individual subjected to testing, a name field 4104 to enter the name of the individual subjected to testing. The screen 4100 may include an employer identity field 4106 that allows the user to enter an identity of an employer or prospective employer for which the individual is being tested, or to select such employer or prospective employer identity from a drag down list. The screen 4100 may include a user selectable icon 4108 to cause the assay system 3800 (FIG. 3800) to run an assay or test using the user entered identity information.

Figure 42:
FIG. 42 is a screen print of a results screen of a user interface of the assay system of FIG. 38, according to one illustrated embodiment.

FIG. 42 shows a portion of a user interface in the form of a screen 4200, according to one illustrated embodiment.

The screen 4200 presents assay or test results. The screen 4200 may include an indication of positive or negative results (e.g., pass/fail) for one or more assays, generally indicated as 42002. The screen 4200 may include a high resolution image 4204 of the container, strip carrier and/or assay strips as captured by the assay system 3800 (FIG. 38). The screen 4200 may include user selectable checkboxes or other fields 4206 to indicate whether the test should be verified or overridden. The screen 4200 includes a user selectable re-scan icon 4208, selection of which causes the assay system 3800 to rescan the container and assay strips contained therein. The screen 4200 includes a user selectable new test icon 4210, selection of which causes the assay system 3800 to process a new container or run a different test on an existing container. The screen 4200 includes a user selectable logout icon 4208, selection of which causes the assay system 3800 to log out a current user.

Figure 43:
FIG. 43 is a schematic diagram of a database according to one illustrated embodiment, the database storing information about various ones of the tests or assays along with a copy of a high resolution image on which the tests or assays were based.

FIG. 43 shows a database 4300 according to one illustrated embodiment.

The database 4300 stores information 43002 (only one test or assay shown) related to tests or assays. Additional rows of information may be added to the database 4300 as additional specimens are processed. Information may include a package identifier (col. 1), a first patient identifier (col. 2) such as a unique identifier, a second patient identifier (col. 3) such as given and surname, and employer identifier (col. 4) and/or a package type identifier (col. 5) identifying the type of container and/or strip carrier. The information may also include a user identifier (col. 6) identifying the operator of the assay device during the specific assay, a date/time of the test or analysis (col. 7), an indication of the results of the test or analysis (col. 8), an indication of a user selected override result (col. 9), an indication of the actual line results (col. 10), an indication of whether the results were verified (col. 11), and/or an indication of whether adulteration occurred (col. 12).

The database 4300 also stores a copy of the high resolution image 4304 upon which the analysis or assay was performed.

A user selectable icon 4306 may allow user to print or export all of the data. A user selectable icon 4308 may allow user to print or export a selection portion of the data. A user selectable icon 4310 may allow user to edit the data.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other assay systems, not necessarily the exemplary lateral flow immunochromatographic assay strip system generally described above.

For example, the apparatus and/or method of acquiring an image may be different. For instance, a different model of scanner or imager could be used, such as a Fujitsu fi-60F scanner. In particular, the assay system may be altered to use a variety of optical scanning devices or imagers in place of the Avision AVA6+. The software could use a different driver model to communicate with the scanner or imager (e.g., WIA or SANE). The scanner or imager could be accessed remotely over a network instead of a direct cable connection. Also for instance, the parameters of the scan or imaging, such as color depth and resolution, could be modified; or the image could be acquired from a digital camera, frame grabber, or other acquisition device, or from a memory card, hard drive, or other storage device.

Also for example, the presence or type of machine-readable symbols and/or the apparatus and/or methods used to read them may be different. For instance, if the assay system did not employ machine-readable symbols such as barcode symbols, the assay system could alternatively rely on the user to explicitly indicate which identifying data set belongs to each assay strip. The user could do such via suitable user input device, for example entering identity information in fields on a screen via a keyboard or keypad, or other user input device. Thus, various identity fields (e.g., scan bag 1804, scan tube 1806, scan strip 1906, scan slot 2006) in various screens may not only display identifiers, by may allow the user to manually enter the appropriate identifiers via a user input device.

Also for example, the analysis algorithm can be customized to adapt to any given lateral flow immunochromatographic test strip. Also for example, the method used to locate assay strips within the entire scanned image may be modified. For instance, the acceptable range of hue, saturation, and brightness for each type of blob could be changed. Also for instance; the noise reduction methods could be changed. The expected weights of blobs or expected distances between blobs could be changed. The expected arrangement of blobs could be altered to detect a different series of assay strips. Indeed, searching the acquired image for the assay strip(s) (e.g., 106-1020, FIG. 10A) could be omitted completely. The assay device could alternatively locate the windows of each assay strip based on information provided by the user or calibration performed at the factory. For example, the user may identify the assay strip (e.g., center, boundary or periphery) by entering one or more points, lines or curves via a suitable user input device such as a touch screen or pointer device.

Also for example, any number of additional iterations of pixel transformation based on additional colors and/or blob analysis on the results of the additional iterations of pixel transformation may be performed. Such additional iterations may advantageously be employed to identify different or multiple assay types. Such may be based, for example, on specifications set out in data structures, such as customized templates.

Also for example, the specific data structures used to store blob and strip locations and represent the signal graph may be modified. As explained above, a template may be customized for each new assay type which the assay device is to recognize. In this way, the assay device may be reconfigured to recognize newly developed assay types or existing assay types which may become of interest to the operator of the assay device. Such may also accommodate new or different test strip physical or geometric configurations.

Also for example, the specific order of the acts used to produce the signal graph may be varied, some of the acts may be omitted, and/or additional acts may be performed. For instance, shadow detection could be eliminated or the assay system may assume a fixed-size shadow. Also for instance, the assay strips could be oriented horizontally instead of vertically. Also for instance, the enhanced average could be defined as the mean brightness for all rows.

Also for example, the method of locating the control and test background lines may be different. For instance, the endpoints could be moved, or the lines could be curved instead of straight.

As another example, the method of determining the line densities and making an assessment based on the values obtained in method 1040 (FIG. 10C), for instance at 1048-1064, may be different. For instance, the control line density could be based on some combination of A and B instead of CP and CB.

As yet another example, the specific values of all ranges and thresholds may be different or modified. For instance, a different assay strip type might require a different location for the control window, a different distance between the control and test windows, a different test line density indicative of a positive result, etc.

As a further example, the presence of a database or the contents of the records may be different than described above.

As yet a further example assay strips may take the form of any medium capable of being assayed, analyzed or otherwise evaluated for the presence or absence of an analyte. Examples of assay strips include chromatographic lateral flow strips or lateral flow strips, western blots, southern blots, electrophoresis gels, dot blots, etc. Some assay strips may produce a visible indication (e.g., a test result signal) in response to an absence of a particular substance, for example absence of a banned substance such as a drug, from a sample being tested. Assay strips which include inhibition assays may be employed. Assay strips may indicates a presence of a particular substance by an absence of a results line or other marking or indication.

Hence, described is apparatus, methods and articles that can accurately detect the presence or absence of test result or control signal lines in a non-subjective manner, while eliminating the misinterpretation of high background levels as a positive result. This is accomplished by a unique method of signal line detection and for background subtraction. Such may be customized to address any format of lateral flow immunochromatographic assay. In addition, all data and results are stored in an electronic database for future reference and verification.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An assay system to perform assays using assay strips, the assay system comprising:
   a housing having an interior and at least one entrance providing access to the interior, the at least one entrance sized to receive at least one assay strip therein without any assay strip carrier;
   a user interface including at least one user input device to receive a number of user selectable inputs that identify respective ones of a plurality of configuration modes which specify a respective set of configurable criteria for a respective type of assay strip, the configurable criteria which specifies at least one aspect of a physical format of the respective type of assay strip;
   an imager subsystem operable to capture images of any of the assay strips received in the interior of the housing; and
   a processor subsystem comprising at least one processor and at least one processor-readable memory communicatively coupled to the at least one processor, the at least one processor also communicatively coupled to the imager subsystem to receive image information representative of the images captured by the imager subsystem, the at least one processor configured to identify individual ones of the assay strips in the image from the image information, the at least one processor further configured to reconfigure the configurable criteria in accordance with the identified configuration mode in response to the receipt of the user selectable input, and perform an objective assay evaluation based at least in part on at least one signal line on each of the assay strips and based at least in part on at least one configurable criteria.

2. The assay system of claim 1 wherein the at least one processor is further configured to store a respective high resolution digital representation of the captured image of each of at least some of the assay strips to a computer-readable storage medium along with at least some identification information logically associated with the respective high resolution digital representation of the captured image of each of the at least some of the assay strips.

3. The assay system of claim 1 wherein the at least one processor is further configured to store a respective high resolution digital representation of the captured image of each of at least some of the assay strips to a computer-readable storage medium along with at least some information indicative of a result of the objective assay evaluation for each of at least some of the assay strips logically associated with the respective high resolution digital representation of the captured image of each of the at least some of the assay strips.

4. The assay system of claim 1, further comprising:
   a non-transitory computer-readable storage medium.

5. The assay system of claim 1, further comprising:
   a port that removably communicatively couples to the computer-readable storage medium and that is configured to write to the non-transitory computer-readable storage medium.

6. The assay system of claim 1 wherein the at least one processor is configured to identify individual ones of the assay strips in the image from the image information, by:
   a first iteration of pixel transformation based on a first color of a plurality of pixels;
   a first iteration of blob analysis on a set of the plurality of pixels resulting from the first iteration of pixel transformation to identify a first number of blobs; and
   a first iteration of blob pairing on the first number of blobs identified in the first iteration of blob analysis.

7. The assay system of claim 6 wherein the at least one processor is configured to identify individual ones of the assay strips in the image from the image information, further by:
   a second iteration of pixel transformation based on a second color of a plurality of pixels;
   a second iteration of blob analysis on a set of the plurality of pixels resulting from the second iteration of pixel transformation to identify a second number of blobs; and
   a second iteration of blob pairing on the second number of blobs identified in the second iteration of blob analysis.

8. The assay system of claim 1 wherein the at least one processor is further configured to identify any machine-readable symbols in the image from the image information, and to decode the identified machine-readable symbols, if any.

9. The assay system of claim 8 wherein at least some information decoded from the identified machine-readable symbols is the identification information, and wherein the at least one processor is configured to logically associate the identification information with respective ones of the assay strips which carried the machine-readable symbol.

10. The assay system of claim 1 wherein the configurable criterion includes a threshold level for the objective assay evaluation.

11. The assay system of claim 1 wherein the configurable criterion includes at least one aspect of a physical format of the assay strips of the respective type of assay strip.

12. The assay system of claim 1 wherein at least two of the configuration modes are mapped to respective assay strips from at least two different flow strip producing commercial entities.

13. The assay system of claim 1 wherein the user interface includes at least one input device configured to allow the entry of a subject identifier that uniquely identifies a subject from which a sample on the assay strip was taken, and wherein the at least one processor is configured to store a logical association between the objective assay evaluation of the assay strip and the subject identifier.

14. The assay system of claim 1 wherein the at least one processor configured to perform the objective assay evaluation by objectively quantifying an intensity of at least one positive results signal line on each of the assay strips.

15. The assay system of claim 1 wherein the at least one processor configured to perform the objective assay evaluation by evaluating at least one control signal line on each of the assay strips.

16. The assay system of claim 1 wherein the image subsystem includes a two dimensional array that images an area greater than an area of a single assay strip.

17. The assay system of claim 1 wherein the image subsystem includes a one dimensional array mounted for movement with respect to the at least one assay strip to image an area greater than an area of a single assay strip.

18. The assay system of claim 1 wherein the interior of the housing is dark and the image subsystem includes a least one of a mirror, a prism, an optical filter or an image processing filter.

19. The assay system of claim 1 wherein the entrance includes a plurality of slots, each slot sized and dimensioned to receive a respective one of the assay strips therein.

20. An assay system to perform assays using assay strips, the assay system comprising:

a housing having an entrance sized to receive at least one assay strip therein;

an imager subsystem operable to capture images of any of the assay strips received in the entrance of the housing;

a processor subsystem comprising at least one processor communicatively coupled to the imager subsystem to receive image information representative of the images captured by the imager subsystem, the at least one processor configured to perform an objective assay evaluation based at least in part on at least one test results signal line and at least one control signal line on each of the assay strips and based at least in part on at least one configurable criteria; and a user interface including at least one user input device to receive a number of user selectable inputs that identify respective ones of a number of configuration modes which specify a respective set of configurable criteria for a respective type of assay strip, the configurable criteria to specify at least one aspect of a physical format of the respective type of assay strip, and where in response to the receipt of one of the user selectable inputs the processor subsystem reconfigures the at least one configurable criteria used to perform the objective assay evaluation.

21. The assay system of claim 20 wherein the at least one configurable criteria includes a threshold level to objectively evaluate the test results signal line.

22. The assay system of claim 20 wherein the at least one configurable criteria includes at least one aspect of a physical format of the assay strips of the respective type of assay strip.

23. The assay system of claim 20 wherein at least two of the configuration modes are mapped to respective assay strips of at least two different types.

24. The assay system of claim 20 wherein at least two of the configuration modes are mapped to respective assay strips of at least two different immunochromatographic tests.

25. The assay system of claim 20 wherein at least two of the configuration modes are mapped to respective assay strips from at least two different assay strip producing commercial entities.

26. The assay system of claim 20 wherein the user interface includes indicia indicative of a plurality of different assay strip products.

27. The assay system of claim 20 wherein the at least one processor configured to perform the objective assay evaluation by objectively quantifying an intensity of at least one positive results signal line on each of the assay strips.

28. The assay system of claim 20 wherein the at least one processor configured to perform the objective assay evaluation by evaluating at least one control signal line on each of the assay strips.

* * * * *